(12) United States Patent
Fujimoto et al.

(10) Patent No.: US 10,407,619 B2
(45) Date of Patent: Sep. 10, 2019

(54) LIQUID CRYSTAL COMPOSITION

(71) Applicant: Sumitomo Chemical Company, Limited, Tokyo (JP)

(72) Inventors: Daichi Fujimoto, Osaka (JP); Noriyuki Hida, Osaka (JP); Tatsuaki Kasai, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 6 days.

(21) Appl. No.: 15/598,882

(22) Filed: May 18, 2017

(65) Prior Publication Data
US 2017/0335191 A1    Nov. 23, 2017

(30) Foreign Application Priority Data
May 23, 2016  (JP) ................. 2016-102489

(51) Int. Cl.
| | | |
|---|---|---|
| G02F 1/1333 | (2006.01) | |
| C09K 19/38 | (2006.01) | |
| C07D 277/64 | (2006.01) | |
| G02F 1/13363 | (2006.01) | |
| C09K 19/34 | (2006.01) | |
| C09K 19/56 | (2006.01) | |
| G02B 5/00 | (2006.01) | |
| G02F 1/1335 | (2006.01) | |
| C09K 19/04 | (2006.01) | |

(52) U.S. Cl.
CPC ........ C09K 19/3809 (2013.01); C07D 277/64 (2013.01); C09K 19/3497 (2013.01); C09K 19/56 (2013.01); G02B 5/00 (2013.01); G02F 1/13363 (2013.01); C09K 2019/0448 (2013.01); G02F 1/133528 (2013.01); G02F 2001/133631 (2013.01)

(58) Field of Classification Search
CPC ............. C09K 19/56; C09K 19/3809; C09K 2019/0448; C09K 2019/3497; G02F 1/1333; G02F 1/13363; G02F 1/133528; G02F 2001/133631; G02B 5/00; C07D 277/64
USPC .................................................. 252/299.01
See application file for complete search history.

(56) References Cited

U.S. PATENT DOCUMENTS

| 9,784,894 B2 * | 10/2017 | Kobayashi ............. B32B 38/10 |
| 2011/0210322 A1 * | 9/2011 | Ishii ..................... C07D 251/24 257/40 |
| 2015/0183902 A1 | 7/2015 | Sakamoto et al. |
| 2017/0145312 A1 * | 5/2017 | Hida ..................... C08F 222/24 |
| 2017/0283700 A1 * | 10/2017 | Yoshioka ............ C08F 122/105 |

FOREIGN PATENT DOCUMENTS

| JP | 2002069450 A | 3/2002 |
| JP | 2010-31223 A | 2/2010 |
| JP | 2011-207765 A | 10/2011 |
| JP | 2012052107 A | 3/2012 |
| JP | 2015-157776 A | 9/2015 |
| WO | 2013180217 A1 | 12/2013 |

OTHER PUBLICATIONS

Office Action dated Jul. 18, 2017 in JP Application No. 2017-081525.

* cited by examiner

*Primary Examiner* — Geraldina Visconti
(74) *Attorney, Agent, or Firm* — Panitch Schwarze Belisario & Nadel LLP

(57) ABSTRACT

A liquid crystal composition which prevents production of an alignment defect of a liquid crystal compound and also has excellent storage stability during dissolution in a solvent is provided. The liquid crystal composition is suitable for constituting a retardation film capable of favorable circular polarization conversion. The liquid crystal composition includes a polymerizable liquid crystal compound having 3 or more ring structures in the main chain, and aluminum. A content of the aluminum is 1 ppm or more and 170 ppm or less relative to the polymerizable liquid crystal compound.

12 Claims, No Drawings

LIQUID CRYSTAL COMPOSITION

BACKGROUND OF THE INVENTION

Field of the Invention

The present invention relates to a liquid crystal composition, and also relates to a retardation film, a polarizing plate, and an optical display containing the liquid crystal composition.

Description of the Related Art

An optical film, such as a retardation film, used in a flat panel display (FPD), include, for example, an optical film which is obtained as follows: coating a coating liquid to supporting substrate, which is obtained by dissolving a polymerizable liquid crystal compound in a solvent, and then polymerizing the coated liquid to obtain the optical film. Conventionally, examples of known polymerizable liquid crystal compounds include a rod-like structured nematic liquid crystal compound which is composed of a coupled 2 to 4 of six-membered rings (e.g., "Liquid Crystal Handbook", edited by Liquid Crystal Handbook Editorial Committee, 312 (2000)).

On the other hand, a retardation film is required to have a polarization conversion ability in all wavelength range as one of its properties. It is known that uniform polarization conversion is theoretically possible in the wavelength range in which the retardation film shows reverse wavelength dispersibility satisfying [Re(450)/Re(550)]<1 and [Re(650)/Re(550)]>1. As a polymerizable compound which can constitute the above-mentioned retardation film, a compound disclosed in JP-A-2011-207765 is known.

SUMMARY OF THE INVENTION

When a coating type optical film, such as that mentioned above, is produced, a high solubility of a polymerizable liquid crystal compound in a solvent is required. However, most of the above-mentioned polymerizable liquid crystal compounds have poor solubility in various solvents caused by their chemical structures. Thus, during storage of a coating liquid, a polymerizable liquid crystal compound sometimes crystallizes to produce precipitate, and the precipitated crystal is a cause of a defect of an optical film. Further, generally, in order to increase solubility in a solvent, in a compound having many cyclic structures, a technique of introducing along-chain alkyl group is used. However, in a polymerizable liquid crystal compound, when a long-chain alkyl group is introduced as a substituent, molecular alignment of the liquid crystal compound is disorganized by the introduced substituent, which lead to production of an alignment defect in an optical film.

Accordingly, it is an object of the present invention to provide a liquid crystal composition containing a polymerizable liquid crystal compound in which the liquid crystal composition prevents production of an alignment defect of a liquid crystal compound and also has excellent storage stability during dissolution in a solvent, and preferably is suitable for constituting a retardation film capable of favorable circular polarization conversion.

The present invention provides the following preferable aspects [1] through [12].

[1] A liquid crystal composition comprising a polymerizable liquid crystal compound having 3 or more ring structures in the main chain, and aluminum, wherein a content of the aluminum is 1 ppm or more and 170 ppm or less relative to the polymerizable liquid crystal compound.

[2] The liquid crystal composition according to [1] above, comprising at least one organic solvent selected from the group consisting of an amide-based solvent, a ketone-based solvent, an ether-based solvent, and an ester-based solvent.

[3] The liquid crystal composition according to [1] or [2] above, wherein the polymerizable liquid crystal compound is a polymerizable liquid crystal compound represented by the following formula (A):

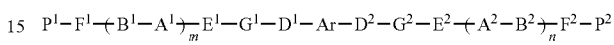

(A)

in formula (A), m and n, each independently, represent an integer of 0 to 3, $B^1$, $B^2$, $D^1$, $D^2$, $E^1$, and $E^2$, each independently, represent —$CR^1R^2$—, —$CH_2$—$CH_2$—, —O—, —S—, —CO—O—, —O—CO—, —O—CO—O—, —C(=S)—O—, —O—C(=S)—, —O—C(=S)—O—, —CO—$NR^1$—, —$NR^2$—CO—, —O—$CH_2$—, —$CH_2$—O—, —S—$CH_2$—, —$CH_2$—S—, or a single bond, and $R^1$ and $R^2$, each independently, represent a hydrogen atom, a fluorine atom, or an alkyl group having 1 to 4 carbon atoms, $A^1$, $A^2$, $G^1$, and $G^2$, each independently, represent a divalent alicyclic hydrocarbon group having 3 to 16 carbon atoms or a divalent aromatic hydrocarbon group having 6 to 20 carbon atoms, wherein a hydrogen atom contained in the alicyclic hydrocarbon group and the aromatic hydrocarbon group can be replaced by a halogen atom, —$R^3$, —$OR^3$, a cyano group, or a nitro group, —$CH_2$— contained in the alicyclic hydrocarbon group can be replaced by —O—, —S—, —NH—, or —$NR^4$—, —CH(—)— contained in the alicyclic hydrocarbon group can be replaced by —N(—)—, $R^3$ and $R^4$, each independently, represent an alkyl group having 1 to 4 carbon atoms, wherein a hydrogen atom contained in the alkyl group can be replaced by a fluorine atom, $F^1$ and $F^2$, each independently, represent an alkane diyl group having 1 to 12 carbon atoms, wherein a hydrogen atom contained in the alkane diyl group can be replaced by —$OR^3$ or a halogen atom, and —$CH_2$— contained in the alkane diyl group can be replaced by —O— or —CO—, $P^1$ and $P^2$, each independently, represent a hydrogen atom or a polymerizable group, with the proviso that at least one of $P^1$ and $P^2$ represents a polymerizable group, Ar is an optionally substituted divalent aromatic group, wherein at least one nitrogen atom, oxygen atom, or sulfur atom is contained the aromatic group.

[4] The liquid crystal composition according to [3] above, wherein both $G^1$ and $G^2$ are trans-cyclohexane-1,4-diyl groups.

[5] The liquid crystal composition according to [3] or [4] above, wherein Ar in the formula (A) is an aromatic group having 10 or more and 30 or less π-electrons.

[6] The liquid crystal composition according to any of [1] to [5] above, wherein a maximum absorption wavelength ($\lambda_{max}$) of the polymerizable liquid crystal compound is 300 to 400 nm.

[7] The liquid crystal composition according to any of [3] to [6] above, wherein Ar in the formula (A) is an aromatic group having a heterocycle.

[8] The liquid crystal composition according to [7] above, wherein the aromatic group having a heterocycle is an aromatic group having a benzothiazole group.

[9] A retardation film made from a liquid crystal composition according to any of [1] to [8] above.

[10] The retardation film according to [9] above, satisfying the following formula (1):

$$0.80 \leq Re(450)/Re(550) < 1.00 \quad (1)$$

wherein $Re(\lambda)$ represents a front retardation value with respect to a light having a wavelength of $\lambda$ nm.

[11] A polarizing plate comprising the retardation film according to [9] or [10] above.

[12] An optical display comprising the polarizing plate according to [11] above.

The present invention can provide a liquid crystal composition which prevents production of an alignment defect of a liquid crystal compound and also has excellent storage stability during dissolution in a solvent.

DETAILED DESCRIPTION OF THE PREFERRED EMBODIMENTS

A liquid crystal composition according to the present invention contains a polymerizable liquid crystal compound having 3 or more ring structures in the main chain. In the present invention, the expression "main chain" refers to a principle carbon chain of a molecular chain of the polymerizable liquid crystal compound, and has the most carbon atoms, and thus the "main chain" corresponds to a trunk of the compound.

<Polymerizable Liquid Crystal Compound>

A polymerizable liquid crystal compound contained in a liquid crystal composition according to the present invention has 3 or more ring structures in the main chain. Examples of the ring structure which can be contained in the main chain of the polymerizable liquid crystal compound include a monovalent or divalent alicyclic hydrocarbon group, aromatic hydrocarbon group, and aromatic heterocyclic group. Each of the ring structures can be monocyclic or polycyclic. Further, when the ring structure is polycyclic, the ring structure can be a fused-type polycyclic structure or an assembled-type polycyclic structure.

Examples of the monocyclic ring structure include an alicyclic hydrocarbon group, aromatic hydrocarbon group, or aromatic heterocyclic group having 3 to 20 membered ring structure, and further include an alicyclic hydrocarbon group, aromatic hydrocarbon group, or aromatic heterocyclic group preferably having preferably 4 to 10 membered ring structure, more preferably having 5 membered ring or 6 membered ring structure, and further more preferably having 6 membered ring structure. Specifically, examples of the ring structure include a benzene ring, a cyclohexane ring, a pyrimidine ring, a pyridazine ring, a pyrazine ring, a pyridine ring, a piperidine ring, a tetrahydropyran ring, a dioxane ring, and a thiazine ring.

Examples of the polycyclic ring structure of include a polycyclic aromatic group, an aromatic heterocyclic group, and a polycyclic aliphatic hydrocarbon group, and a polycyclic aromatic group having a heterocycle is preferred. Specifically, examples of the ring structure include an indole group, a benzimidazole group, a benzofuran group, a benzothiophene group, and a benzothiazole group.

The number of the ring structure in the polymerizable liquid crystal compound is 3 or more, preferably 13 or less, more preferably 9 or less, preferably 5 or more, further more preferably 5 or more and 7 or less, particularly preferably the number of the ring structure is 5. When the main chain has 3 or more, or 5 or more ring structures, a liquid crystal phase has elevated heat stability. Further, in the present invention, when the ring structure is a polycyclic group, the group is regarded as one ring structure as a whole.

The polymerizable liquid crystal compound contained in the liquid crystal compound of the present invention is a compound preferably having 3 or more, more preferably 5 or more ring structures in the main chain represented by the following formula (A). The main chain contains preferably 2 or more monocyclic ring structures, more preferably 4 or more monocyclic ring structures. When the polymerizable liquid crystal compound is a compound represented by the following formula (A), the compound has an excellent solubility in a solvent, and hardly produces an alignment defect, and thus a desired effect of the present invention can be exerted more favorably.

Formula (A):

[Chemical Formula 1]

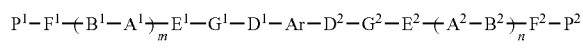

(A)

In formula (A), m and n, each independently, represent an integer of 0 to 3, and when m is an integer of 2 or more, 2 or more of $A^1$ and $B^1$ may be the same with or different from each other, and when n is an integer of 2 or more, 2 or more of $A^2$ and $B^2$ may be the same with or different from each other.

$B^1$, $B^2$, $D^1$, $D^2$, $E^1$, and $E^2$, each independently, represent —$CR^1R^2$—, —$CH_2$—, —O—, —S—, —CO—O—, —O—CO—, —O—CO—O—, —C(=S)—O—, —O—C(=S)—, —O—C(=S)—O—, —CO—$NR^1$—, —$NR^2$—CO—, —O—$CH_2$—, —$CH_2$—O—, —S—$CH_2$—, —$CH_2$—S—, or a single bond, and $R^1$ and $R^2$ each independently, represent a hydrogen atom, a fluorine atom, or an alkyl group having 1 to 4 carbon atoms.

$A^1$, $A^2$, $G^1$, and $G^2$, each independently, represent a divalent alicyclic hydrocarbon group having 3 to 16 carbon atoms or a divalent aromatic hydrocarbon group having 6 to 20 carbon atoms, wherein a hydrogen atom contained in the alicyclic hydrocarbon group and the aromatic hydrocarbon group can be replaced by a halogen atom, —$R^3$, —$OR^3$, a cyano group, or a nitro group, —$CH_2$— contained in the alicyclic hydrocarbon group can be replaced by —O—, —S—, —NH—, or —$NR^4$—, —CH(—)— contained in the alicyclic hydrocarbon group can be replaced by —N(—)—, $R^3$ and $R^4$, each independently, represent an alkyl group having 1 to 4 carbon atoms, wherein a hydrogen atom contained in the alkyl group can be replaced by a fluorine atom.

$F^1$ and $F^2$, each independently, represent an alkane diyl group having 1 to 12 carbon atoms, wherein a hydrogen atom contained in the alkane diyl group can be replaced by —$OR^3$ or a halogen atom, and —$CH_2$— contained in the alkane diyl group can be replaced by —O— or —CO—.

$P^1$ and $P^2$, each independently, represent a hydrogen atom or a polymerizable group, with the proviso that at least one of $P^1$ and $P^2$ represents a polymerizable group.

Ar is an optionally substituted divalent aromatic group, wherein at least one nitrogen atom, oxygen atom, or sulfur atom is contained in the aromatic group.

In formula (A), m and n, each independently, represent an integer of 0 to 3. When a polymerizable liquid crystal compound has 5 or more ring structures in the main chain, if any one of m and n is 0, the other one represents an integer of 2 or 3. m and n are preferably 1 or 2, and more preferably 1. Further, from the view points of ease for producing a polymerizable liquid crystal compound and reducing its production cost, preferably m and n are the same integer. Moreover, when m and n are 2 or 3, plurality of A and B may be the same with or different from each other. From the view point of ease of production of a polymerizable liquid crystal compound industrially, preferably plurality of A and B are the same with each other.

In formula (A), $B^1$, $B^2$, $D^1$, $D^2$, $E^1$, and $E^2$, each independently, represent —$CR^1R^2$—, —$CH_2$—$CH_2$—, —O—, —S—, —CO—O—, —O—CO—, —O—CO—O—, —C(=S)—O—, —O—C(=S)—, —O—C(=S)—O—, —CO—$NR^1$—, —$NR^2$—CO—, —O—$CH_2$—, —$CH_2$—O—, —S—$CH_2$—, —$CH_2$—S—, or a single bond. In the formula, $R^1$ and $R^2$, each independently, represent a hydrogen atom, a fluorine atom, or an alkyl group having 1 to 4 carbon atoms.

From the view point of ease of generation of liquid crystal phase, $B^1$ and $B^2$, each independently, are preferably —O—, —S—, —O—CO—, —CO—O—, —O—CO—O—, —O—C(=S)—, —O—C(=S)—O—, —O—$CH_2$—, or —$CH_2$—O—, more preferably —O—, —O—CO—, or —CO—O—. From the view points of ease for producing a polymerizable liquid crystal compound and reducing its production cost, $B^1$ and $B^2$ are preferably the same with each other. The expression "$B^1$ and $B^2$ are the same with each other" means that structures of $B^1$ and $B^2$ are the same with each other viewed from Ar as the central point. For example, when $B^1$ is —O—CO—, $B^2$ which is the same with $B^1$ is —CO—O—. Likewise, the same applies to the relations between $D^1$ and $D^2$, $E^1$ and $E^2$, $A^1$ and $A^2$, $G^1$ and $G^2$, $F^1$ and $F^2$, and $P^1$ and $P^2$.

From the view point of ease of generation of liquid crystal phase, $D^1$, $D^2$, $E^1$, and $E^2$, each independently, are preferably —O—, —S—, —O—CO—, —CO—O—, —O—CO—O—, —CO—$NR^1$—, or —$NR^2$—CO—, more preferably —O—, —O—CO—, or —CO—O—. From the view points of ease for producing a polymerizable liquid crystal compound and reducing its production cost, $D^1$ and $D^2$ are, and $E^1$ and $E^2$ are preferably the same with each other.

In formula (A), $A^1$, $A^2$, $G^1$, and $G^2$, each independently, represent a divalent alicyclic hydrocarbon group having 3 to 16 carbon atoms or a divalent aromatic hydrocarbon group having 6 to 20 carbon atoms. The number of carbon atoms contained in the divalent alicyclic hydrocarbon group is preferably 4 to 15, more preferably 5 to 10, further more preferably 5 or 6. The number of carbon atoms contained in the divalent aromatic hydrocarbon group is preferably 6 to 18, more preferably 6 to 16, further more preferably 5 or 6. A hydrogen atom contained in the alicyclic hydrocarbon group and the aromatic hydrocarbon group can be replaced by —$R^3$, —$OR^3$, a cyano group, or a nitro group. Then, $R^3$ represents an alkyl group having 1 to 4 carbon atoms, wherein a hydrogen atom contained in the alkyl group can be replaced by a fluorine atom.

Examples of the alkyl group having 1 to 4 carbon atoms include a methyl group, an ethyl group, a propyl group, an isopropyl group, a butyl group, an isobutyl group, a sec-butyl group, and a tert-butyl group. The alkyl group is preferably an alkyl group having 1 or 3 carbon atoms, more preferably an alkyl group having 1 or 2 carbon atoms, particularly preferably a methyl group.

Examples of the alkoxy group having 1 to 4 carbon atoms in —$OR^3$ include a methoxy group, an ethoxy group, a propoxy group, an isopropoxy group, a butoxy group, an isobutoxy group, a sec-butoxy group, and a tert-butoxy group. The alkoxy group is preferably an alkoxy group having 1 to 3 carbon atoms, more preferably an alkoxy group having 1 or 2 carbon atoms, particularly preferably a methoxy group.

Examples of the divalent alicyclic hydrocarbon group include a cycloalkane diyl group, and the like. A methylene group (—$CH_2$—) contained in the alicyclic hydrocarbon group can be replaced by —O—, —S—, —NH—, or —$NR^4$—, and —CH(—)— can be replaced by —N(—)—. Then, $R^4$ represents a hydrogen atom or an alkyl group having 1 to 4 carbon atoms.

Examples of the divalent alicyclic hydrocarbon group include groups represented by the following formula (g-1) to formula (g-4). Examples of the divalent alicyclic hydrocarbon group in which —$CH_2$— contained in the alicyclic hydrocarbon group is replaced by —O—, —S—, —NH—, or —$NR^4$— include groups represented by the following formula (g-5) to formula (g-8). Examples of the divalent alicyclic hydrocarbon group in which —CH(—)— contained in the alicyclic hydrocarbon group is replaced by —N(—)— include groups represented by the following formula (g-9) and formula (g-10). The above-mentioned divalent alicyclic hydrocarbon groups are preferably 5 membered or 6 membered alicyclic hydrocarbon groups.

[Chemical Formula 2]

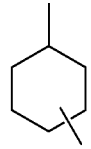
(g-1)

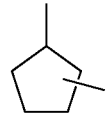
(g-2)

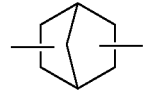
(g-3)

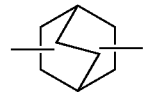
(g-4)

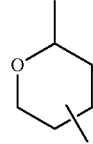
(g-5)

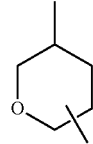
(g-6)

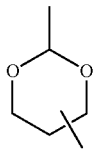
(g-7)

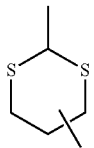
(g-8)

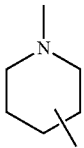
(g-9)

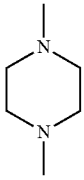
(g-10)

The divalent alicyclic hydrocarbon group is preferably a group represented by formula (g-1), more preferably a cyclohexane-1,4-diyl group, particularly preferably a trans-cyclohexane-1,4-diyl group.

Examples of the divalent aromatic hydrocarbon group include groups represented by formula (a-1) to (a-8). The divalent aromatic hydrocarbon group is preferably a 1,4-phenylene group.

[Chemical Formula 3]

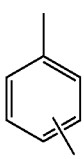
(a-1)

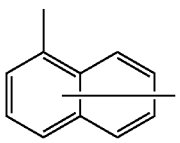
(a-2)

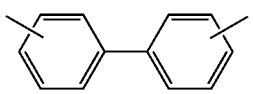
(a-3)

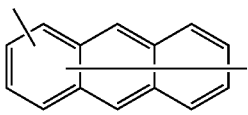
(a-4)

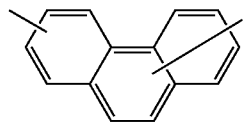
(a-5)

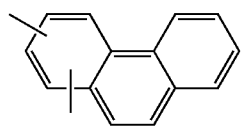
(a-6)

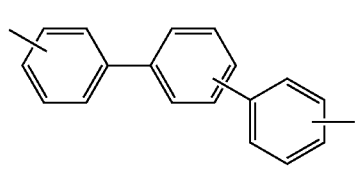
(a-7)

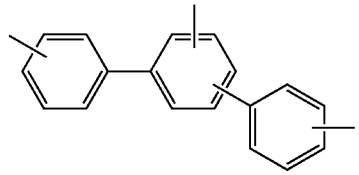
(a-8)

In one embodiment of the present invention, from the view point of production of a compound of the present invention, A and $A^2$, each independently, are preferably a divalent aromatic hydrocarbon group. Further, in one embodiment of the present invention, from the view point of production of a compound of the present invention, $G^1$ and $G^2$, each independently, are preferably a divalent alicyclic hydrocarbon group, more preferably a trans-cyclohexane-1,4-diyl group, and particularly preferably both $G^1$ and $G^2$ are a trans-cyclohexane-1,4-diyl group. When both $G^1$ and $G^2$ are a trans-cyclohexane-1,4-diyl group, particularly preferable liquid crystallinity is exerted. Moreover, from the view points of ease for producing a polymerizable liquid crystal compound and reducing its production cost, $A^1$ and $A^2$ are, and $G^1$ and $G^2$ are preferably the same with each other.

In formula (A), $F^1$ and $F^2$, each independently, represent an alkane diyl group having 1 to 12 carbon atoms, preferably having 2 to 15 carbon atoms, more preferably having 3 to 12 carbon atoms, further more preferably having 4 to 10 carbon atoms. A hydrogen atom contained in the alkane diyl group can be replaced by —$OR^3$ or a halogen atom, and —$CH_2$— contained in the alkane diyl group can be replaced by —O— or —CO—. $R^3$ represents an alkyl group having 1 to 4 carbon atoms, wherein a hydrogen atom contained in the alkyl group can be replaced by a fluorine atom. From the view points of ease for producing a polymerizable liquid crystal compound and reducing its production cost, $F^1$ and $F^2$ are preferably the same with each other.

In formula (A), $P^1$ and $P^2$, each independently, represent a hydrogen atom or a polymerizable group. With the proviso however, that at least one of $P^1$ and $P^2$ is a polymerizable group, and preferably both $P^1$ and $P^2$ are polymerizable groups. A polymerizable group refers to a group containing a group which can take part in a polymerization reaction. Examples of the group which can take part in a polymerization reaction include a vinyl group, a p-(2-phenylethenyl) phenyl group, an acryloyl group, an acryloyloxy group, a methacryloyl group, a methacryloyloxy group, a carboxyl group, a methylcarbonyl group, a hydroxyl group, a carbamoyl group, an alkylamino group having 1 to 4 carbon atoms, an amino group, a formyl group, —N=C=O, —N=C=S, an oxiranyl group, and an oxetanyl group.

From the viewpoint of suitability for photopolymerization, the polymerizable group is preferably a radical polymerizable group or a cationic polymerizable group. Particularly, from the view points of easy handling and production, the polymerizable group is preferably an acryloyl group, an acryloyloxy group, a methacryloyl group, or a methacryloyloxy group, and from the viewpoint of high polymerizability, is more preferably an acryloyl group or an acryloyloxy group.

In formula (A), the divalent aromatic group represented by Ar contains at least one nitrogen atom, oxygen atom, or sulfur atom. Then, in the present invention, the expression 'the divalent aromatic group represented by Ar "contains at least one nitrogen atom, oxygen atom, or sulfur atom"' means that the Ar only have to contain the heteroatoms, and the Ar can have a heterocycle or does not have to have a heterocycle. From the view point of providing reverse wavelength dispersibility of an obtained retardation film, the divalent aromatic group represented by Ar is preferably an aromatic group having a heterocycle. Examples of the aromatic group include aromatic groups having a furan ring, a benzofuran ring, a pyrrole ring, a thiophene ring, a pyridine ring, a thiazole ring, a benzothiazole ring, a phenanthroline ring, and the like. Especially, the divalent aromatic group is more preferably an aromatic group having a benzene ring, a thiazole ring, or a benzothiazole ring, furthermore preferably an aromatic group having a benzothiazole ring.

The aromatic group represented by Ar preferably has a π-electron. From the view point of providing reverse wavelength dispersibility of a retardation film obtained from a liquid crystal composition, the total number of π-electrons ($N_\pi$) contained in the aromatic group is preferably 10 or more, more preferably 12 or more, furthermore preferably 14 or more, and preferably 30 or less, more preferably 25 or less.

Examples of the aromatic group represented by Ar include the following groups.

[Chemical Formula 4]

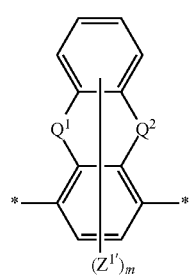

(Ar-1)

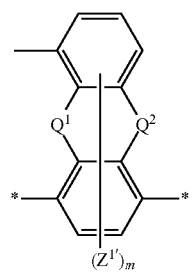

(Ar-2)

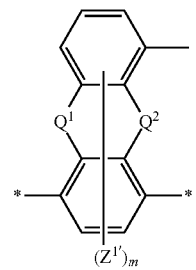

(Ar-3)

(Ar-4)

(Ar-5)

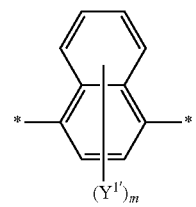

(Ar-6)

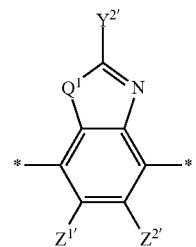

(Ar-7)

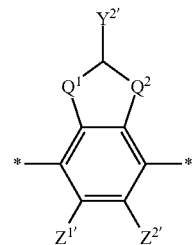

(Ar-8)

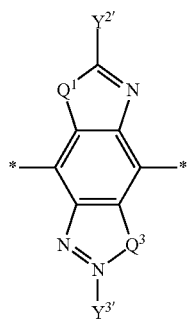 (Ar-9)
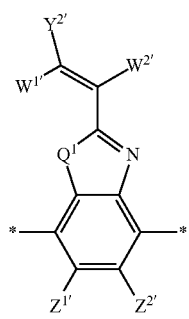 (Ar-10)
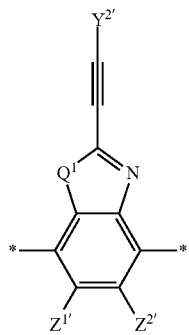 (Ar-11)
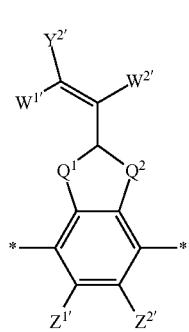 (Ar-12)
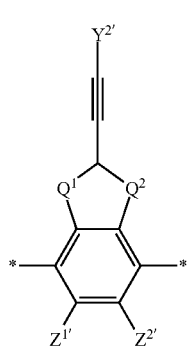 (Ar-13)
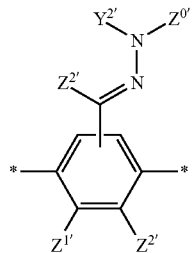 (Ar-14)
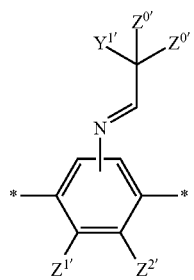 (Ar-15)
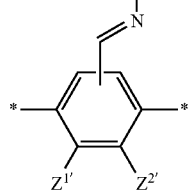 (Ar-16)
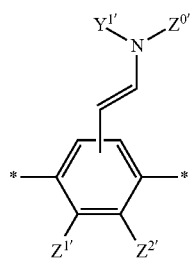 (Ar-17)
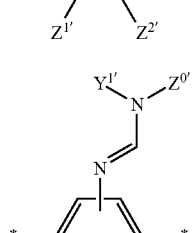 (Ar-18)
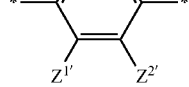 (Ar-19)

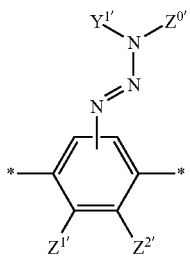
(Ar-20)

In formula (Ar-1) to formula (Ar-20), an portion represents a connection part, $Z^{0'}$, $Z^{1'}$, and $Z^{2'}$, each independently, represent a hydrogen atom, a halogen atom, an alkyl group having 1 to 6 carbon atoms, a cyano group, a nitro group, an alkylsulfinyl group having 1 to 6 carbon atoms, an alkylsulfonyl group having 1 to 6 carbon atoms, a carboxyl group, a fluoroalkyl group having 1 to 6 carbon atoms, an alkoxy group having 1 to 6 carbon atoms, an alkylthio group having 1 to carbon atoms, an N-alkylamino group having 1 to 6 carbon atoms, an N,N-dialkylamino group having 2 to 12 carbon atoms, an N-alkylsulfamoyl group having 1 to 6 carbon atoms, or an N,N-dialkylsulfamoyl group having 2 to 12 carbon atoms.

$Q^1$, $Q^2$, and $Q^3$, each independently, represent —$CR^5R^6$—, —S—, —$NR^7$—, —CO—, or —O—.

$R^5$, $R^6$, and $R^7$, each independently, represent a hydrogen atom or an alkyl group having 1 to 4 carbon atoms.

$Y^{1'}$, $Y^{2'}$, and $Y^{3'}$, each independently, represent an optionally substituted aromatic hydrocarbon group or an aromatic heterocyclic group.

$W^{1'}$ and $W^{2'}$, each independently, represent a hydrogen atom, a cyano group, a methyl group, or a halogen atom.

m represents an integer of 0 to 6.

Examples of the halogen atom include a fluorine atom, a chlorine atom, a bromine atom, and an iodine atom, and the halogen atom is preferably a fluorine atom, a chlorine atom, or a bromine atom.

Examples of the alkyl group having 1 to 6 carbon atoms include a methyl group, an ethyl group, a propyl group, an isopropyl group, a butyl group, an isobutyl group, a sec-butyl group, a tert-butyl group, a pentyl group, and a hexyl group, and the alkyl group having 1 to 6 carbon atoms is preferably an alkyl group having 1 to 4 carbon atoms, more preferably an alkyl group having 1 carbon atom and an alkyl group having 2 carbon atoms, particularly preferably a methyl group.

Examples of the alkylsulfinyl group having 1 to 6 carbon atoms include a methylsulfinyl group, an ethylsulfinyl group, a propylsulfinyl group, an isopropylsulfinyl group, a butylsulfinyl group, an isobutylsulfinyl group, a sec-butylsulfinyl group, a tert-butylsulfinyl group, a pentylsulfinyl group, and a hexyl sulfinyl group, and the alkylsulfinyl group having 1 to 6 carbon atoms is preferably an alkylsulfinyl group having 1 to 4 carbon atoms, more preferably an alkylsulfinyl group having 1 carbon atom and an alkylsulfinyl group having 2 carbon atoms, particularly preferably a methylsulfinyl group.

Examples of the alkylsulfonyl group having 1 to 6 carbon atoms include a methylsulfonyl group, an ethylsulfonyl group, a propylsulfonyl group, an isopropylsulfonyl group, a butylsulfonyl group, an isobutylsulfonyl group, a sec-butylsulfonyl group, a tert-butylsulfonyl group, a pentylsulfonyl group, and a hexylsulfonyl group, and the alkylsulfonyl group having 1 to 6 carbon atoms is preferably an alkylsulfonyl group having 1 to 4 carbon atoms, more preferably an alkylsulfonyl group having 1 carbon atom and an alkylsulfonyl group having 2 carbon atoms, particularly preferably a methylsulfonyl group.

Examples of the fluoroalkyl group having 1 to 6 carbon atoms include a fluoromethyl group, a trifluoromethyl group, a fluoroethyl group, a pentafluoroethyl group, a heptafluoropropyl group, and a nonafluorobutyl group, and the fluoroalkyl group having 1 to 6 carbon atoms is preferably a fluoroalkyl group having 1 to 4 carbon atoms, more preferably a fluoroalkyl group having 1 carbon atom and a fluoroalkyl group having 2 carbon atoms, particularly preferably a trifluoromethyl group.

Examples of the alkoxy group having 1 to 6 carbon atoms include a methoxy group, an ethoxy group, a propoxy group, an isopropoxy group, a butoxy group, an isobutoxy group, a sec-butoxy group, a tert-butoxy group, a pentyloxy group, and a hexyloxy group, and the alkoxy group having 1 to 6 carbon atoms is preferably an alkoxy group having 1 to 4 carbon atoms, more preferably an alkoxy group having 1 carbon atom and an alkoxy group having 2 carbon atoms, particularly preferably a methoxy group.

Examples of the alkylthio group having 1 to 6 carbon atoms include a methylthio group, an ethylthio group, a propylthio group, an isopropylthio group, a butylthio group, an isobutylthio group, a sec-butylthio group, a tert-butylthio group, pentylthio group, and a hexylthio group, and the alkylthio group having 1 to 6 carbon atoms is preferably an alkylthio group having 1 to 4 carbon atoms, more preferably an alkylthio group having 1 carbon atom and an alkylthio group having 2 carbon atoms, particularly preferably a methylthio group.

Examples of the N-alkylamino group having 1 to 6 carbon atoms include an N-methylamino group, an N-ethylamino group, an N-propylamino group, an N-isopropylamino group, an N-butylamino group, an N-isobutylamino group, an N-sec-butylamino group, an N-tert-butylamino group, and an N-pentylamino group, an N-hexylamino group, and the N-alkylamino group having 1 to 6 carbon atoms is preferably an N-alkylamino group having 1 to 4 carbon atoms, more preferably an N-alkylamino group having 1 carbon atom and an N-alkylamino group having 2 carbon atoms, particularly preferably an N-methylamino group.

Examples of the N,N-dialkylamino group having 2 to 12 carbon atoms include an N,N-dimethylamino group, an N-methyl-N-ethylamino group, an N,N-diethylamino group, an N,N-dipropylamino group, an N,N-diisopropylamino group, an N,N-dibutylamino group, an N,N-diisobutylamino group, an N,N-dipentylamino group, and an N,N-dihexylamino group, and the N,N-dialkylamino group having 2 to 12 carbon atoms is preferably an N,N-dialkylamino group having 2 to 8 carbon atoms, more preferably an N,N-dialkylamino group having 2 to 4 carbon atoms, particularly preferably an N,N-dimethylamino group.

Examples of the N-alkylsulfamoyl group having 1 to 6 carbon atoms include an N-methylsulfamoyl group, an N-ethylsulfamoyl group, an N-propylsulfamoyl group, an N-isopropylsulfamoyl group, an N-butylsulfamoyl group, an N-isobutylsulfamoyl group, an N-sec-butylsulfamoyl group, an N-tert-butylsulfamoyl group, an N-pentylsulfamoyl group, and an N-hexylsulfamoyl group, and the N-alkylsulfamoyl group having 1 to 6 carbon atoms is preferably an N-alkylsulfamoyl group having 1 to 4 carbon atoms, more preferably an N-alkylsulfamoyl group having 1 carbon atom and an N-alkylsulfamoyl group having 2 carbon atoms, particularly preferably an N-methylsulfamoyl group.

Examples of the N,N-dialkylsulfamoyl group having 2 to 12 carbon atoms include an N,N-dimethylsulfamoyl group, an N-methyl-N-ethylsulfamoyl group, an N,N-diethylsulfamoyl group, an N,N-dipropylsulfamoyl group, an N,N-diisopropylsulfamoyl group, an N,N-dibutylsulfamoyl group, an N,N-diisobutylsulfamoyl group, an N,N-dipentylsulfamoyl group, and an N,N-dihexylsulfamoyl group, and the N,N-dialkylsulfamoyl group having 2 to 12 carbon atoms is preferably an N,N-dialkylsulfamoyl group having 2 to 8 carbon atoms, more preferably an N,N-dialkylsulfamoyl group having 2 to 4 carbon atoms, particularly preferably an N,N-dimethylsulfamoyl group.

$Z^{0'}$, $Z^{1'}$, and $Z^{2'}$, each independently, are preferably a hydrogen atom, a halogen atom, a methyl group, a cyano group, a nitro group, a carboxyl group, a methylsulfonyl group, a trifluoromethyl group, a methoxy group, a methylthio group, an N-methylamino group, an N,N-dimethylamino group, an N-methylsulfamoyl group, or an N,N-dimethylsulfamoyl group.

Examples of the alkyl group having 1 to 4 carbon atoms in $R^5$, $R^6$, and $R^7$ include a methyl group, an ethyl group, a propyl group, an isopropyl group, a butyl group, an isobutyl group, and a tert-butyl group, and the alkyl group having 1 to 4 carbon atoms is preferably an alkyl group having 1 carbon atom and an alkyl group having 2 carbon atoms, more preferably a methyl group.

$Q^1$ and $Q^2$, each independently, are preferably —S—, —CO—, —NH—, and —N(CH$_3$)—, and $Q^3$ is preferably —S— and —CO—.

Examples of the aromatic hydrocarbon group in $Y^{1'}$, $Y^{2'}$, and $Y^{3'}$ include an aromatic hydrocarbon group having 6 to 20 carbon atoms such as a phenyl group, a naphtyl group, an anthryl group, a phenanthryl group, and a biphenyl group, and the aromatic hydrocarbon group is preferably a phenyl group and a naphtyl group, more preferably a phenyl group. Examples of the aromatic heterocyclic group include an aromatic heterocyclic group having 4 to 20 carbon atoms, which contains at least one heteroatom such as a nitrogen atom, an oxygen atom, a sulfur atom, and the like such as a furyl group, a pyrrolyl group, a thienyl group, a pyridinyl group, a thiazolyl group, a benzothiazolyl group. Among others, a furyl group, a pyrrolyl group, a thienyl group, a pyridinyl group, a thiazolyl group, and a benzothiazolyl group are preferred.

Such an aromatic hydrocarbon group and an aromatic heterocyclic group can have at least one substituent. Examples of the substituent include a halogen atom, an alkyl group having 1 to 6 carbon atoms, a cyano group, a nitro group, an alkylsulfinyl group having 1 to 6 carbon atoms, an alkylsulfonyl group having 1 to 6 carbon atoms, a carboxyl group, a fluoroalkyl group having 1 to 6 carbon atoms, an alkoxy group having 1 to 6 carbon atoms, an alkylthio group having 1 to 6 carbon atoms, an N-alkylamino group having 1 to 6 carbon atoms, an N,N-dialkylamino group having 2 to 12 carbon atoms, an N-alkylsulfamoyl group having 1 to 6 carbon atoms, an N,N-dialkylsulfamoyl group having 2 to 12 carbon atoms, and the substituent is preferably a halogen atom, an alkyl group having 1 carbon atom and an alkyl group having 2 carbon atoms, a cyano group, a nitro group, an alkylsulfonyl group having 1 carbon atom and an alkylsulfonyl group having 2 carbon atoms, a fluoroalkyl group having 1 carbon atom and a fluoroalkyl group having 2 carbon atoms, an alkoxy group having 1 carbon atom and an alkoxy group having 2 carbon atoms, an alkylthio group having 1 carbon atom and an alkylthio group having 2 carbon atoms, an N-alkylamino group having 1 carbon atom and an N-alkylamino group having 2 carbon atoms, an N,N-dialkylamino group having 2 to 4 carbon atoms, and an alkylsulfamoyl group having 1 carbon atom and an alkylsulfamoyl group having 2 carbon atoms.

Examples of the halogen atom, the alkyl group having 1 to 6 carbon atoms, the cyano group, the nitro group, the alkylsulfinyl group having 1 to 6 carbon atoms, the alkylsulfonyl group having 1 to 6 carbon atoms, the carboxyl group, the fluoroalkyl group having 1 to 6 carbon atoms, the alkoxy group having 1 to 6 carbon atoms, the alkylthio group having 1 to 6 carbon atoms, the N-alkylamino group having 1 to 6 carbon atoms, the N,N-dialkylamino group having 2 to 12 carbon atoms, the N-alkylsulfamoyl group having 1 to 6 carbon atoms, and the N,N-dialkylsulfamoyl group having 2 to 12 carbon atoms include the same ones as exemplified above.

From the view point of stability of a molecule, among formulae (Ar-14) to (Ar-20), formula (Ar-6) and formula (Ar-7) are preferable.

In formulae (Ar-14) to (Ar-20), $Y^{1'}$ can form an aromatic heterocyclic group with a nitrogen atom to which $Y^{1'}$ is bonded and $Z^{0'}$. Examples of the aromatic heterocyclic group include a pyrrole ring, an imidazole ring, a pyridine ring, a pyrimidine ring, an indole ring, a quinoline ring, an isoquinoline ring, a purine ring, a pyrrolidine ring, and a piperidine ring. The aromatic heterocyclic group can have a substituent. Further, $Y^{1'}$, with a nitrogen atom to which $Y^{1'}$ is bonded and $Z^{0'}$, can be an optionally substituted polycyclic aromatic hydrocarbon group or an optionally substituted polycyclic aromatic heterocyclic group as described below.

$Y^{1'}$, $Y^{2'}$, and $Y^{3'}$, each independently, can be an optionally substituted polycyclic aromatic hydrocarbon group or an optionally substituted polycyclic aromatic heterocyclic group. The polycyclic aromatic hydrocarbon group refers to a condensed polycyclic aromatic hydrocarbon group or a group derived from an aromatic ring assembly. The polycyclic aromatic heterocyclic group refers to a condensed polycyclic aromatic heterocyclic group or a group derived from an aromatic ring assembly. For example, $Y^{1'}$, $Y^{2'}$, and $Y^{3'}$, each independently, are preferably any group of the following formula ($Y^1$-1) to formula ($Y^1$-7), more preferably any group of formula ($Y^1$-1) or formula ($Y^1$-4).

[Chemical Formula 5]

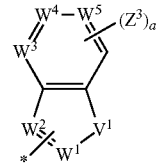

($Y^1$-1)

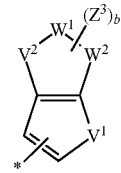

($Y^1$-2)

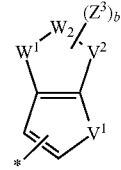

($Y^1$-3)

-continued

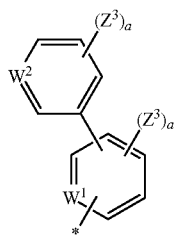 (Y¹-4)

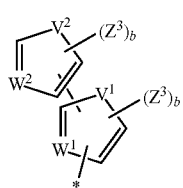 (Y¹-5)

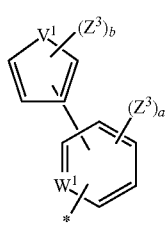 (Y¹-6)

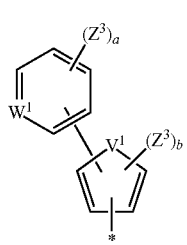 (Y¹-7)

In the formula (Y¹-1) to formula (Y¹-7) given above, an * portion represents a connection part, and $Z^3$, each independently, represents a halogen atom, an alkyl group having 1 to 6 carbon atoms, a cyano group, a nitro group, a nitroxide group, a sulfone group, a sulfoxide group, a carboxyl group, a fluoroalkyl group having 1 to 6 carbon atoms, an alkoxy group having 1 to 6 carbon atoms, a thioalkyl group having 1 to 6 carbon atoms, an N,N-dialkylamino group having 2 to 8 carbon atoms, or an N-alkylamino group having 1 to 4 carbon atoms.

$V^1$ and $V^2$, each independently, represent —CO—, —S—, —NR$^8$—, —O—, —Se—, or —SO$_2$—.

$W^1$ to $W^5$, each independently, represent —C= or —N=.

With the proviso, however, that at least one of $V^1$, $V^2$, and $W^1$ to $W^5$ represents a group containing S, N, O, or Se.

$R^8$ represents a hydrogen atom or an alkyl group having 1 to 4 carbon atoms.

a, each independently, represents an integer of 0 to 3.

b, each independently, represents an integer of 0 to 2.

Any of groups represented by formula (Y¹-1) to formula (Y¹-7) is preferably any of groups represented by the following formula (Y²-1) to formula (Y²-16), more preferably any of groups represented by the following formula (Y³-1) to formula (Y³-6), particularly preferably a group represented by formula (Y³-1) or formula (Y³-3). Then, an * portion represents a connection part.

[Chemical Formula 6]

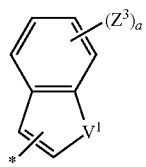 (Y²-1)

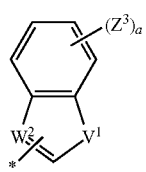 (Y²-2)

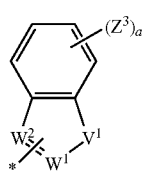 (Y²-3)

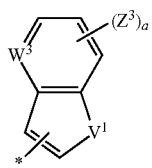 (Y²-4)

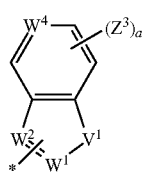 (Y²-5)

(Y²-6)

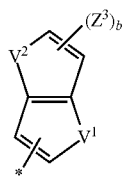 (Y²-7)

 (Y²-8)

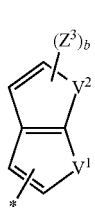

(Y²-9) 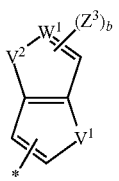
(Y²-10) 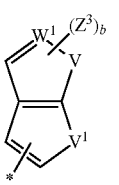
(Y²-11) 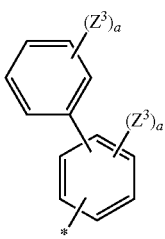
(Y²-12) 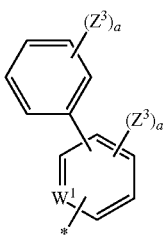
(Y²-13) 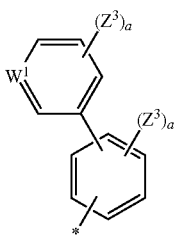
(Y²-14) 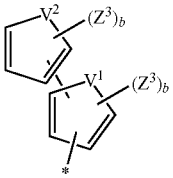
(Y²-15) 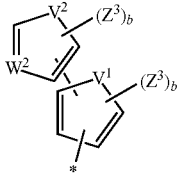
(Y²-16) 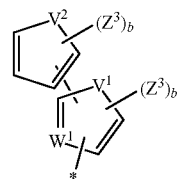
In formula (Y²-1) to formula (Y²-16), $Z^3$, a, b, $V^1$, $V^2$, and $W^1$ to $W^5$ represent the same meaning as described above.
[Chemical Formula 7]
(Y³-1) 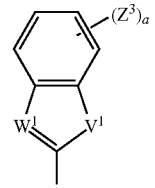
(Y³-2) 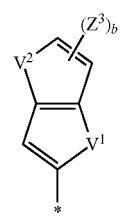
(Y³-3) 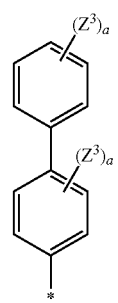
(Y³-4) 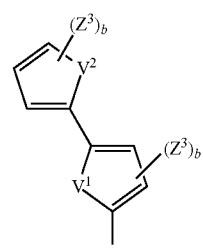
(Y³-5) 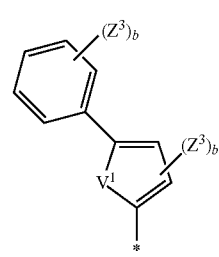

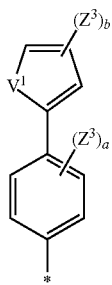

(Y³-6)

[Chemical Formula 8]

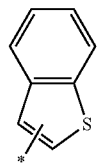

(ar-001)

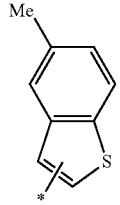

(ar-002)

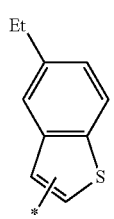

(ar-003)

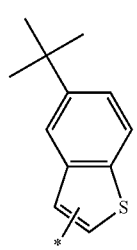

(ar-004)

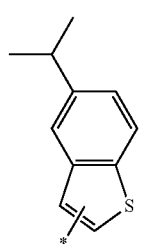

(ar-005)

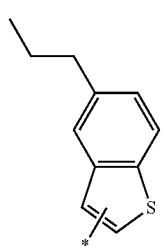

(ar-006)

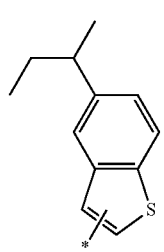

(ar-007)

In formula (Y³-1) to formula (Y³-6), $Z^3$, a, b, $V^1$, $V^2$, and $W^1$ represent the same meaning as described above.

Examples of $Z^3$ include a halogen atom, an alkyl group having 1 to 6 carbon atoms, a cyano group, a nitro group, an alkylsulfinyl group having 1 to 6 carbon atoms, an alkylsulfonyl group having 1 to 6 carbon atoms, a carboxyl group, a fluoroalkyl group having 1 to 6 carbon atoms, an alkoxy group having 1 to 6 carbon atoms, an alkylthio group having 1 to 6 carbon atoms, an N-alkylamino group having 1 to 6 carbon atoms, an N,N-dialkylamino group having 2 to 12 carbon atoms, an N-alkylsulfamoyl group having 1 to 6 carbon atoms, and an N,N-dialkylsulfamoyl group having 2 to 12 carbon atoms. Among others, $Z^3$ is preferably a halogen atom, a methyl group, an ethyl group, an isopropyl group, a sec-butyl group, a cyano group, a nitro group, a sulfone group, a nitroxide group, a carboxyl group, a trifluoromethyl group, a methoxy group, a thiomethyl group, an N,N-dimethylamino group, and an N-methylamino group, more preferably a halogen atom, a methyl group, an ethyl group, an isopropyl group, a sec-butyl group, a cyano group, a nitro group, and a trifluoromethyl group, particularly preferably a methyl group, an ethyl group, an isopropyl group, a sec-butyl group, a pentyl group, and a hexyl group.

Examples of a halogen atom, an alkyl group having 1 to 6 carbon atoms, an alkylsulfinyl group having 1 to 6 carbon atoms, an alkylsulfonyl group having 1 to 6 carbon atoms, a fluoroalkyl group having 1 to 6 carbon atoms, an alkoxy group having 1 to 6 carbon atoms, an alkylthio group having 1 to 6 carbon atoms, an N-alkylamino group having 1 to 6 carbon atoms, an N,N-dialkylamino group having 2 to 12 carbon atoms, an N-alkylsulfamoyl group having 1 to 6 carbon atoms, and an N,N-dialkylsulfamoyl group having 2 to 12 carbon atoms include the same ones as exemplified above.

$V^1$ and $V^2$, each independently, are preferably —S—, —NR⁸—, or —O—.

$W^1$ to $W^5$, each independently, are preferably —C═ or —N═.

At least one of $V^1$, $V^2$, and $W^1$ to $W^5$ preferably represents a group containing S, N, or O.

a is preferably 0 or 1. b is preferably 0.

Specific examples of $Y^{1'}$ to $Y^{3'}$ include groups represented by the following formula (ar-1) to formula (ar-846). Then, an * portion represents a connection part.

[Chemical Formula 9]
 (ar-008)
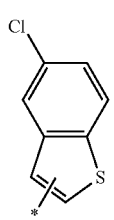 (ar-009)
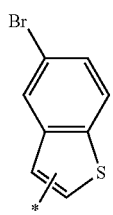 (ar-010)
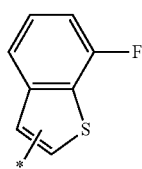 (ar-011)
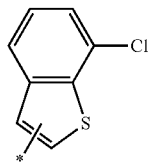 (ar-012)
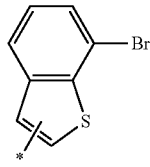 (ar-013)
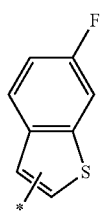 (ar-014)
[Chemical Formula 10]
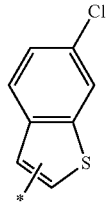 (ar-015)
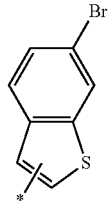 (ar-016)
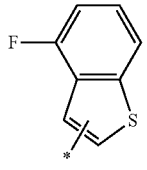 (ar-017)
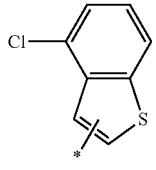 (ar-018)
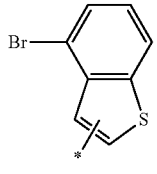 (ar-019)
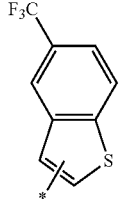 (ar-020)
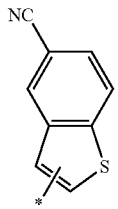 (ar-021)

[Chemical Formula 11]
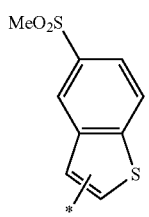 (ar-022)
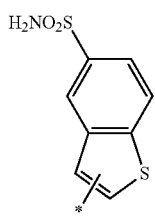 (ar-023)
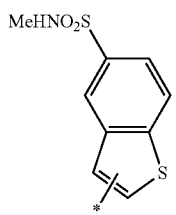 (ar-024)
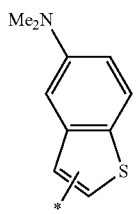 (ar-025)
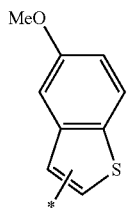 (ar-026)
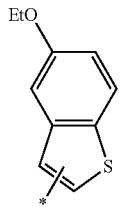 (ar-027)
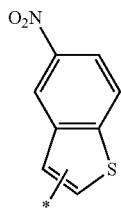 (ar-028)
[Chemical Formula 12]
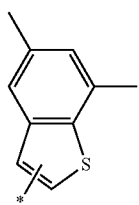 (ar-029)
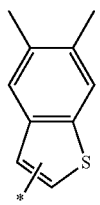 (ar-030)
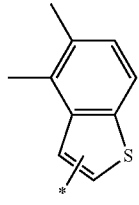 (ar-031)
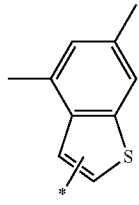 (ar-032)
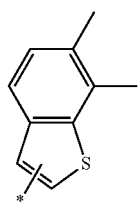 (ar-033)
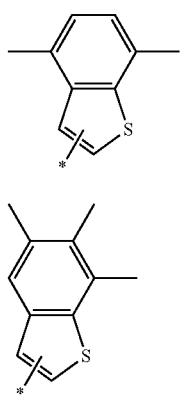 (ar-034)
(ar-035)

[Chemical Formula 13]
(ar-036)
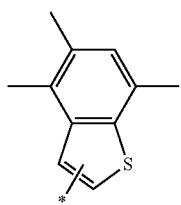
(ar-037)
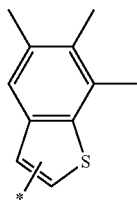
(ar-038)
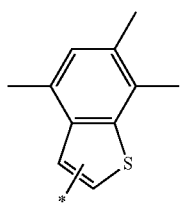
(ar-039)
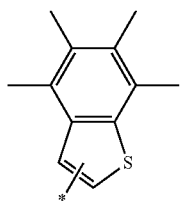
(ar-040)
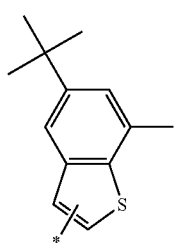
(ar-041)
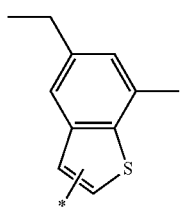
(ar-042)
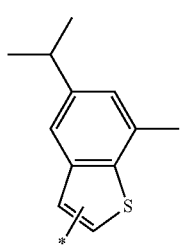
[Chemical Formula 14]
(ar-043)
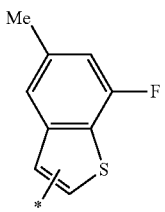
(ar-044)
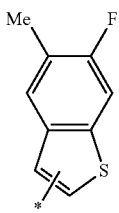
(ar-045)
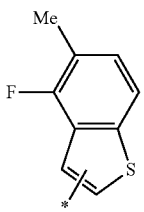
(ar-046)
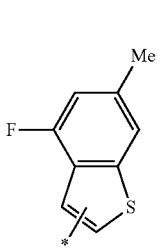
(ar-047)
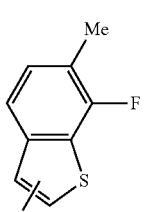
(ar-048)
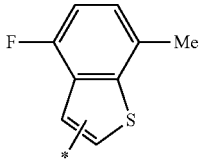
(ar-049)
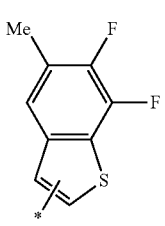

[Chemical Formula 15]
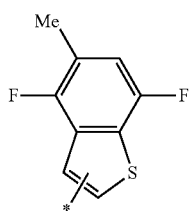
(ar-050)
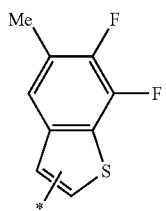
(ar-051)
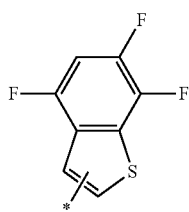
(ar-052)
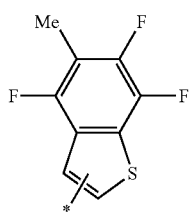
(ar-053)
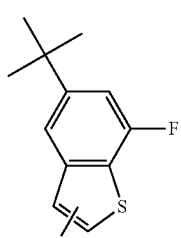
(ar-054)
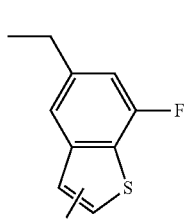
(ar-055)
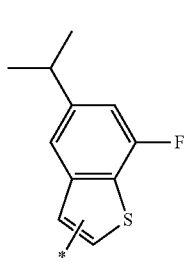
(ar-056)
[Chemical Formula 16]
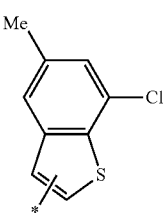
(ar-057)
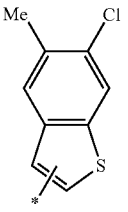
(ar-058)
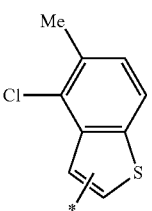
(ar-059)
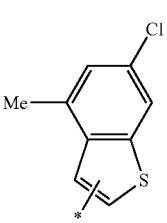
(ar-060)
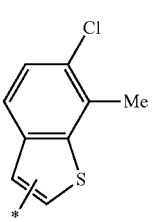
(ar-061)
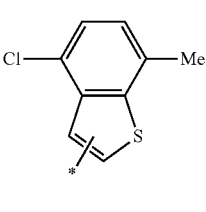
(ar-062)
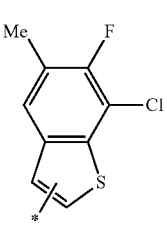
(ar-063)

[Chemical Formula 17]
(ar-064)
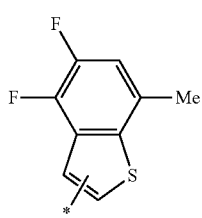
(ar-065)
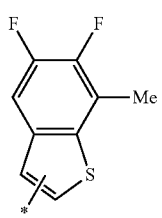
(ar-066)
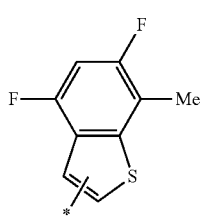
(ar-067)
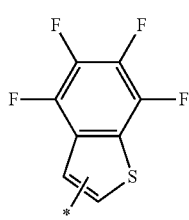
(ar-068)
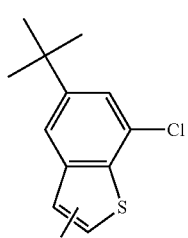
(ar-069)
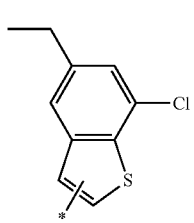
(ar-070)
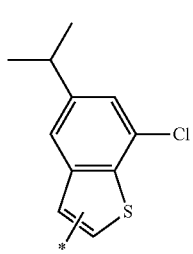
[Chemical Formula 18]
(ar-071)
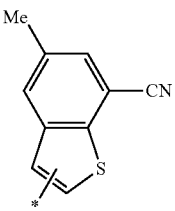
(ar-072)
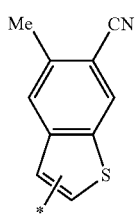
(ar-073)
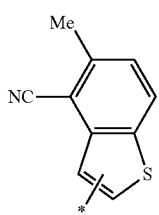
(ar-074)
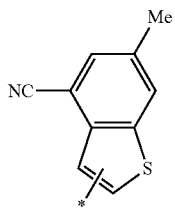
(ar-075)
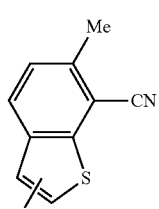
(ar-076)
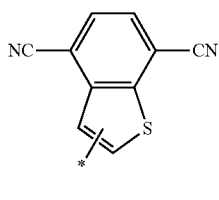
(ar-077)
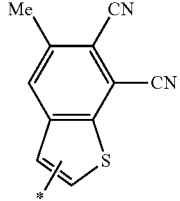

-continued
[Chemical Formula 19]
(ar-078)
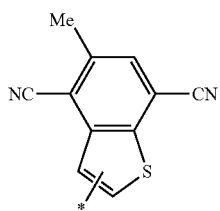
(ar-079)
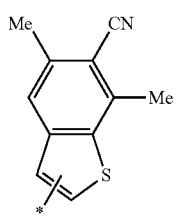
(ar-080)
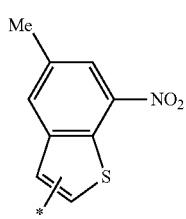
(ar-081)
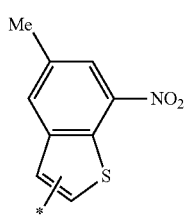
(ar-082)
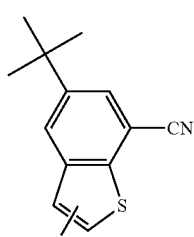
(ar-083)
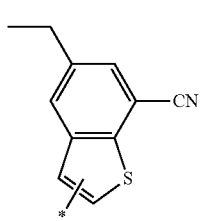
(ar-084)
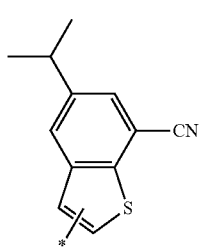
-continued
[Chemical Formula 20]
(ar-085)
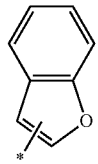
(ar-086)
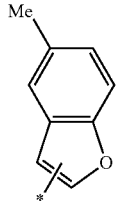
(ar-087)
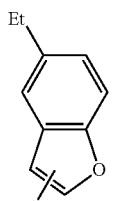
(ar-088)
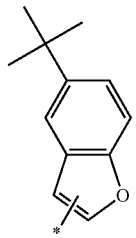
(ar-089)
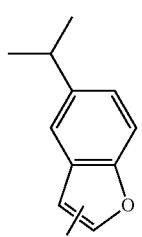
(ar-090)
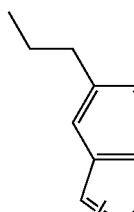
(ar-091)
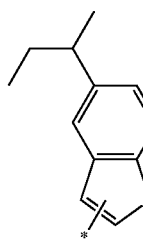

[Chemical Formula 21]
(ar-092)
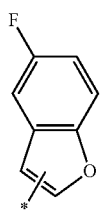
(ar-093)
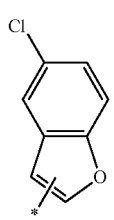
(ar-094)
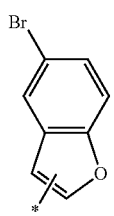
(ar-095)
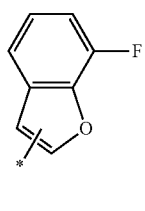
(ar-096)
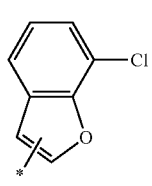
(ar-097)
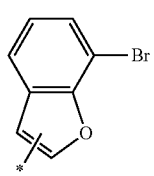
(ar-098)
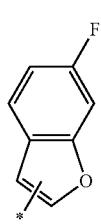
[Chemical Formula 22]
(ar-099)
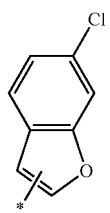
(ar-100)
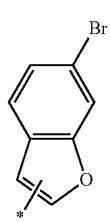
(ar-101)
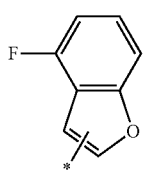
(ar-102)
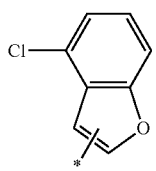
(ar-103)
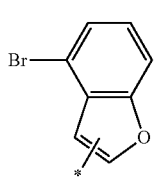
(ar-104)
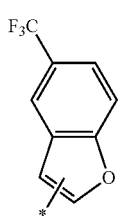
(ar-105)
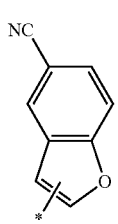

(ar-106) 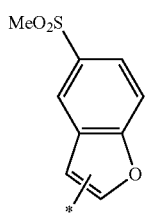
(ar-107) 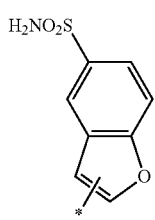
(ar-108) 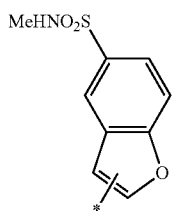
(ar-109) 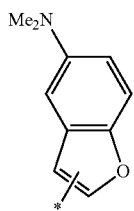
(ar-110) 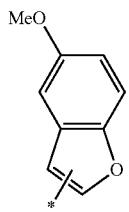
(ar-111) 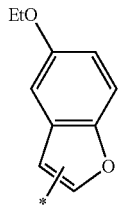
(ar-112) 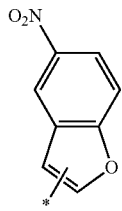
(ar-113) 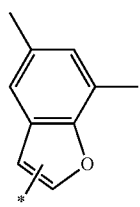
(ar-114) 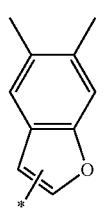
(ar-115) 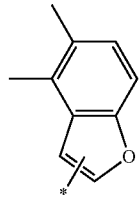
(ar-116) 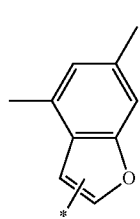
(ar-117) 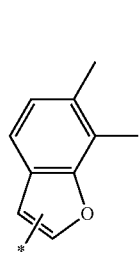
(ar-118) 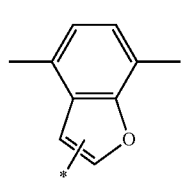
(ar-119) 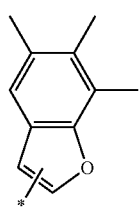

[Chemical Formula 25]
(ar-120) 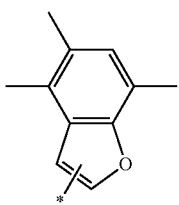
(ar-121) 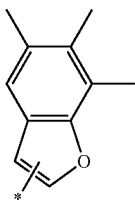
(ar-122) 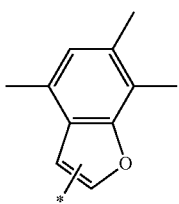
(ar-123) 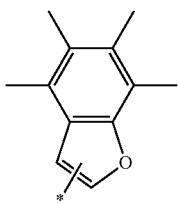
(ar-124) 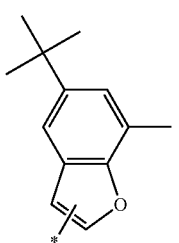
(ar-125) 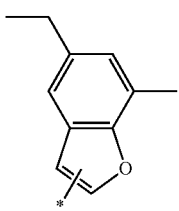
(ar-126) 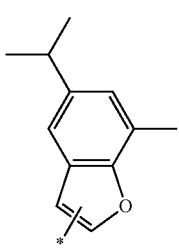
[Chemical Formula 26]
(ar-127) 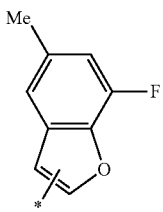
(ar-128) 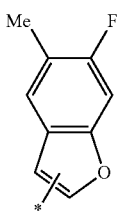
(ar-129) 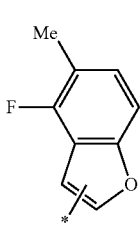
(ar-130) 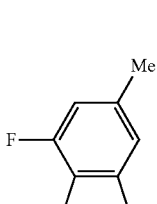
(ar-131) 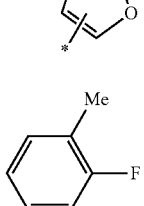
(ar-132) 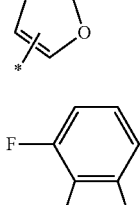
(ar-133) 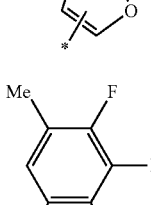
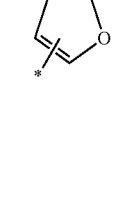

[Chemical Formula 27]
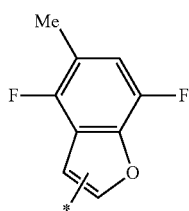 (ar-134)
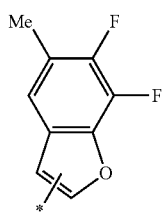 (ar-135)
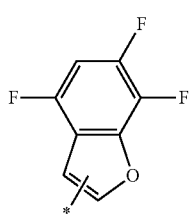 (ar-136)
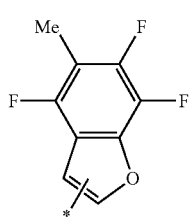 (ar-137)
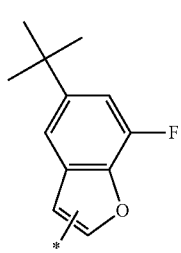 (ar-138)
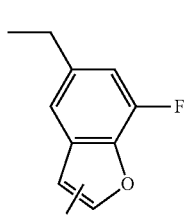 (ar-139)
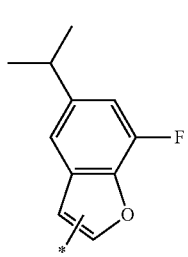 (ar-140)
[Chemical Formula 28]
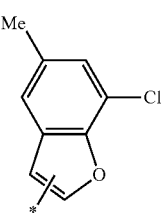 (ar-141)
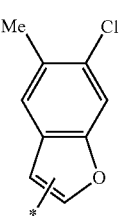 (ar-142)
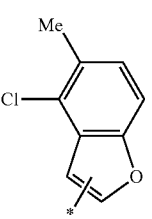 (ar-143)
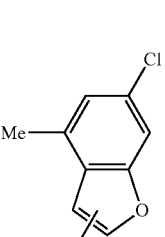 (ar-144)
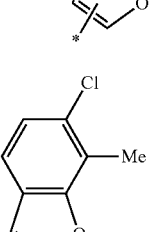 (ar-145)
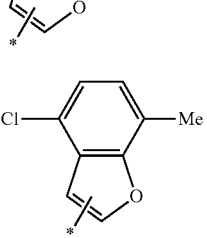 (ar-146)
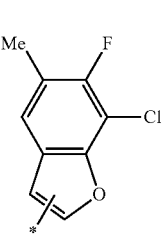 (ar-147)

-continued
[Chemical Formula 29]
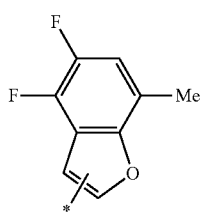 (ar-148)
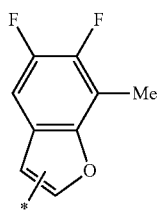 (ar-149)
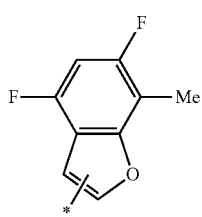 (ar-150)
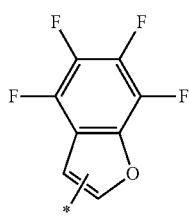 (ar-151)
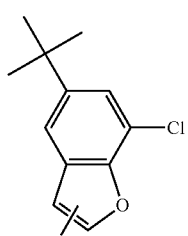 (ar-152)
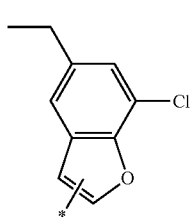 (ar-153)
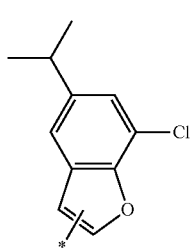 (ar-154)
-continued
[Chemical Formula 30]
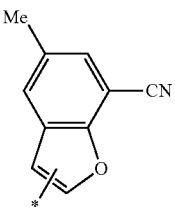 (ar-155)
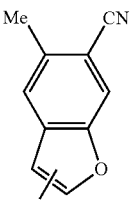 (ar-156)
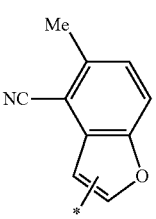 (ar-157)
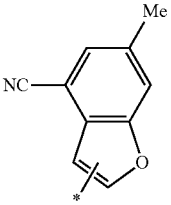 (ar-158)
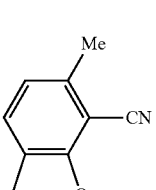 (ar-159)
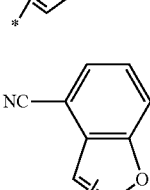 (ar-160)
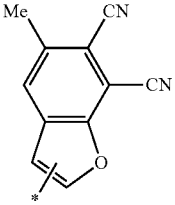 (ar-161)

[Chemical Formula 31]
(ar-163) 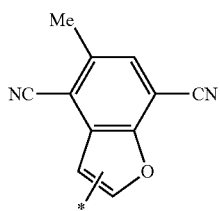
(ar-163) 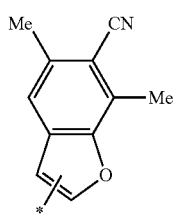
(ar-164) 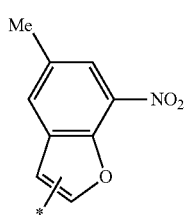
(ar-165) 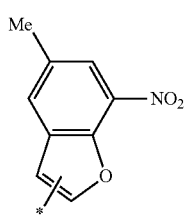
(ar-166) 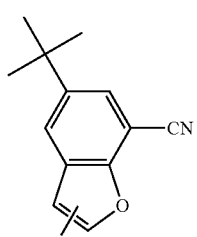
(ar-167) 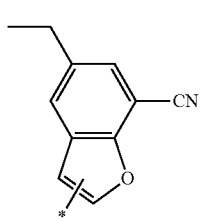
(ar-168) 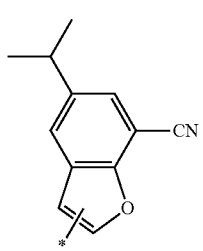
[Chemical Formula 20]
(ar-169) 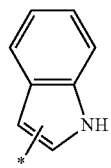
(ar-170) 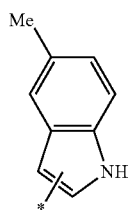
(ar-171) 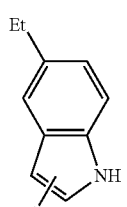
(ar-172) 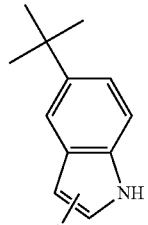
(ar-173) 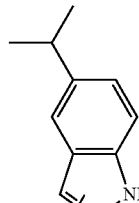
(ar-174) 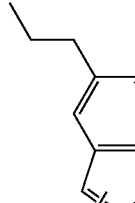
(ar-175) 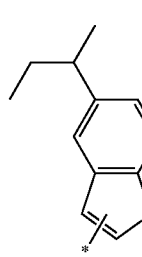

[Chemical Formula 33]
(ar-176)
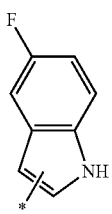
(ar-177)
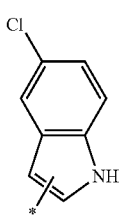
(ar-178)
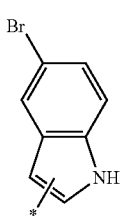
(ar-179)
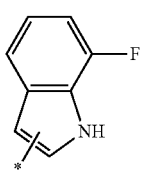
(ar-180)
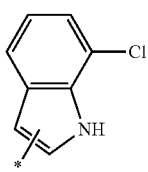
(ar-181)
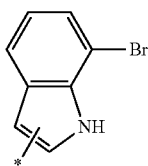
(ar-182)
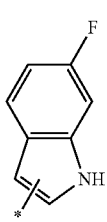
[Chemical Formula 34]
(ar-183)
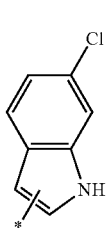
(ar-184)
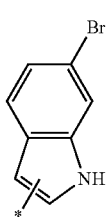
(ar-185)
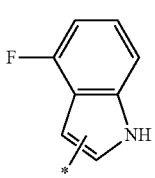
(ar-186)
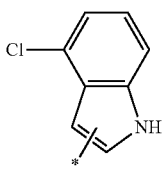
(ar-187)
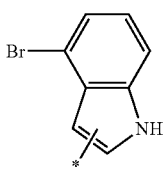
(ar-188)
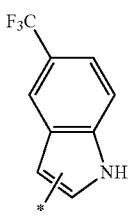
(ar-189)
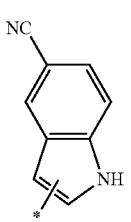

[Chemical Formula 35]
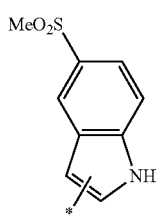 (ar-190)
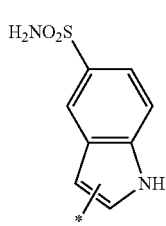 (ar-191)
 (ar-192)
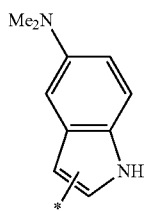 (ar-193)
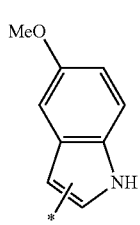 (ar-194)
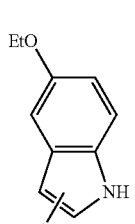 (ar-195)
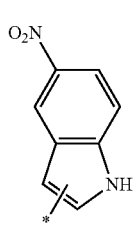 (ar-196)
[Chemical Formula 36]
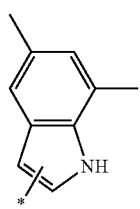 (ar-197)
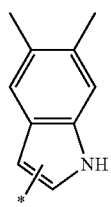 (ar-198)
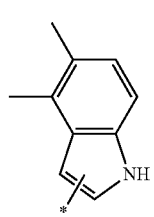 (ar-199)
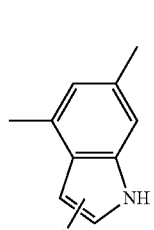 (ar-200)
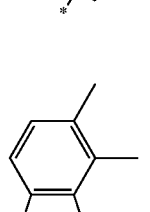 (ar-201)
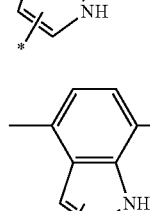 (ar-202)
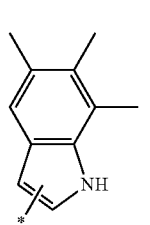 (ar-203)

[Chemical Formula 37]
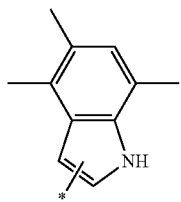 (ar-204)
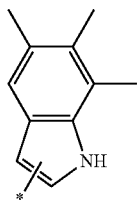 (ar-205)
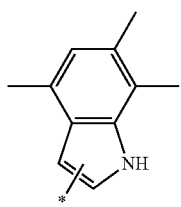 (ar-206)
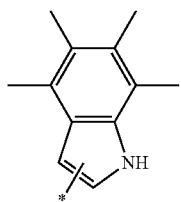 (ar-207)
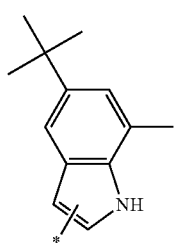 (ar-208)
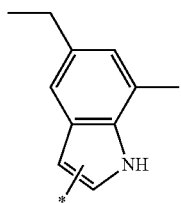 (ar-209)
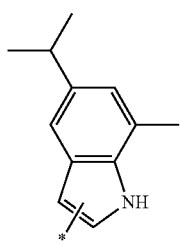 (ar-210)
[Chemical Formula 38]
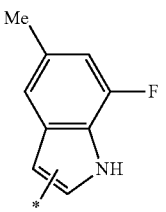 (ar-211)
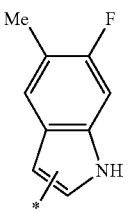 (ar-212)
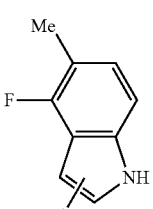 (ar-213)
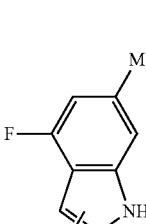 (ar-214)
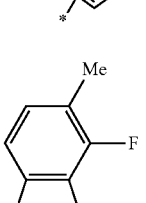 (ar-215)
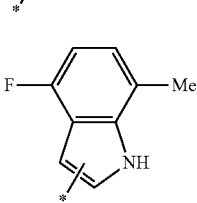 (ar-216)
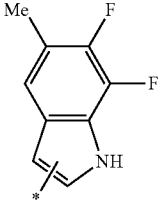 (ar-217)

[Chemical Formula 39]
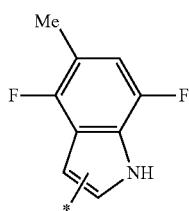 (ar-218)
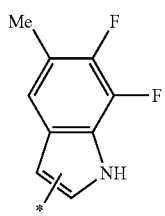 (ar-219)
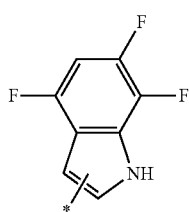 (ar-220)
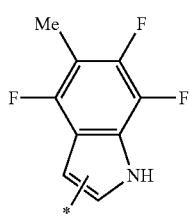 (ar-221)
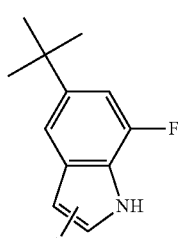 (ar-222)
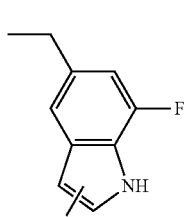 (ar-223)
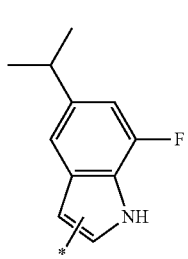 (ar-224)
[Chemical Formula 40]
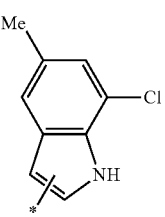 (ar-225)
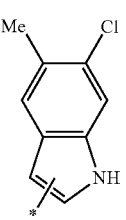 (ar-226)
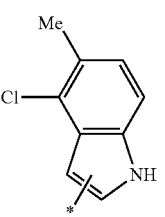 (ar-227)
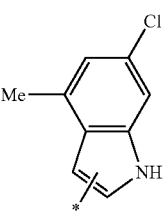 (ar-228)
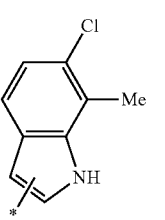 (ar-229)
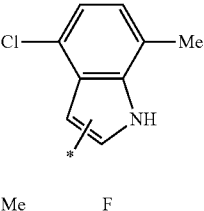 (ar-230)
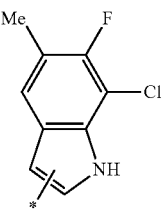 (ar-231)

[Chemical Formula 29]
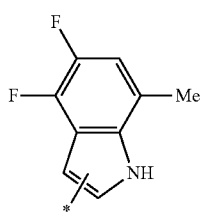 (ar-235)
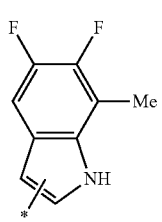 (ar-233)
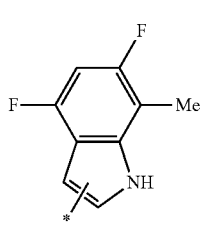 (ar-234)
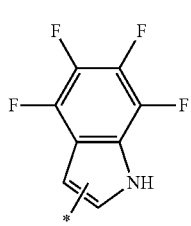 (ar-235)
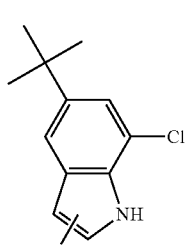 (ar-236)
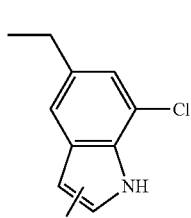 (ar-237)
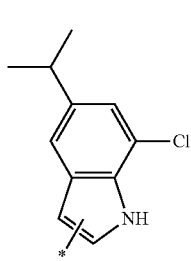 (ar-238)
[Chemical Formula 42]
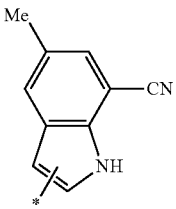 (ar-239)
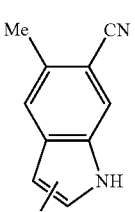 (ar-240)
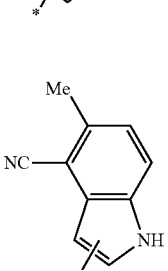 (ar-241)
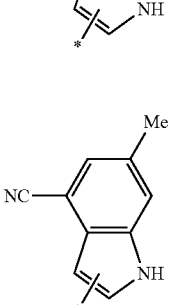 (ar-242)
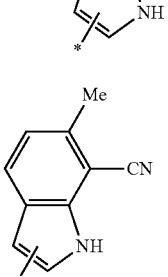 (ar-243)
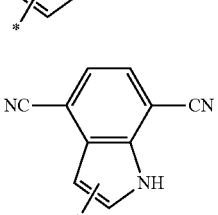 (ar-244)
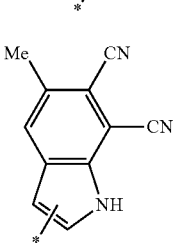 (ar-245)

[Chemical Formula 31]
(ar-246)
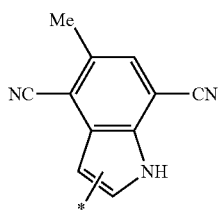
(ar-247)
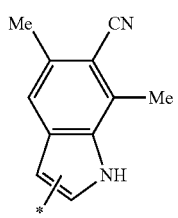
(ar-248)
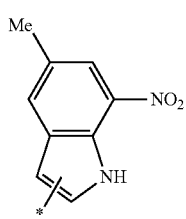
(ar-249)
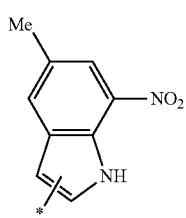
(ar-250)
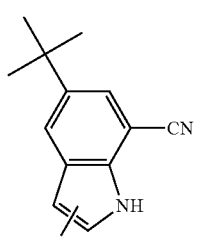
(ar-251)
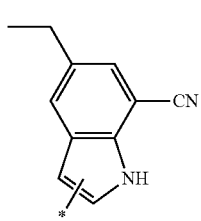
(ar-252)
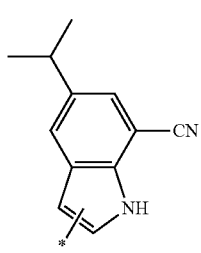
[Chemical Formula 44]
(ar-253)
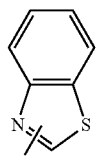
(ar-254)
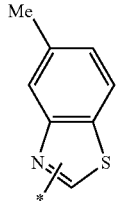
(ar-255)
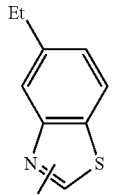
(ar-256)
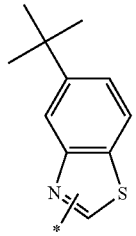
(ar-257)
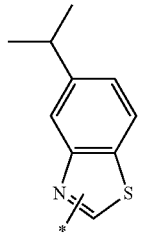
(ar-258)
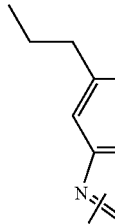
(ar-259)
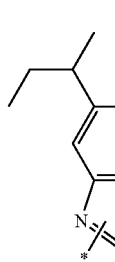

[Chemical Formula 45]
(ar-260) 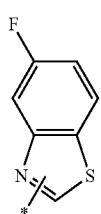
(ar-261) 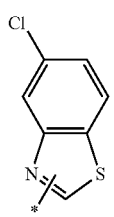
(ar-262) 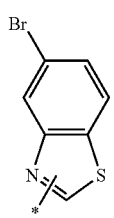
(ar-263) 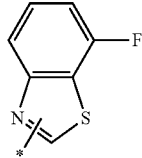
(ar-264) 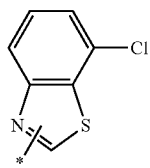
(ar-265) 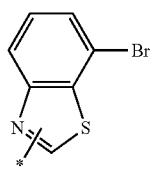
(ar-266) 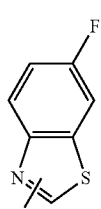
[Chemical Formula 46]
(ar-267) 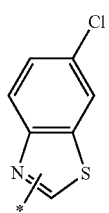
(ar-268) 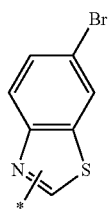
(ar-269) 
(ar-270) 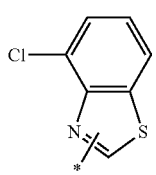
(ar-271) 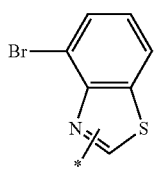
(ar-272) 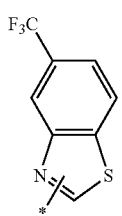
(ar-273) 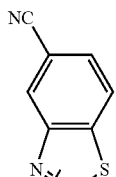
[Chemical Formula 47]
(ar-274) 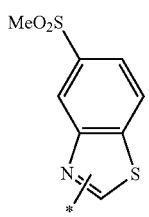

(ar-275) 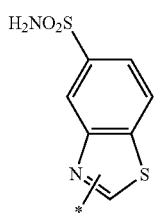
(ar-276) 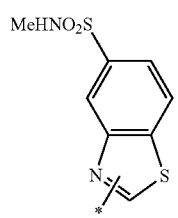
(ar-277) 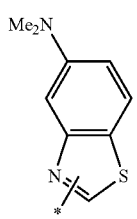
(ar-278) 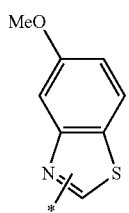
(ar-279) 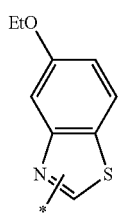
(ar-280) 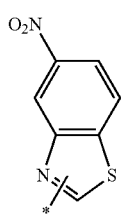
[Chemical Formula 48]
(ar-281) 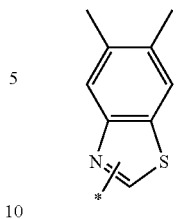
(ar-282) 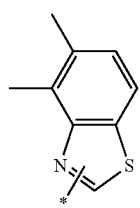
(ar-283) 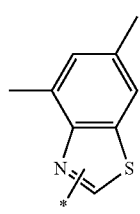
(ar-284) 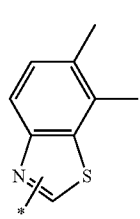
(ar-285) 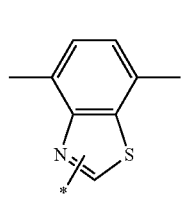
(ar-286) 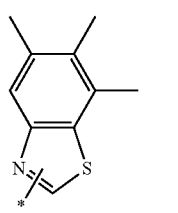
(ar-287) 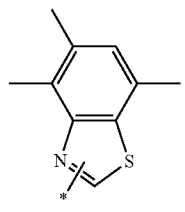
[Chemical Formula 49]
(ar-288) 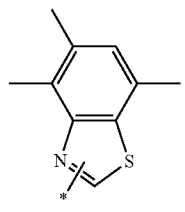

(ar-289) 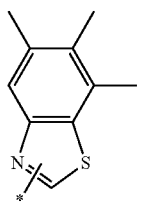
(ar-290) 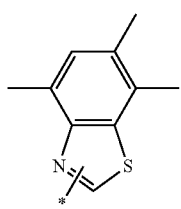
(ar-291) 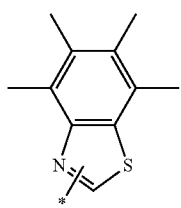
(ar-292) 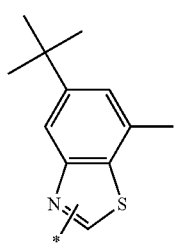
(ar-293) 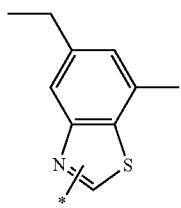
(ar-294) 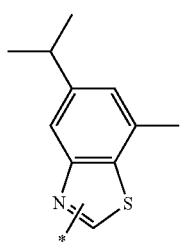
[Chemical Formula 50]
(ar-295) 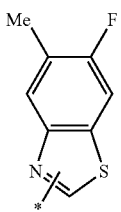
(ar-296) 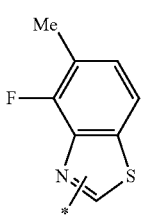
(ar-297)
(ar-298)
(ar-299)
(ar-300)
(ar-301)
[Chemical Formula 39]
(ar-302)

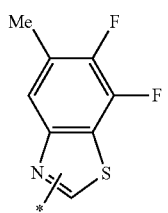 (ar-303)
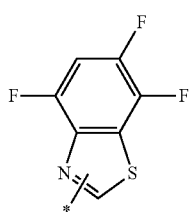 (ar-304)
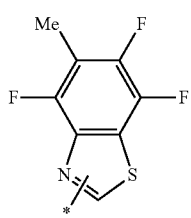 (ar-305)
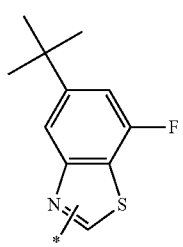 (ar-306)
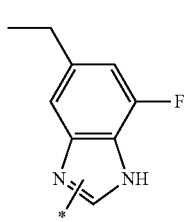 (ar-307)
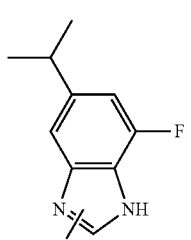 (ar-308)
[Chemical Formula 52]
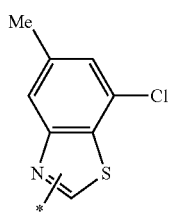 (ar-309)
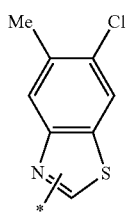 (ar-310)
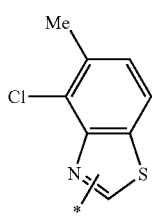 (ar-311)
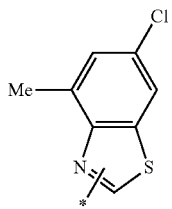 (ar-312)
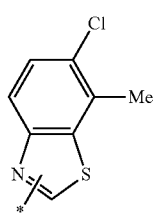 (ar-313)
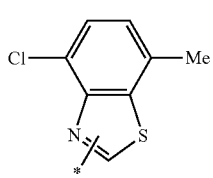 (ar-314)
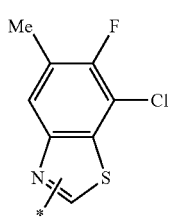 (ar-315)
[Chemical Formula 53]
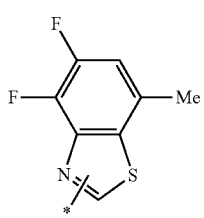 (ar-316)

-continued
(ar-317)
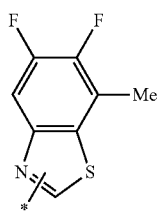
(ar-318)
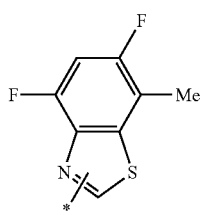
(ar-319)
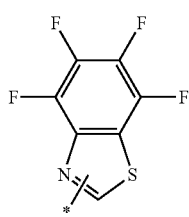
(ar-320)
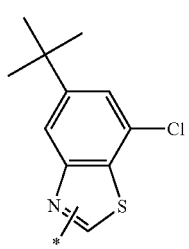
(ar-321)
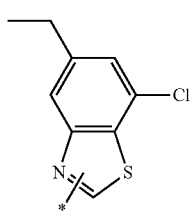
(ar-322)
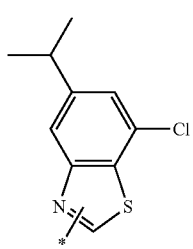
[Chemical Formula 54]
(ar-323)
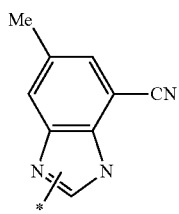
-continued
(ar-324)
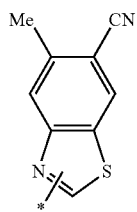
(ar-325)
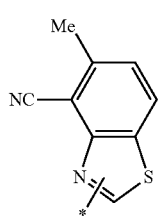
(ar-326)
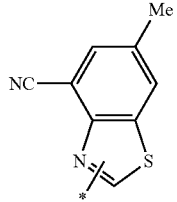
(ar-327)
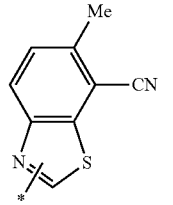
(ar-328)
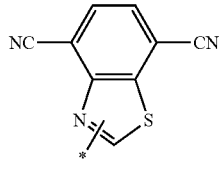
(ar-329)
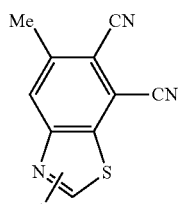
[Chemical Formula 31]
(ar-330)
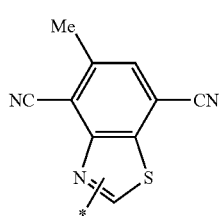

-continued
(ar-331)
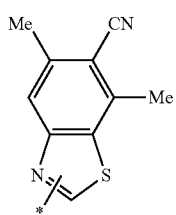
(ar-332)
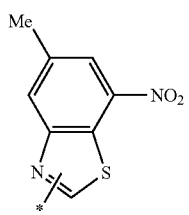
(ar-333)
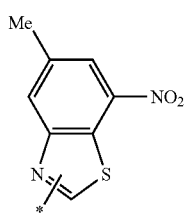
(ar-334)
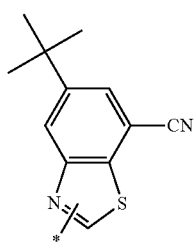
(ar-335)
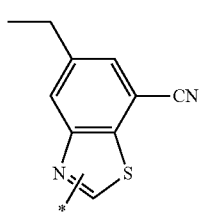
(ar-336)
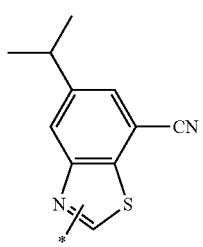
[Chemical Formula 56]
(ar-337)
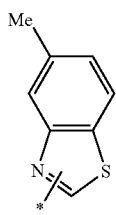
-continued
(ar-338)
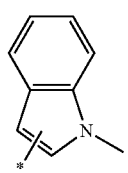
[Chemical Formula 56]
(ar-337)
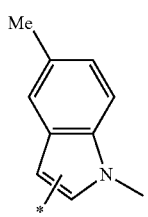
(ar-338)
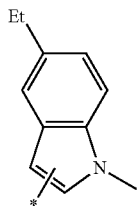
(ar-339)
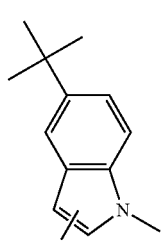
(ar-340)
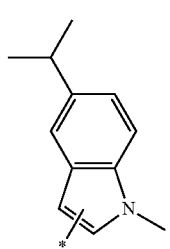
(ar-341)
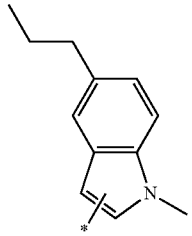
(ar-342)

(ar-343) 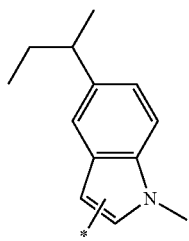
[Chemical Formula 57]
(ar-344) 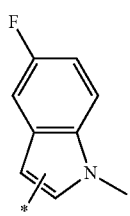
(ar-345) 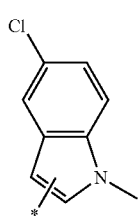
(ar-346) 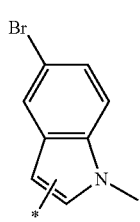
(ar-347) 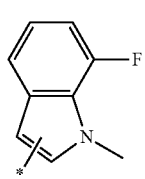
(ar-348) 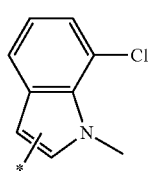
(ar-349) 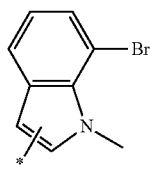
(ar-350) 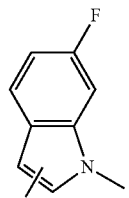
[Chemical Formula 58]
(ar-351) 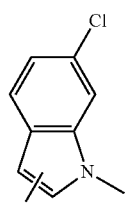
(ar-352) 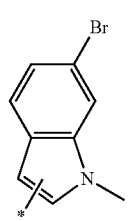
(ar-353) 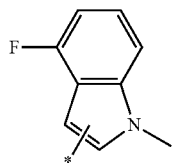
(ar-354) 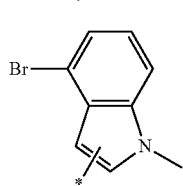
(ar-355) 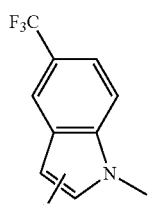
(ar-356) 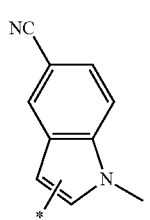
(ar-357)

-continued
[Chemical Formula 59]
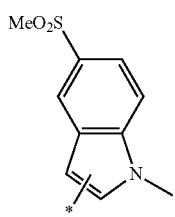 (ar-358)
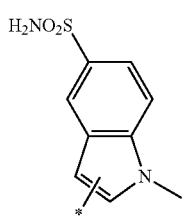 (ar-359)
 (ar-360)
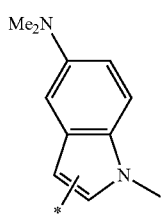 (ar-361)
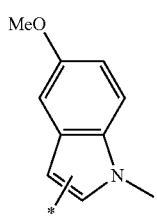 (ar-362)
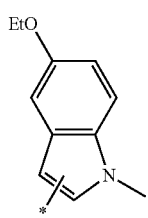 (ar-363)
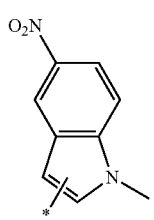 (ar-364)
-continued
[Chemical Formula 60]
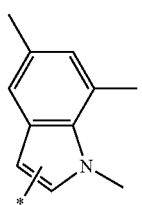 (ar-365)
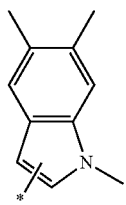 (ar-366)
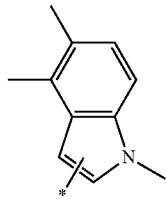 (ar-367)
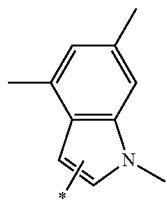 (ar-368)
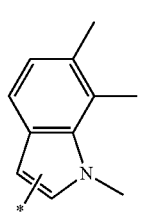 (ar-369)
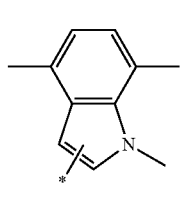 (ar-370)
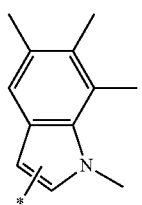 (ar-371)

[Chemical Formula 61]
(ar-372) 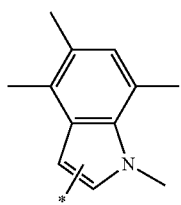
(ar-373) 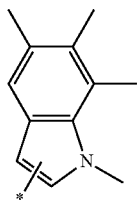
(ar-374) 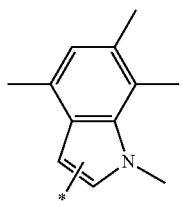
(ar-375) 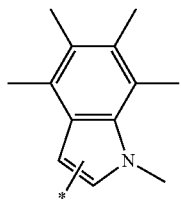
(ar-376) 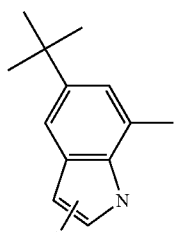
(ar-377) 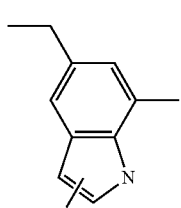
(ar-378) 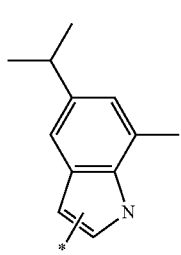
[Chemical Formula 62]
(ar-379) 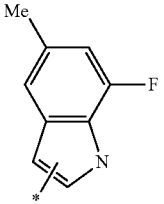
(ar-380) 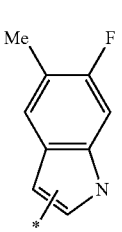
(ar-381) 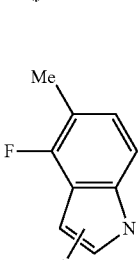
(ar-382) 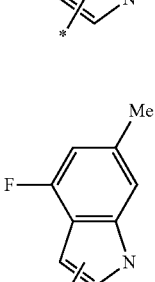
(ar-383) 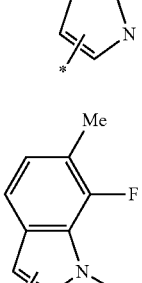
(ar-384) 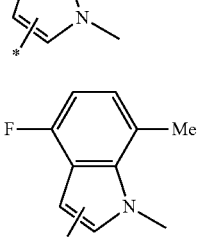
(ar-385) 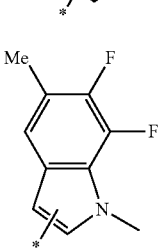

[Chemical Formula 63]
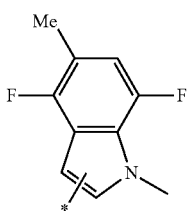 (ar-386)
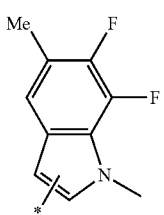 (ar-387)
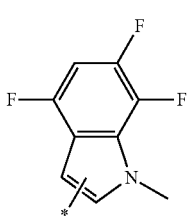 (ar-388)
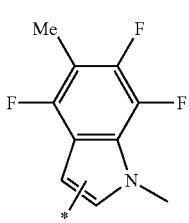 (ar-389)
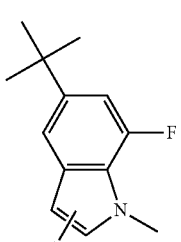 (ar-390)
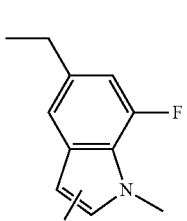 (ar-391)
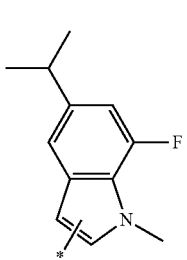 (ar-392)
[Chemical Formula 64]
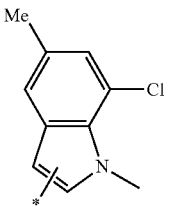 (ar-393)
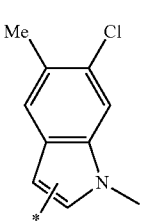 (ar-394)
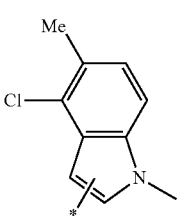 (ar-395)
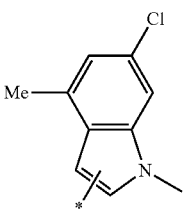 (ar-396)
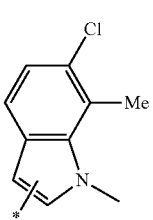 (ar-397)
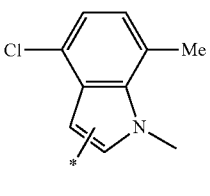 (ar-398)
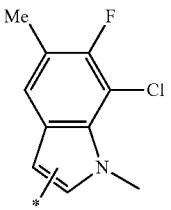 (ar-399)

[Chemical Formula 65]
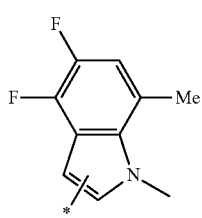 (ar-400)
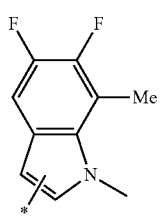 (ar-401)
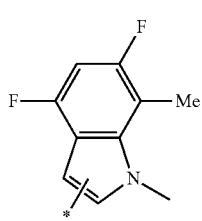 (ar-402)
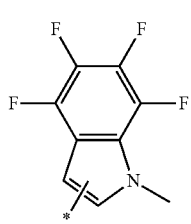 (ar-403)
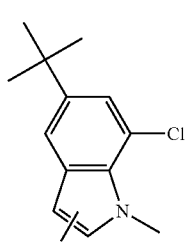 (ar-404)
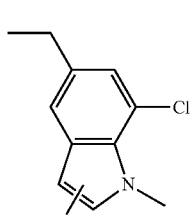 (ar-405)
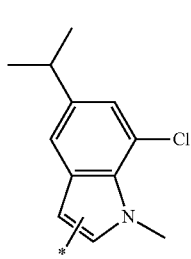 (ar-406)
[Chemical Formula 66]
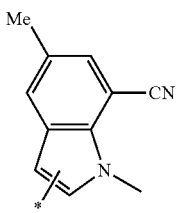 (ar-407)
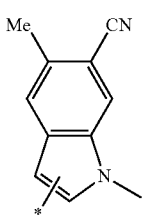 (ar-408)
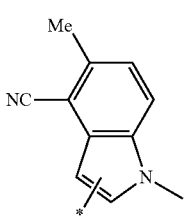 (ar-409)
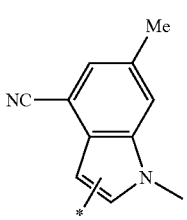 (ar-410)
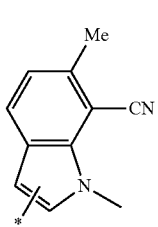 (ar-411)
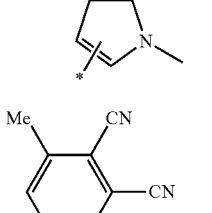 (ar-412)
(ar-413)

[Chemical Formula 67]
(ar-414)
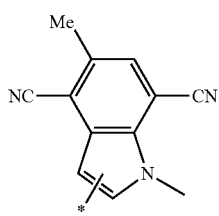
(ar-415)
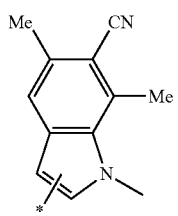
(ar-416)
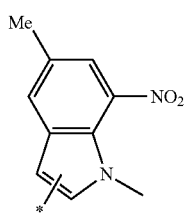
(ar-417)
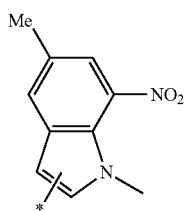
(ar-418)
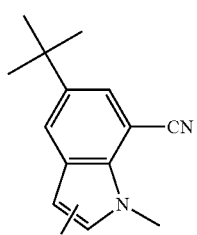
(ar-419)
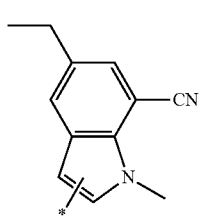
(ar-420)
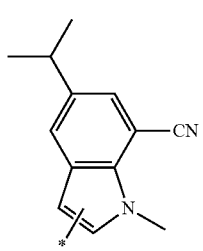
[Chemical Formula 68]
(ar-421)
(ar-422)
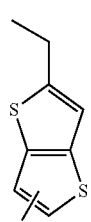
(ar-423)
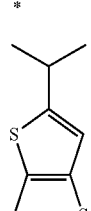
(ar-424)
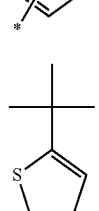
(ar-425)
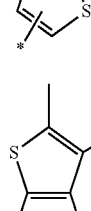
(ar-426)
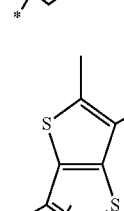
(ar-427)
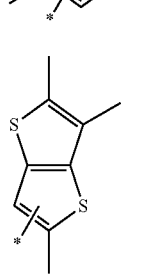

[Chemical Formula 69]
(ar-428) 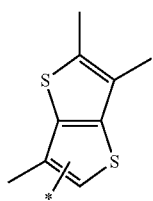
(ar-429) 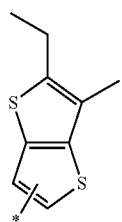
(ar-430) 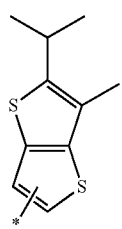
(ar-431) 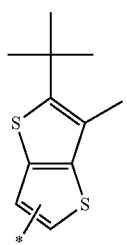
(ar-432) 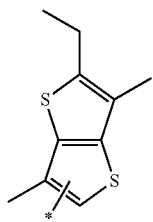
(ar-433) 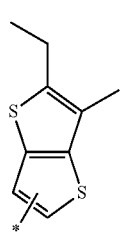
(ar-434) 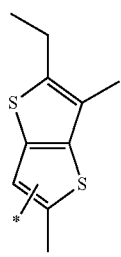
[Chemical Formula 70]
(ar-435)
(ar-436)
(ar-437)
(ar-438)
(ar-439)

-continued
(ar-439) 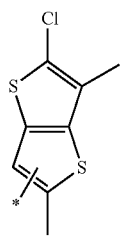
(ar-441) 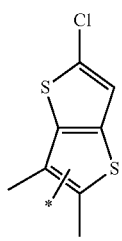
[Chemical Formula 71]
(ar-442) 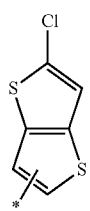
(ar-443) 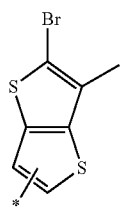
(ar-444) 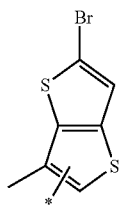
(ar-445) 
(ar-446) 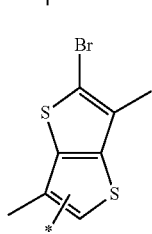
-continued
(ar-440) 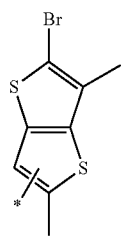
(ar-447) 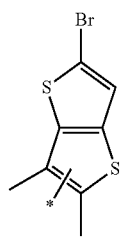
(ar-448) 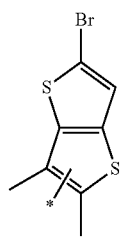
[Chemical Formula 72]
(ar-449) 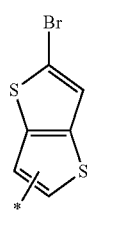
(ar-450) 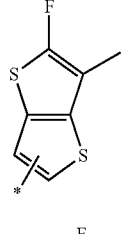
(ar-451) 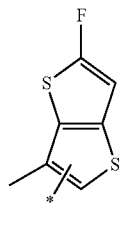
(ar-452) 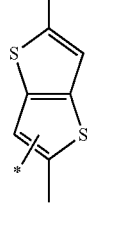
(ar-453) 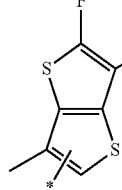

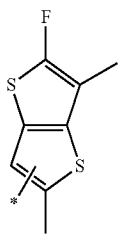 (ar-454)
 (ar-455)
[Chemical Formula 73]
 (ar-456)
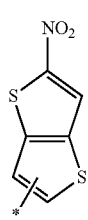 (ar-457)
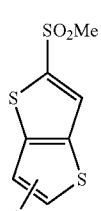 (ar-458)
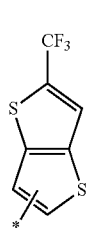 (ar-459)
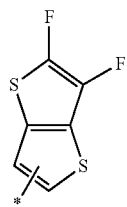 (ar-460)
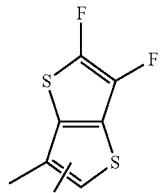 (ar-461)
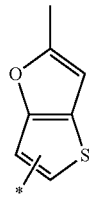 (ar-462)
[Chemical Formula 74]
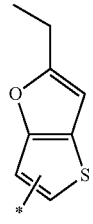 (ar-463)
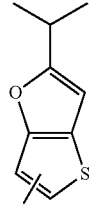 (ar-464)
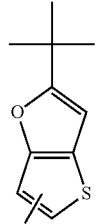 (ar-465)
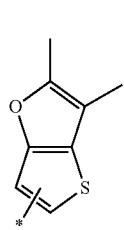 (ar-466)
 (ar-467)

[Chemical Formula 75]
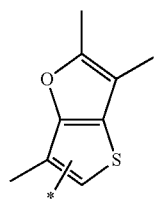 (ar-468)
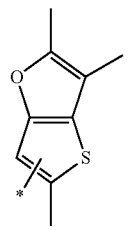 (ar-469)
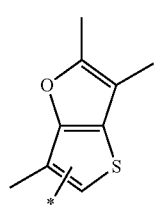 (ar-470)
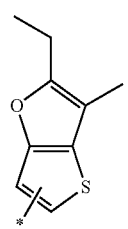 (ar-471)
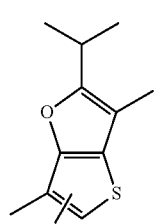 (ar-472)
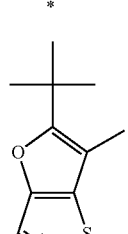 (ar-473)
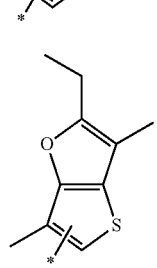 (ar-474)
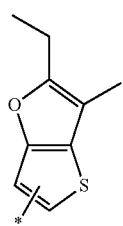 (ar-475)
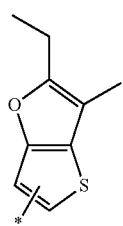 (ar-476)
[Chemical Formula 76]
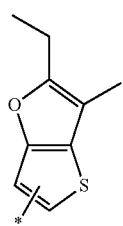 (ar-477)
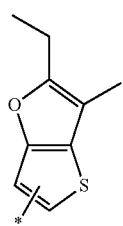 (ar-478)
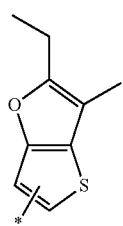 (ar-479)
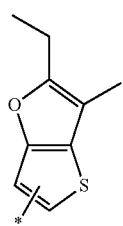 (ar-480)

(ar-481) 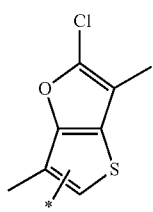
(ar-482) 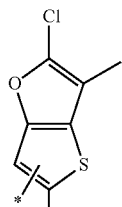
(ar-483) 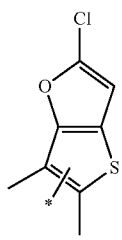
[Chemical Formula 77]
(ar-484) 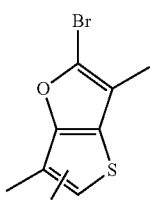
(ar-485) 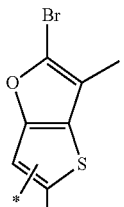
(ar-486) 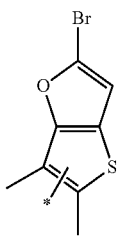
(ar-487) 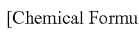
(ar-488) 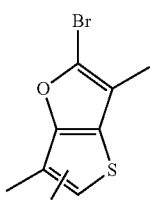
(ar-489) 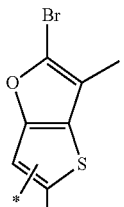
(ar-490) 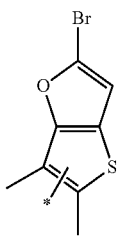
[Chemical Formula 78]
(ar-491) 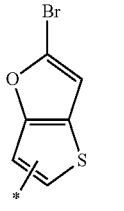
(ar-492) 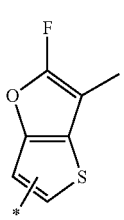
(ar-493) 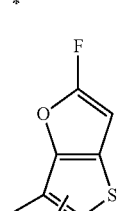
(ar-494) 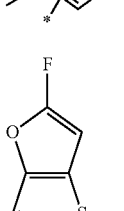

(ar-495) 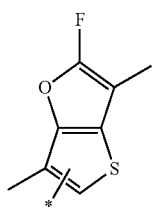
(ar-496) 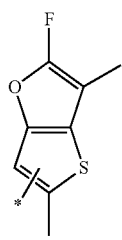
[Chemical Formula 78]
(ar-497) 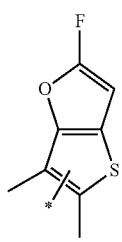
(ar-498) 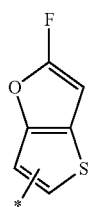
(ar-499) 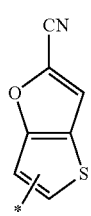
(ar-500) 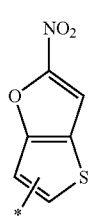
(ar-501) 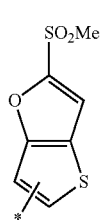
(ar-502) 
(ar-503) 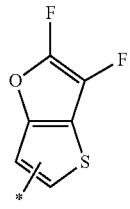
(ar-504) 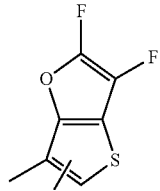
[Chemical Formula 80]
(ar-505) 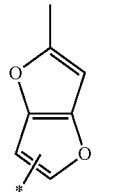
(ar-506) 
(ar-507) 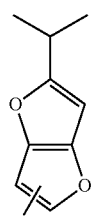
(ar-508) 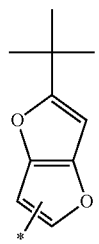

(ar-509) 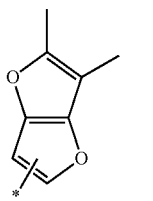
(ar-510) 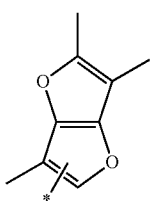
(ar-511) 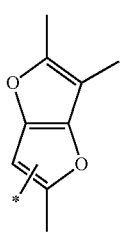
[Chemical Formula 81]
(ar-512) 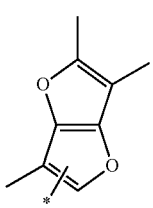
(ar-513) 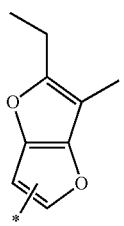
(ar-514) 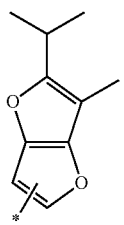
(ar-515) 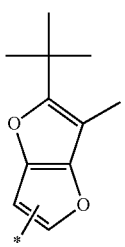
(ar-516) 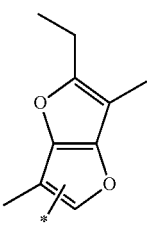
(ar-517) 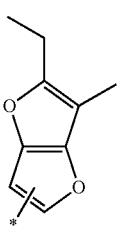
(ar-518) 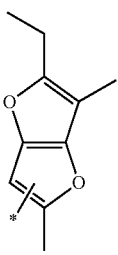
[Chemical Formula 82]
(ar-519) 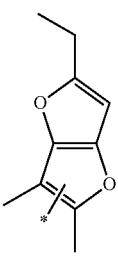
(ar-520) 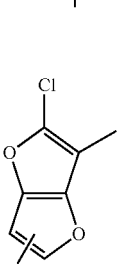
(ar-521) 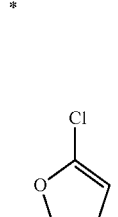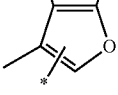

-continued
(ar-522) 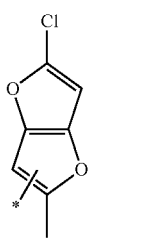
(ar-523) 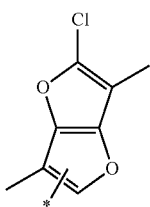
(ar-524) 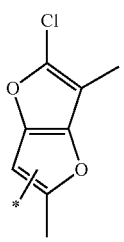
(ar-525) 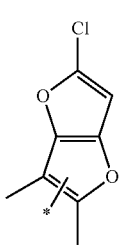
[Chemical Formula 83]
(ar-526) 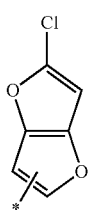
(ar-527) 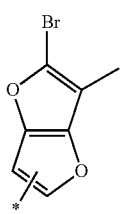
(ar-528) 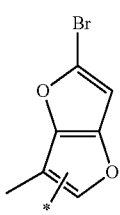
-continued
(ar-529) 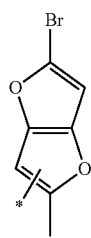
(ar-530) 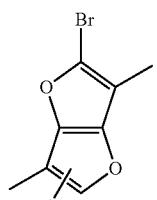
(ar-531) 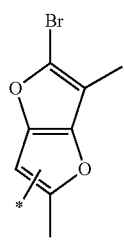
(ar-532) 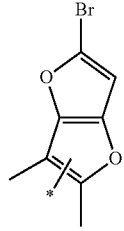
[Chemical Formula 84]
(ar-533) 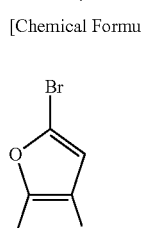
(ar-534) 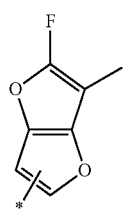
(ar-535) 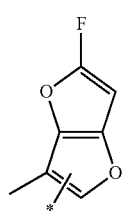

(ar-536) 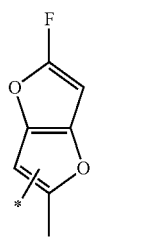
(ar-537) 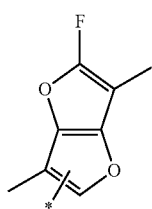
(ar-538) 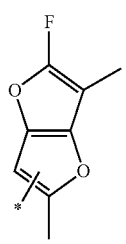
(ar-539) 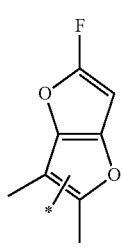
[Chemical Formula 85]
(ar-540) 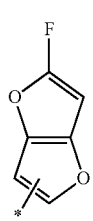
(ar-541) 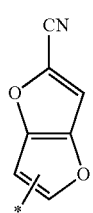
(ar-542) 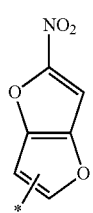
(ar-543) 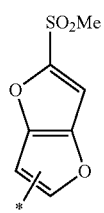
(ar-544) 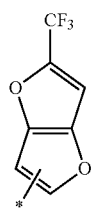
(ar-545) 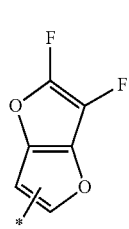
(ar-546) 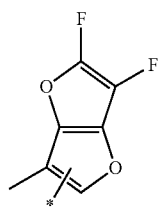
[Chemical Formula 86]
(ar-547) 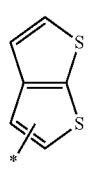
(ar-548) 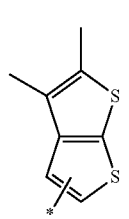
(ar-549) 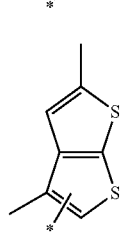

(ar-550) 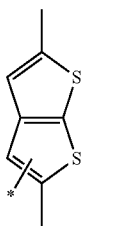
(ar-551) 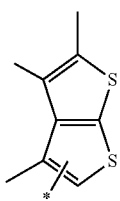
(ar-552) 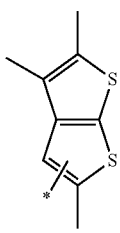
(ar-553) 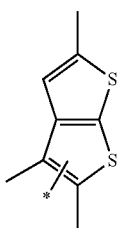
[Chemical Formula 87]
(ar-554) 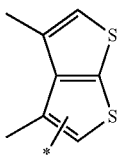
(ar-555) 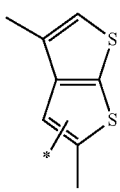
(ar-556) 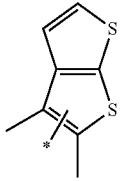
(ar-557) 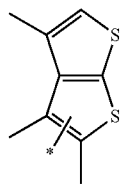
(ar-558) 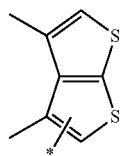
(ar-559) 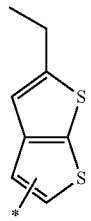
(ar-560) 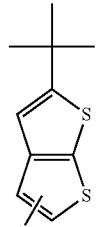
[Chemical Formula 88]
(ar-561) 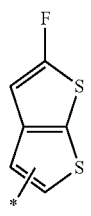
(ar-562) 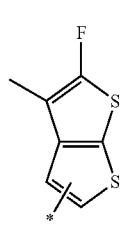
(ar-563) 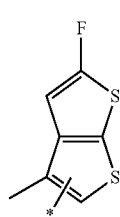

(ar-564) 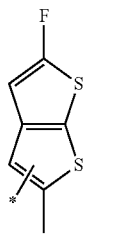
(ar-565) 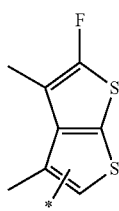
(ar-566) 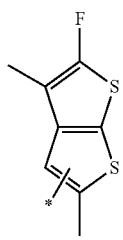
(ar-567) 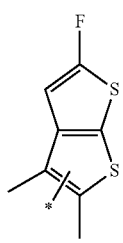
[Chemical Formula 89]
(ar-568) 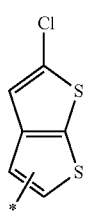
(ar-569) 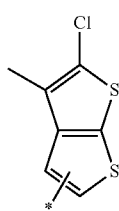
(ar-570) 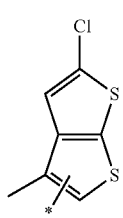
(ar-571) 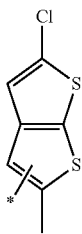
(ar-572) 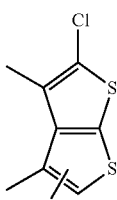
(ar-573) 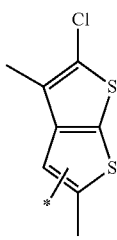
(ar-574) 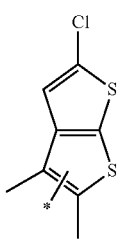
[Chemical Formula 90]
(ar-575) 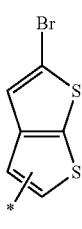
(ar-576) 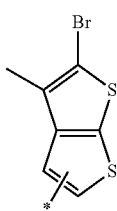
(ar-577) 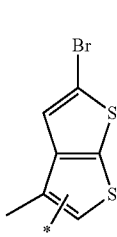

(ar-578) 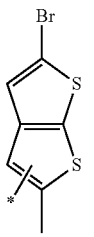
(ar-579) 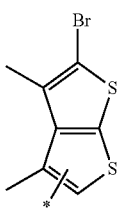
(ar-580) 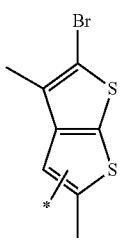
(ar-581) 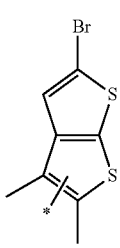
[Chemical Formula 91]
(ar-582) 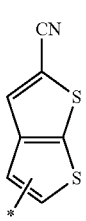
(ar-583) 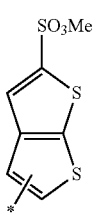
(ar-584) 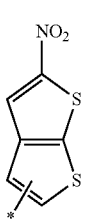
(ar-585) 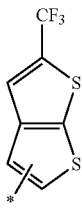
(ar-586) 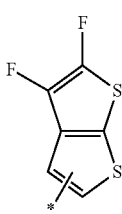
(ar-587) 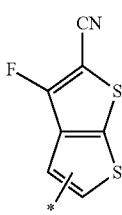
(ar-588) 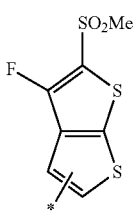
[Chemical Formula 92]
(ar-589) 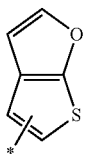
(ar-590) 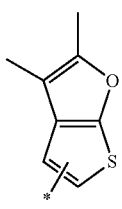
(ar-591) 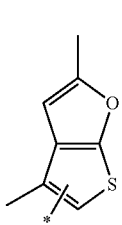

(ar-592) 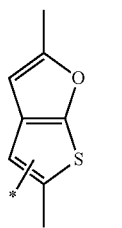
(ar-593) 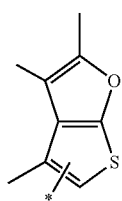
(ar-594) 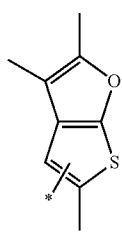
(ar-595) 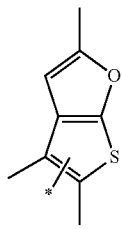
[Chemical Formula 93]
(ar-596) 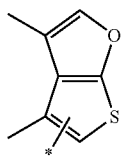
(ar-597) 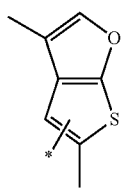
(ar-598) 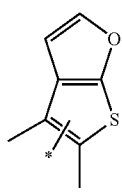
(ar-599) 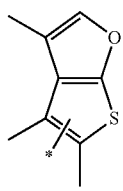
(ar-600) 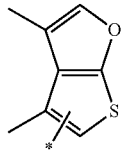
(ar-601) 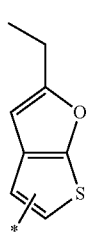
(ar-602) 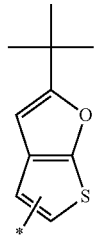
[Chemical Formula 94]
(ar-603) 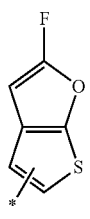
(ar-604) 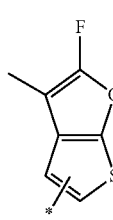
(ar-605) 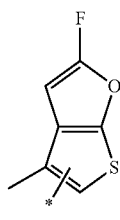

(ar-606)
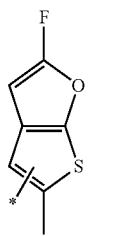
(ar-607)
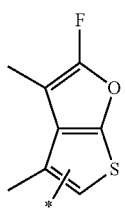
(ar-608)
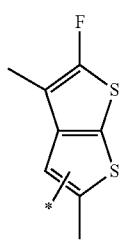
(ar-609)
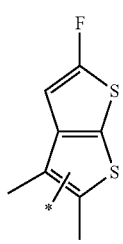
[Chemical Formula 95]
(ar-610)
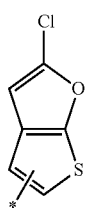
(ar-611)
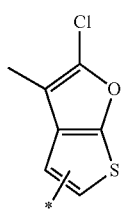
(ar-612)
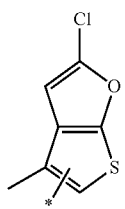
(ar-613)
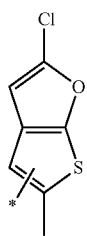
(ar-614)
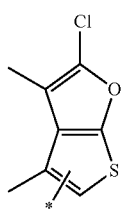
(ar-615)
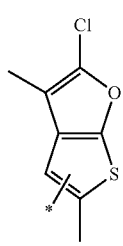
(ar-616)
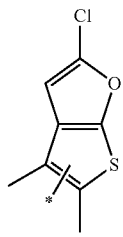
[Chemical Formula 96]
(ar-617)
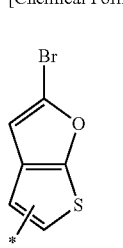
(ar-618)
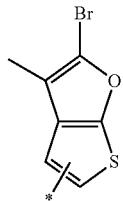
(ar-619)
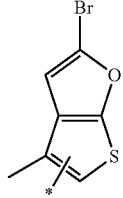

(ar-620) 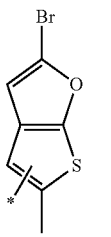
(ar-621) 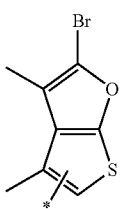
(ar-622) 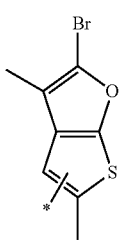
(ar-623) 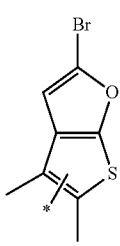
[Chemical Formula 97]
(ar-624) 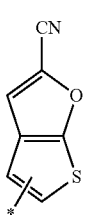
(ar-625) 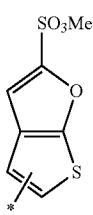
(ar-626) 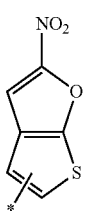
(ar-627) 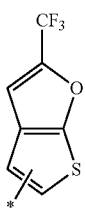
(ar-628) 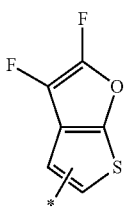
(ar-629) 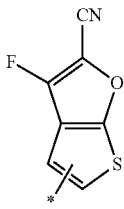
(ar-630) 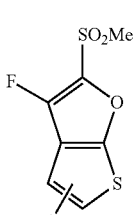
[Chemical Formula 98]
(ar-631) 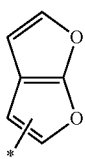
(ar-632)
(ar-633) 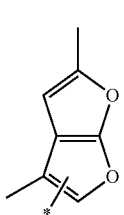

(ar-634)
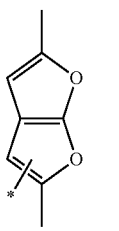
(ar-635)
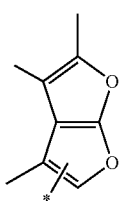
(ar-636)
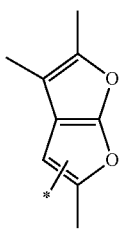
(ar-637)
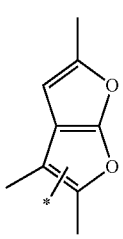
[Chemical Formula 99]
(ar-638)
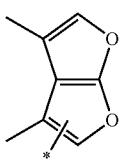
(ar-639)
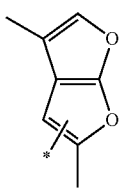
(ar-640)
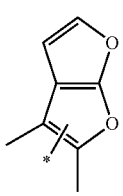
(ar-641)
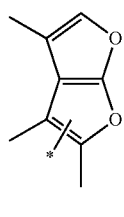
(ar-642)
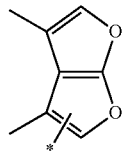
(ar-643)
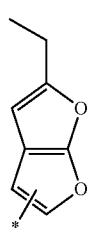
(ar-644)
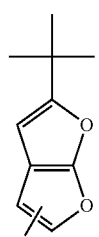
[Chemical Formula 100]
(ar-645)
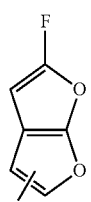
(ar-646)
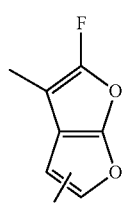
(ar-647)
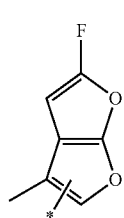

(ar-648) 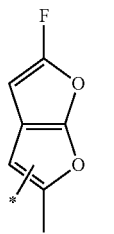
(ar-649) 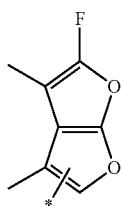
(ar-650) 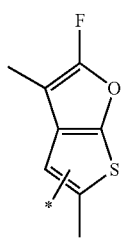
(ar-651) 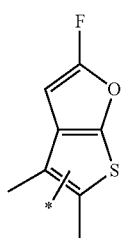
[Chemical Formula 101]
(ar-652) 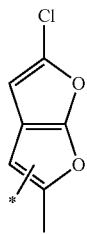
(ar-653)
(ar-654)
(ar-655) 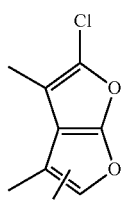
(ar-656) 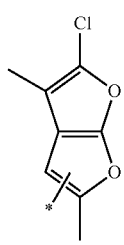
(ar-657) 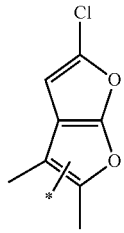
(ar-658) 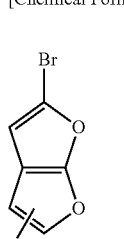
[Chemical Formula 102]
(ar-659) 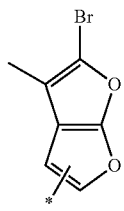
(ar-660)
(ar-661) 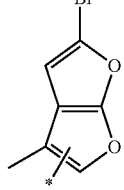

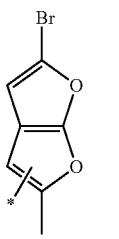 (ar-662)
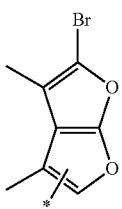 (ar-663)
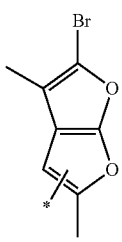 (ar-664)
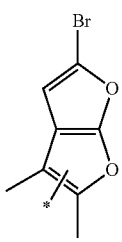 (ar-665)
[Chemical Formula 103]
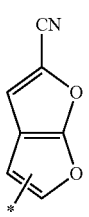 (ar-666)
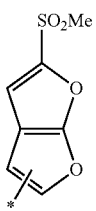 (ar-667)
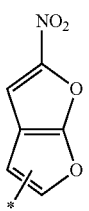 (ar-668)
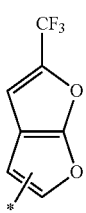 (ar-669)
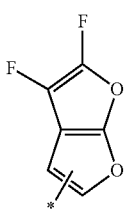 (ar-670)
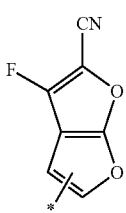 (ar-671)
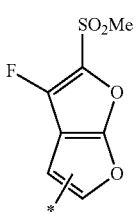 (ar-672)
[Chemical Formula 104]
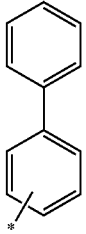 (ar-673)
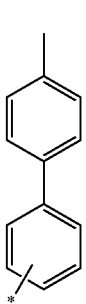 (ar-674)

(ar-675) 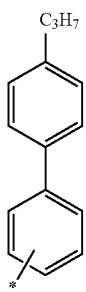
(ar-676) 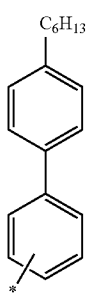
(ar-677) 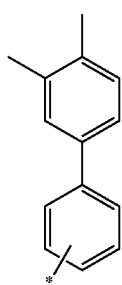
(ar-678) 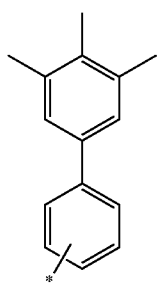
(ar-679) 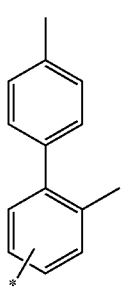
[Chemical Formula 105]
(ar-680) 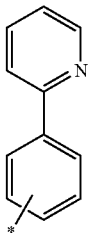
(ar-681) 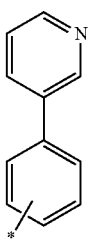
(ar-682) 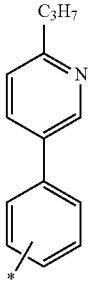
(ar-683) 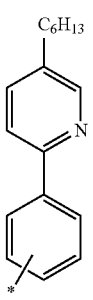
(ar-684) 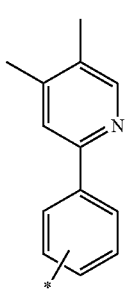

-continued
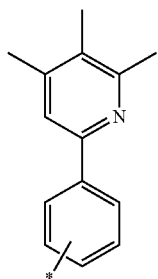 (ar-685)
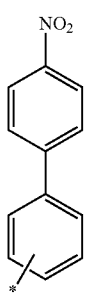 (ar-686)
[Chemical Formula 106]
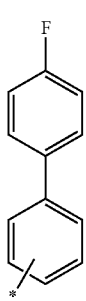 (ar-687)
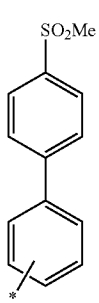 (ar-688)
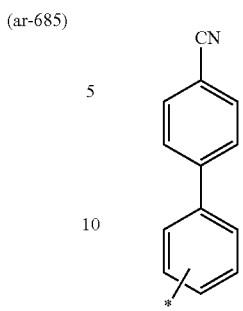 (ar-690)
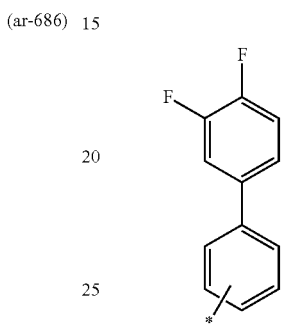 (ar-691)
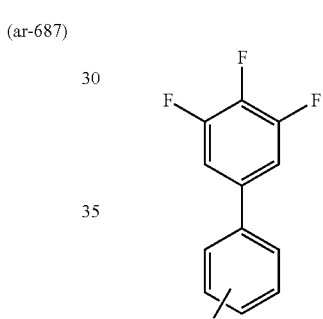 (ar-692)
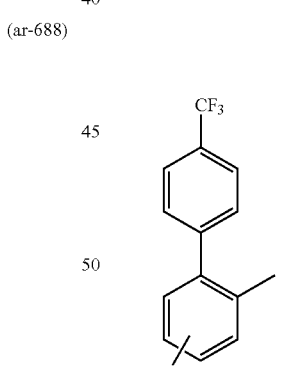 (ar-693)
[Chemical Formula 107]
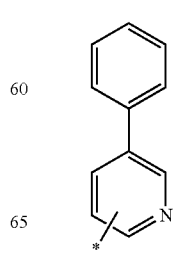 (ar-694)
(ar-689)

(ar-695)
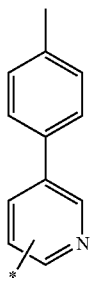
(ar-696)
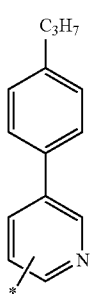
(ar-697)
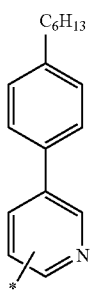
(ar-698)
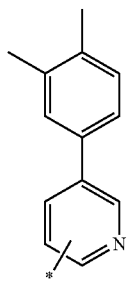
(ar-699)
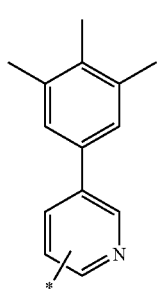
(ar-700)
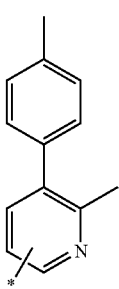
[Chemical Formula 108]
(ar-701)
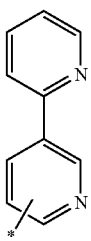
(ar-702)
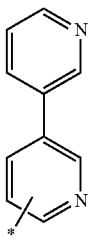
(ar-703)
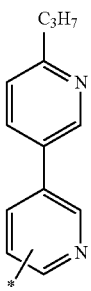
(ar-704)
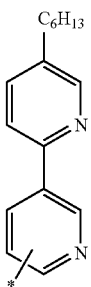

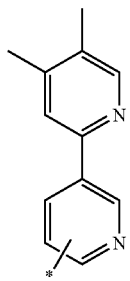
(ar-705)
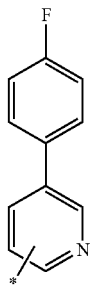
(ar-710)
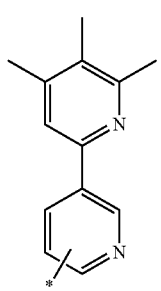
(ar-706)
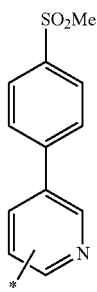
(ar-711)
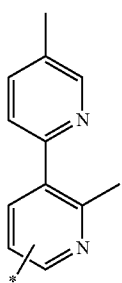
(ar-707)
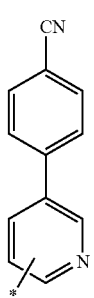
(ar-712)
[Chemical Formula 109]
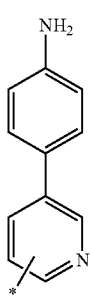
(ar-708)
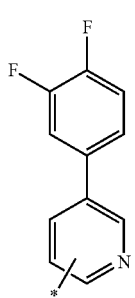
(ar-713)
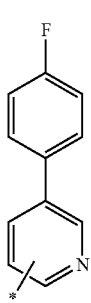
(ar-709)
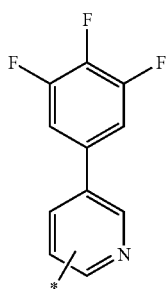
(ar-714)

(ar-714) 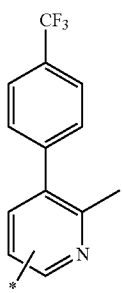
[Chemical Formula 110]
(ar-715) 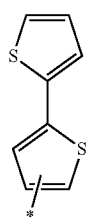
(ar-716) 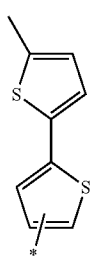
(ar-717) 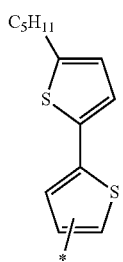
(ar-718) 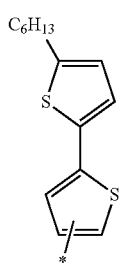
(ar-719) 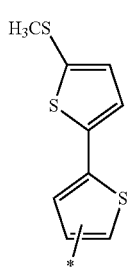
(ar-720) 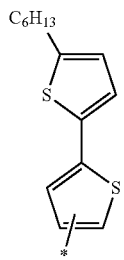
(ar-721) 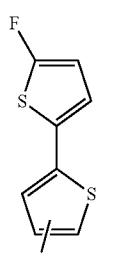
[Chemical Formula 111]
(ar-722) 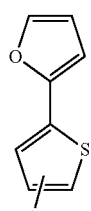
(ar-723) 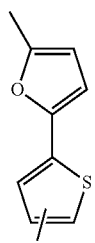
(ar-724) 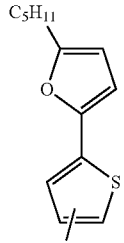
(ar-725) 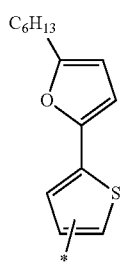

(ar-726) 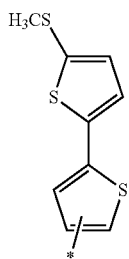
(ar-727) 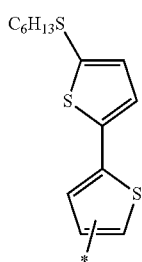
(ar-728) 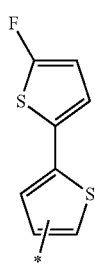
[Chemical Formula 112]
(ar-729) 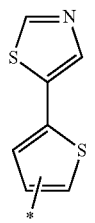
(ar-730) 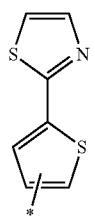
(ar-731) 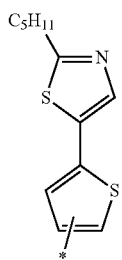
(ar-732) 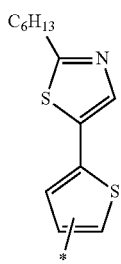
(ar-733) 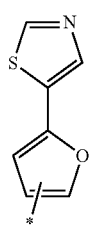
(ar-734) 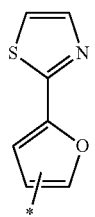
(ar-735) 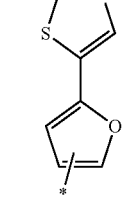
[Chemical Formula 113]
(ar-736) 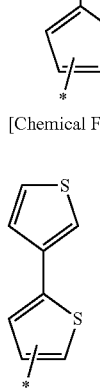
(ar-737) 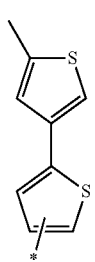

(ar-738) 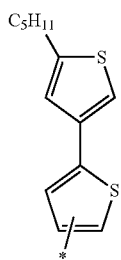
(ar-739) 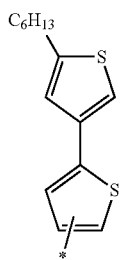
(ar-740) 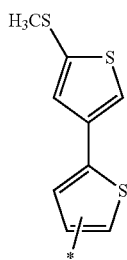
(ar-741) 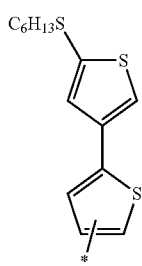
(ar-742) 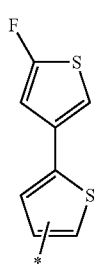
[Chemical Formula 114]
(ar-743) 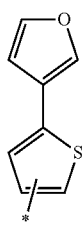
(ar-744) 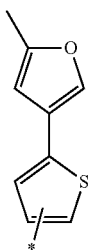
(ar-745) 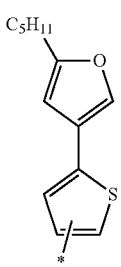
(ar-746) 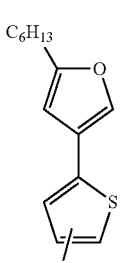
(ar-747) 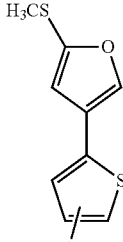
(ar-748) 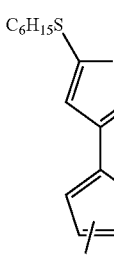
(ar-749) 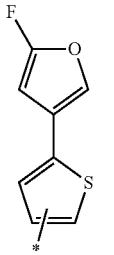

[Chemical Formula 115]
(ar-750) 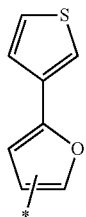
(ar-751) 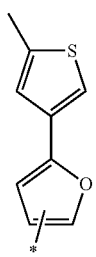
(ar-752) 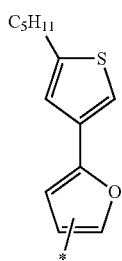
(ar-753) 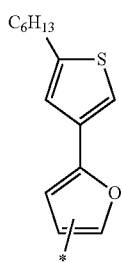
(ar-754) 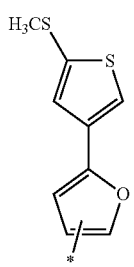
(ar-755) 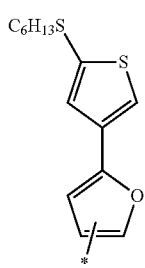
(ar-756) 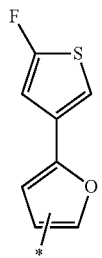
[Chemical Formula 116]
(ar-757) 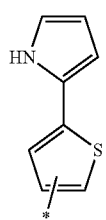
(ar-758) 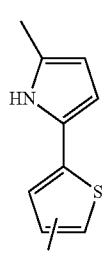
(ar-759) 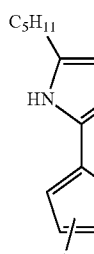
(ar-760) 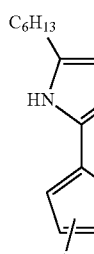
(ar-761) 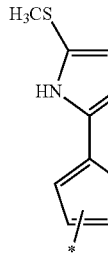

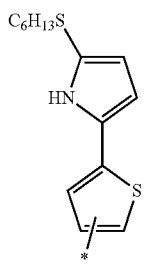 (ar-762)
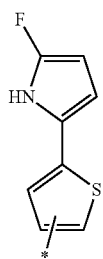 (ar-763)
[Chemical Formula 117]
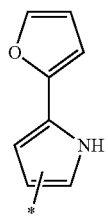 (ar-764)
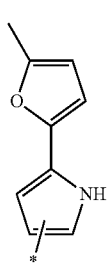 (ar-765)
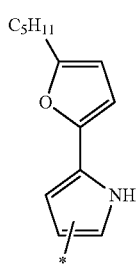 (ar-766)
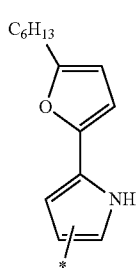 (ar-767)
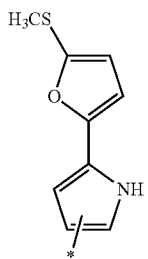 (ar-768)
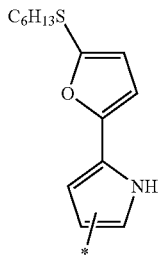 (ar-769)
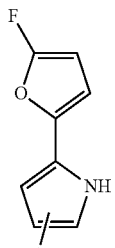 (ar-770)
[Chemical Formula 118]
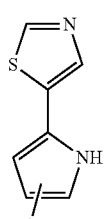 (ar-771)
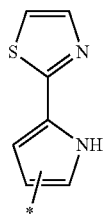 (ar-772)
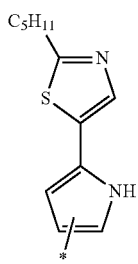 (ar-773)

[Chemical structure page - continued listing of compounds ar-774 through ar-789]

(ar-774)

(ar-780)

[Chemical Formula 120]

(ar-775)

(ar-785)

(ar-776)

(ar-786)

(ar-777)

(ar-787)

[Chemical Formula 119]

(ar-778)

(ar-788)

(ar-779)

(ar-789)

-continued
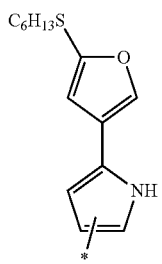 (ar-790)
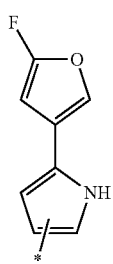 (ar-791)
[Chemical Formula 121]
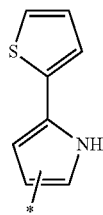 (ar-792)
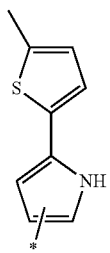 (ar-793)
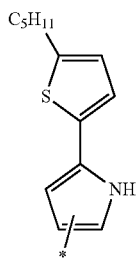 (ar-794)
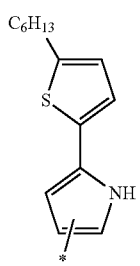 (ar-795)
-continued
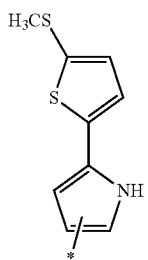 (ar-796)
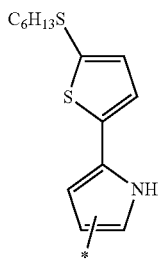 (ar-797)
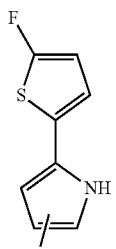 (ar-798)
[Chemical Formula 122]
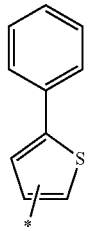 (ar-799)
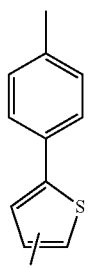 (ar-800)
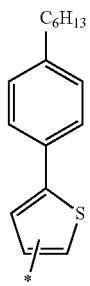 (ar-801)

(ar-802)
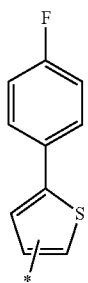
(ar-803)
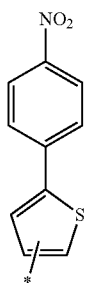
(ar-804)
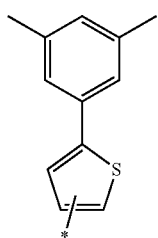
(ar-805)
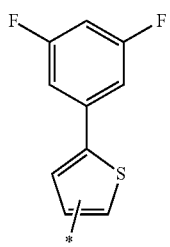
[Chemical Formula 1236]
(ar-806)
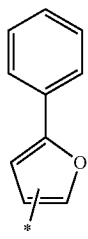
(ar-807)
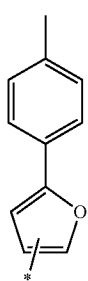
(ar-808)
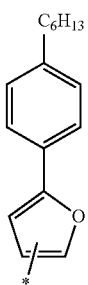
(ar-809)
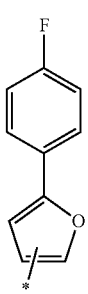
(ar-810)
(ar-811)
(ar-812)

[Chemical Formula 124]
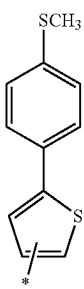 (ar-813)
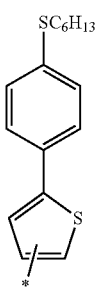 (ar-814)
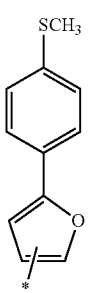 (ar-815)
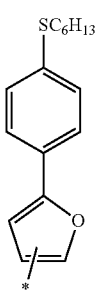 (ar-816)
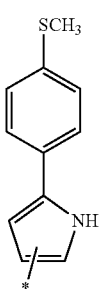 (ar-817)
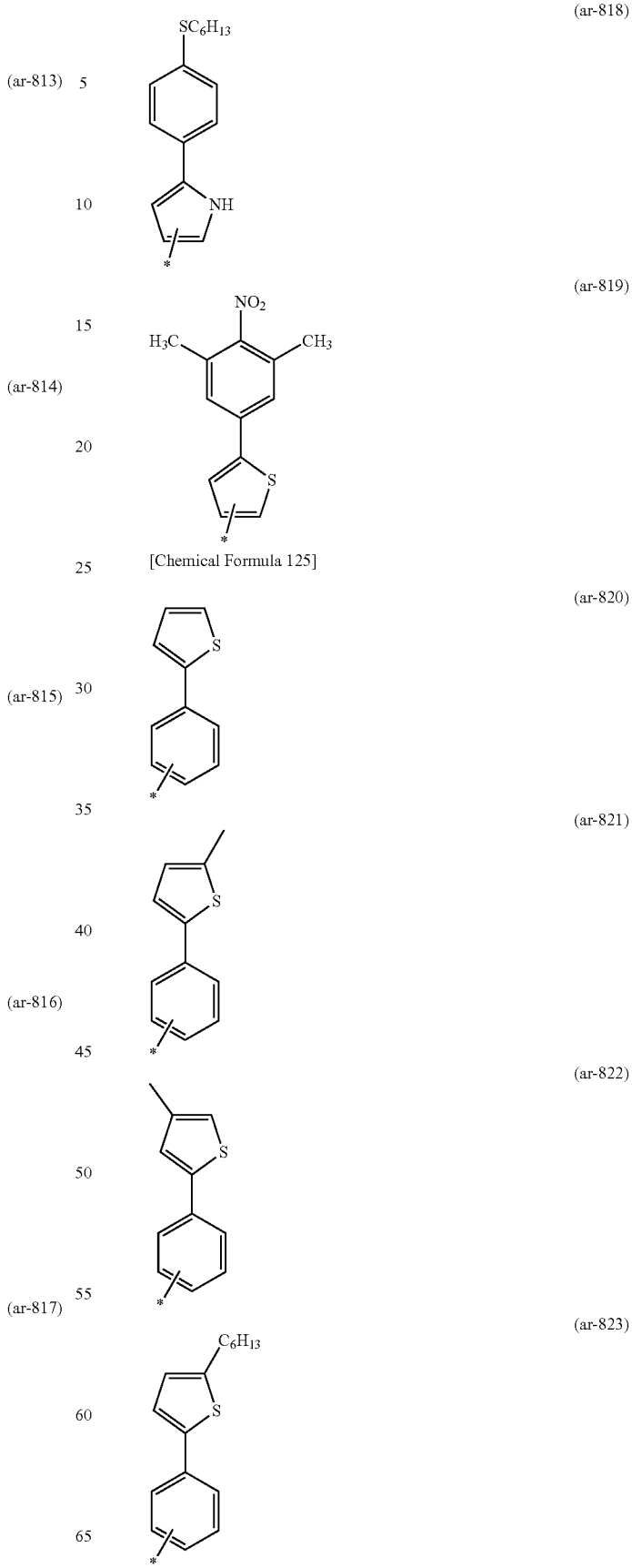

(ar-824) 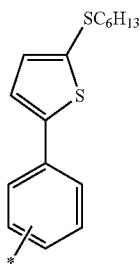
(ar-825) 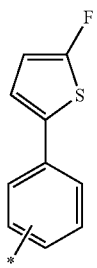
(ar-826) 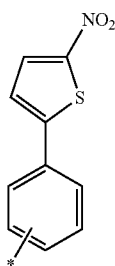
[Chemical Formula 126]
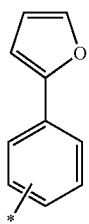
(ar-828)
(ar-829)
(ar-830) 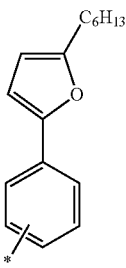
(ar-831) 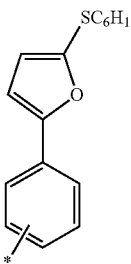
(ar-832) 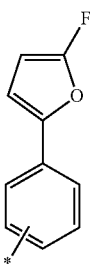
(ar-833) 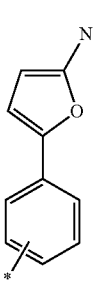
[Chemical Formula 127]
(ar-834) 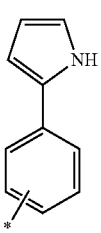
(ar-835) 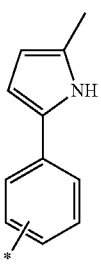

(ar-836) 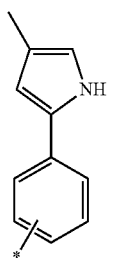

(ar-837) 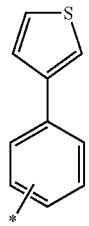

(ar-838) 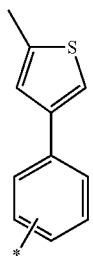

(ar-839) 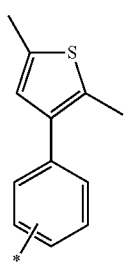

(ar-840) 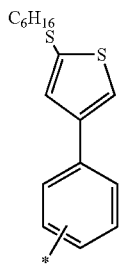

[Chemical Formula 128]

(ar-841) 

(ar-842) 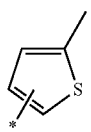

(ar-843) 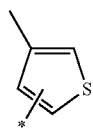

(ar-844) 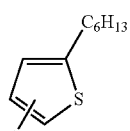

(ar-845) 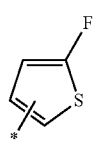

(ar-846) 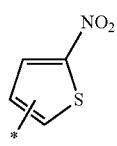

Specifically, examples of the polymerizable liquid crystal compound represented by formula (A) include the following compounds. Then, a liquid crystal composition of the present invention can contain, as a polymerizable liquid crystal compound, only one polymerizable liquid crystal compound, or can contain 2 or more polymerizable liquid crystal compounds.

[Chemical Formula 129]

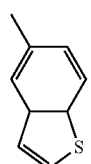

(A2-1) 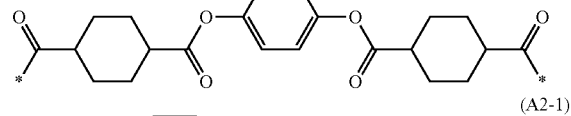

(A2-2) 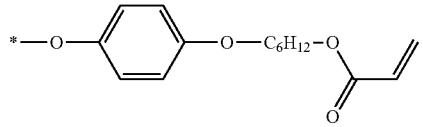

-continued (A2-3)
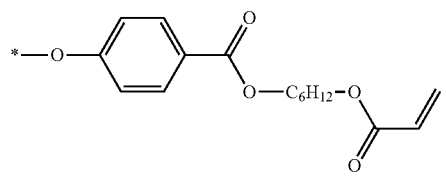

(A2-4)
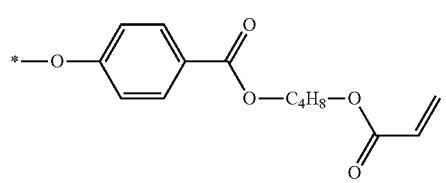

(A2-5)
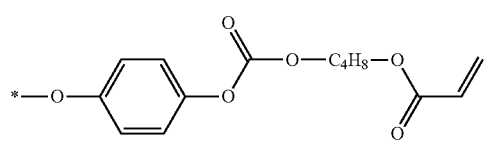

(A2-6)

*—O—⟨cyclohexyl⟩—O—C₆H₁₂—O—acrylate (A2-7)
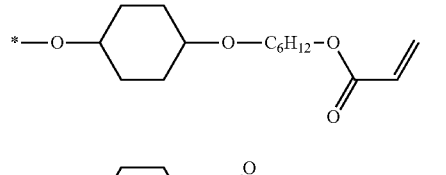

(A2-8)
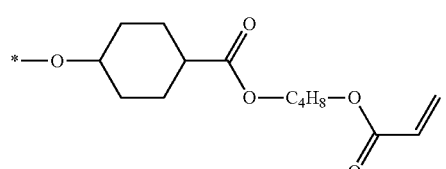

[Chemical Formula 130]

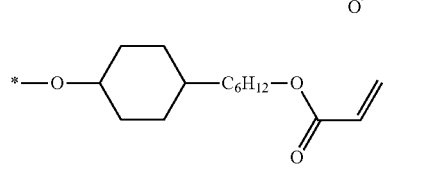

(A4-1)

*—O—⟨phenyl⟩—O—C₆H₁₂—O—acrylate

-continued (A4-2)

*—O—⟨phenyl⟩—O—C₄H₈—O—acrylate (A4-3)

*—O—⟨phenyl⟩—C(O)—O—C₆H₁₂—O—acrylate (A4-4)

*—O—⟨phenyl⟩—C(O)—O—C₄H₈—O—acrylate (A4-5)

*—O—⟨phenyl⟩—O—C(O)—O—C₄H₈—O—acrylate (A4-6)

*—O—⟨cyclohexyl⟩—O—C₆H₁₂—O—acrylate (A4-7)

*—O—⟨cyclohexyl⟩—C(O)—O—C₄H₈—O—acrylate (A4-8)

*—O—⟨cyclohexyl⟩—C₆H₁₂—O—acrylate

[Chemical Formula 131]

(A5-1)

*—O—⟨phenyl⟩—O—C₆H₁₂—O—acrylate

-continued (A5-2), (A5-3), (A5-4), (A5-5), (A5-6), (A5-7), (A5-8)

[Chemical Formula 132]

-continued (A6-1), (A6-2), (A6-3), (A6-4), (A6-5), (A6-6), (A6-7), (A6-8)

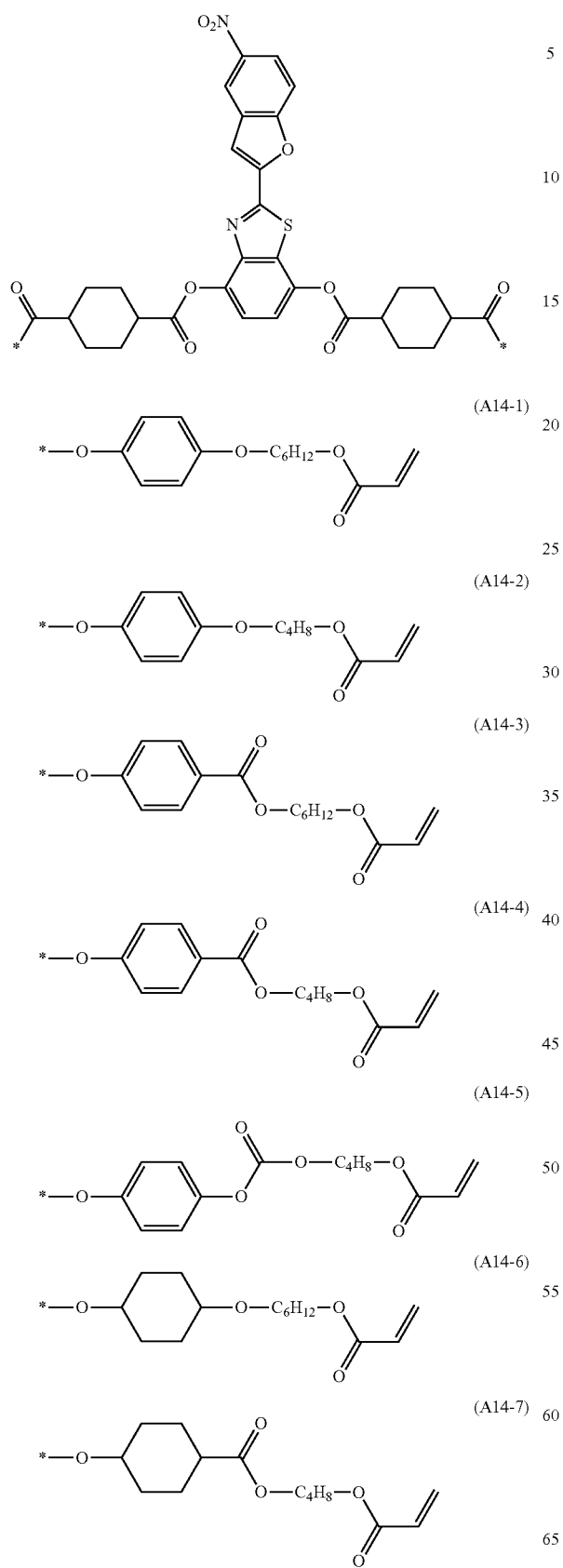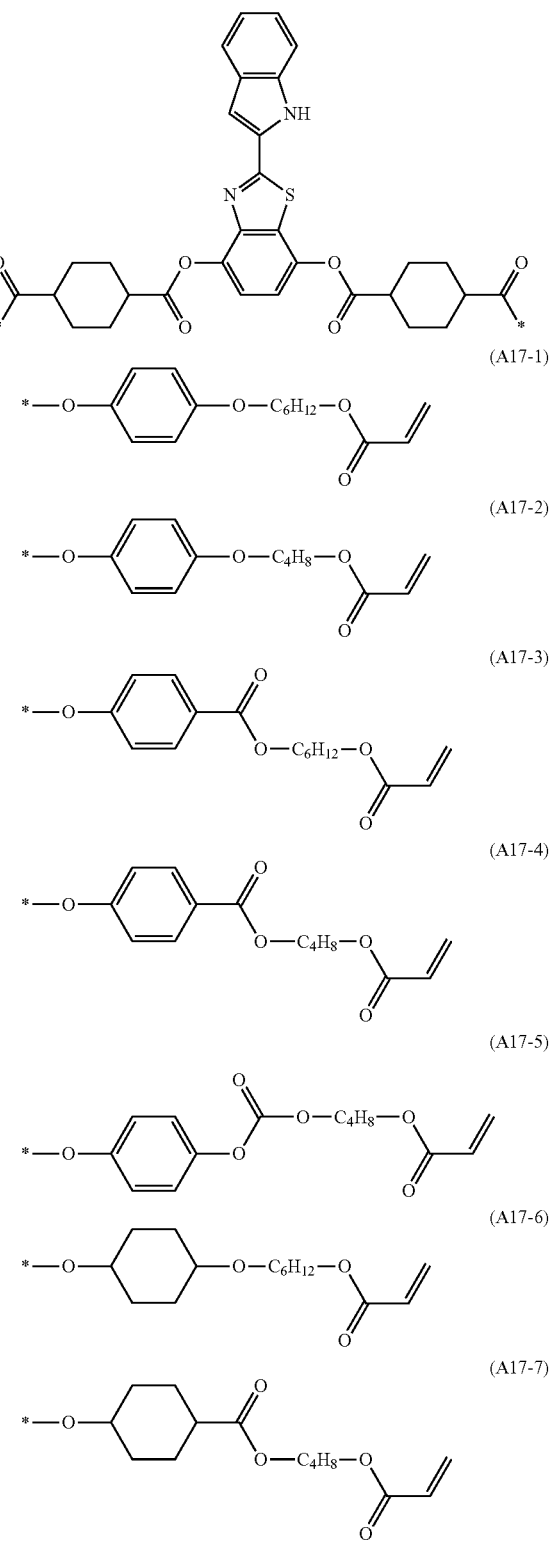

(A17-8)
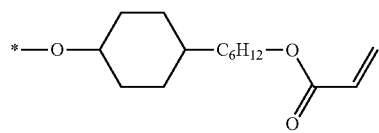
[Chemical Formula 135]
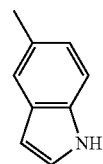
(A18-1)
(A18-2)
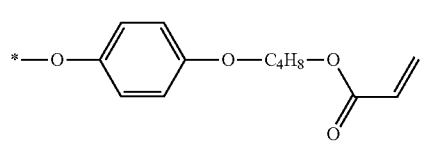
(A18-3)
(A18-4)
(A18-5)
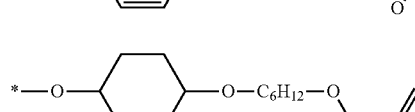
(A18-6)
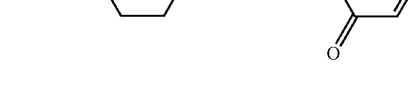
(A18-7)
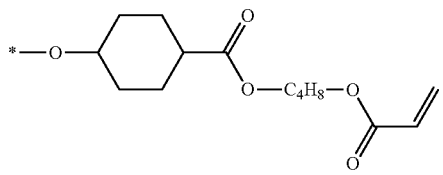
(A18-8)
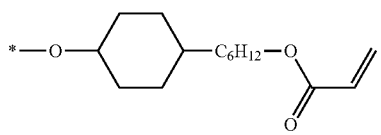
[Chemical Formula 136]
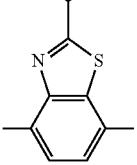
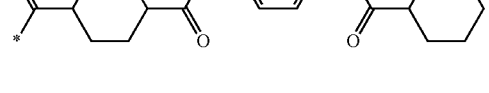
(A21-1)
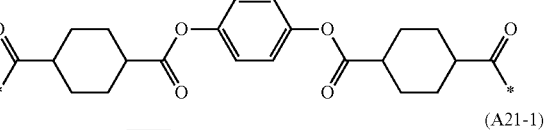
(A21-2)
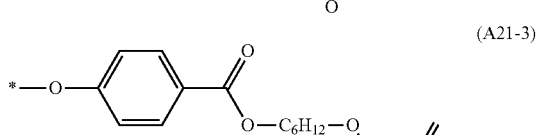
(A21-3)
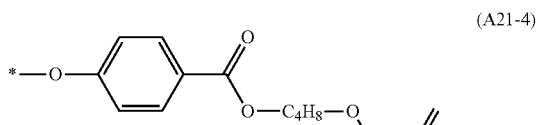
(A21-4)
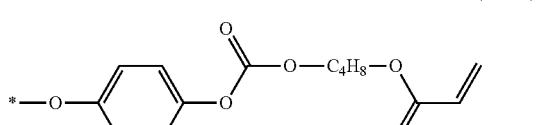
(A21-5)
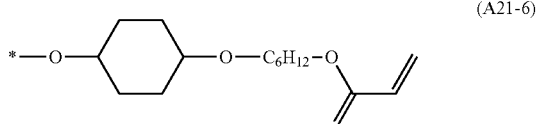
(A21-6)

-continued
(A21-7)
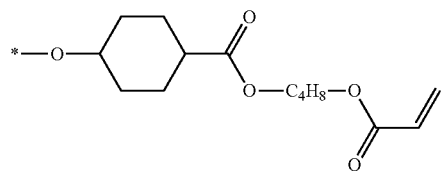
(A21-8)
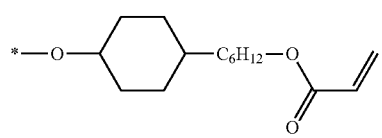
[Chemical Formula 137]
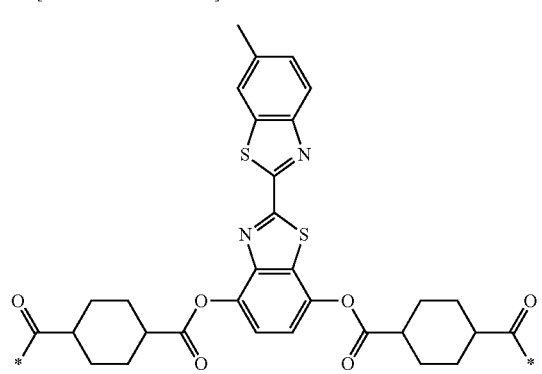
(A22-1)
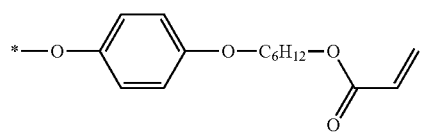
(A22-2)
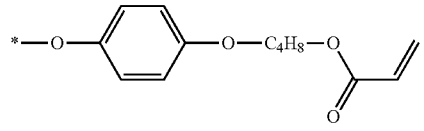
(A22-3)
(A22-4)
(A22-5)
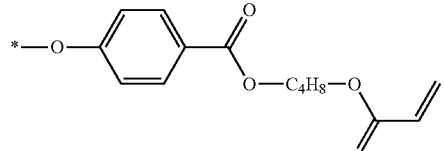
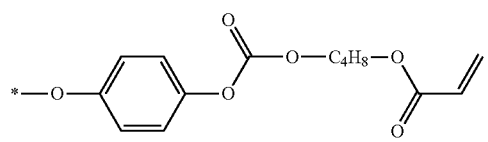
-continued
(A22-6)
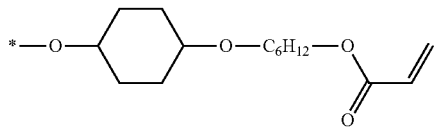
(A22-7)
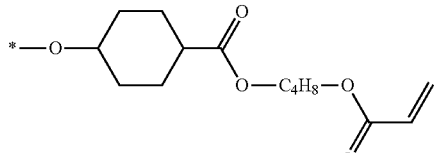
(A22-8)
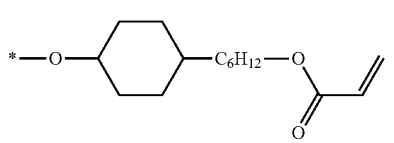
[Chemical Formula 138]
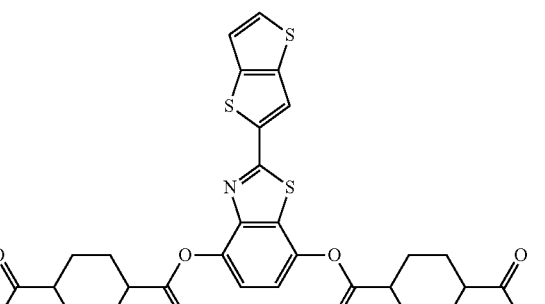
(A25-1)
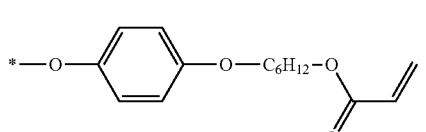
(A25-2)
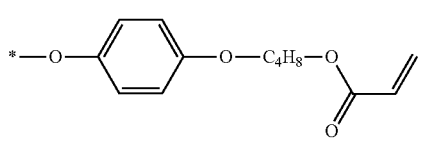
(A25-3)
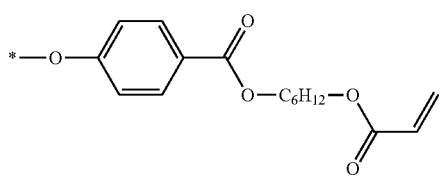
(A25-4)
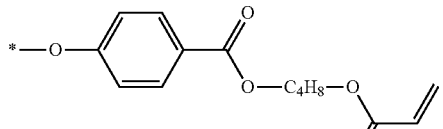
(A25-5)
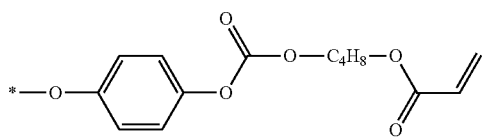

(A25-6)
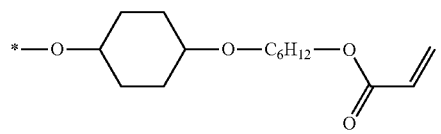
(A25-7)
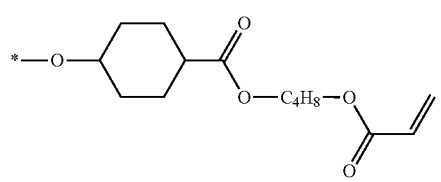
(A25-8)
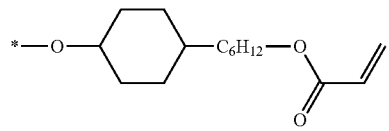
[Chemical Formula 139]
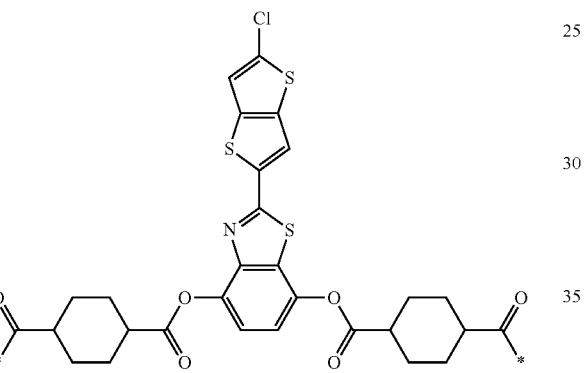
(A28-1)
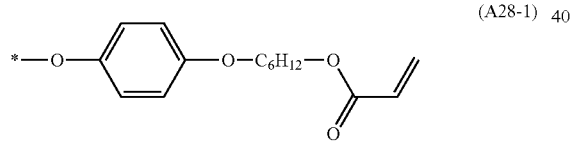
(A28-2)
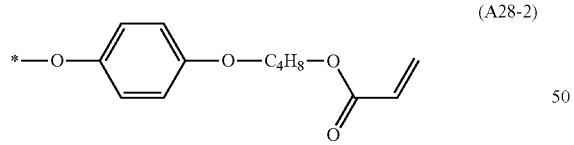
(A28-3)
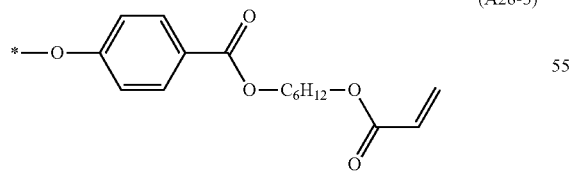
(A28-4)
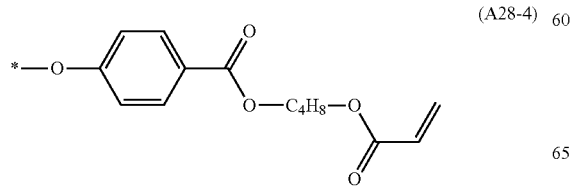
(A28-5)
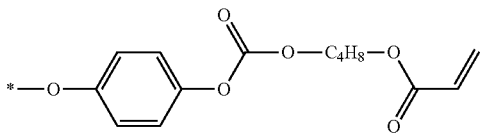
(A28-6)
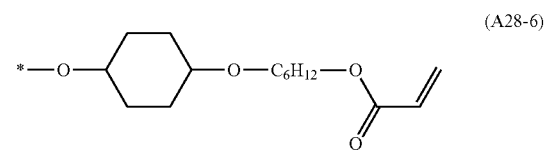
(A28-7)
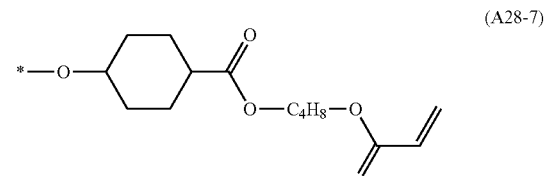
(A28-8)
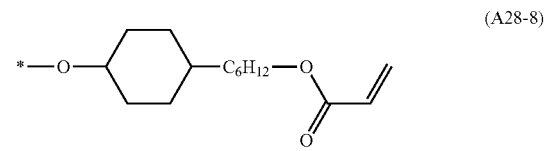
[Chemical Formula 140]
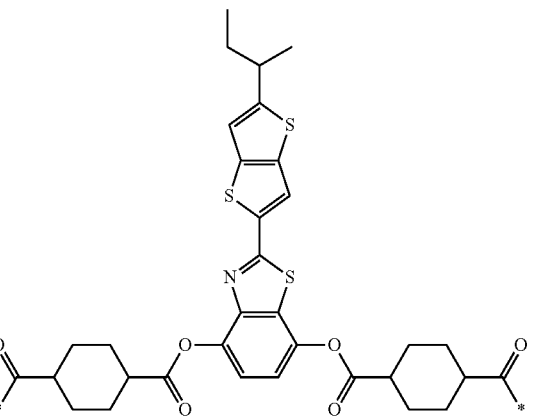
(A31-1)
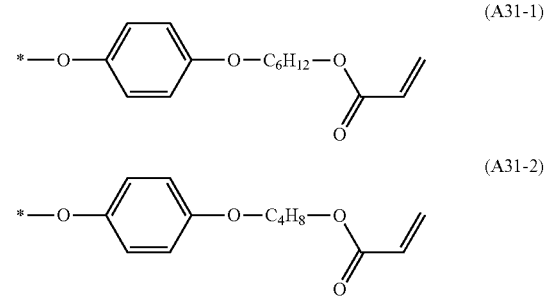
(A31-2)
(A31-3)
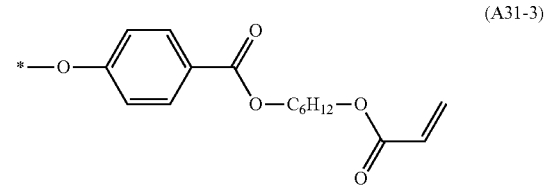

161
-continued
(A31-4)
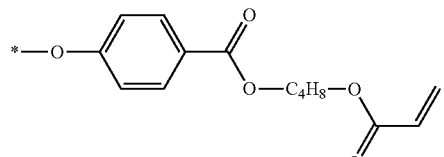
(A31-5)
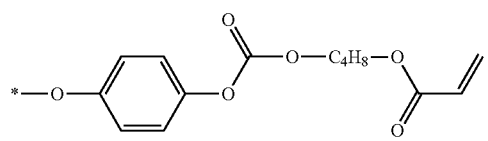
(A31-6)
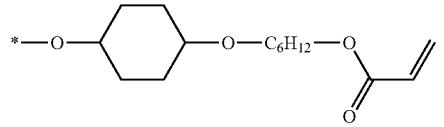
(A31-7)
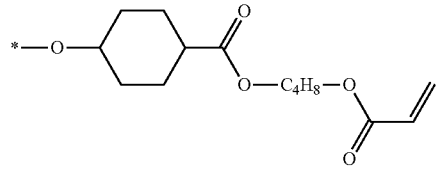
(A31-8)
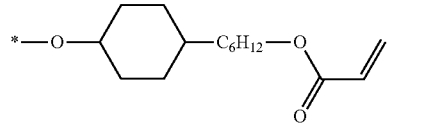
[Chemical Formula 141]
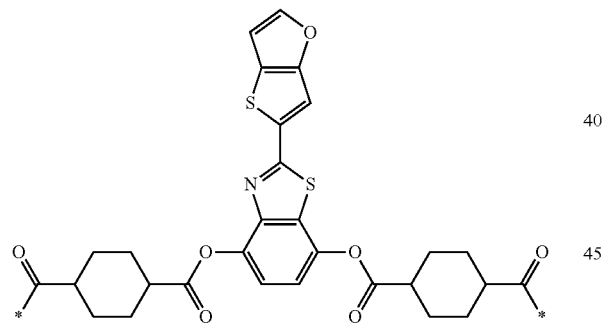
(A33-1)
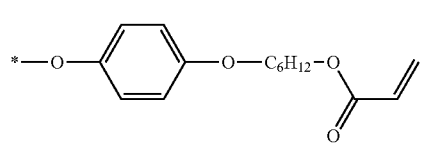
(A33-2)
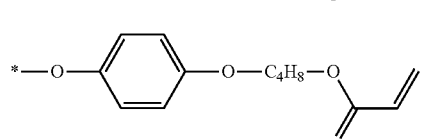
(A33-3)
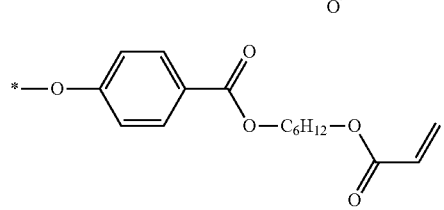
162
-continued
(A33-4)
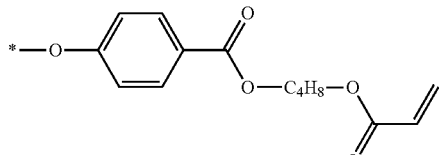
(A33-5)
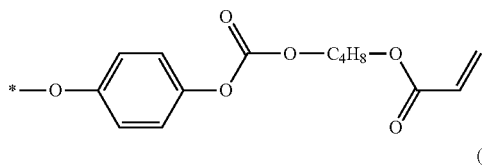
(A33-6)
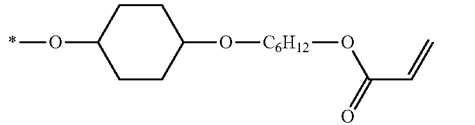
(A33-7)
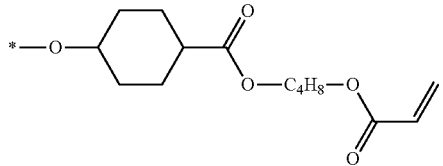
(A33-8)
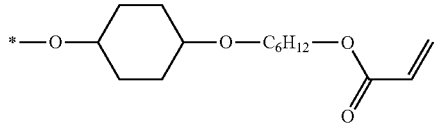
[Chemical Formula 142]
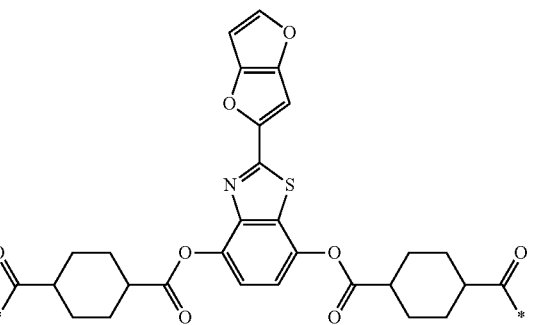
(A34-1)
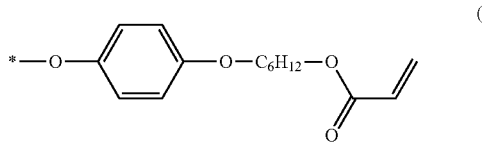
(A34-2)
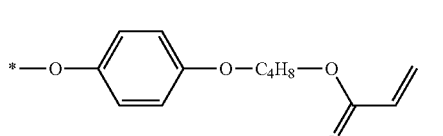
(A34-3)
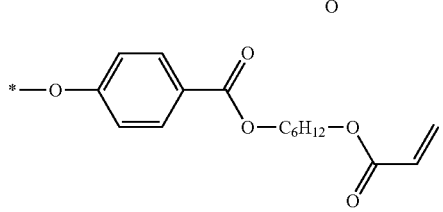

(A34-4)
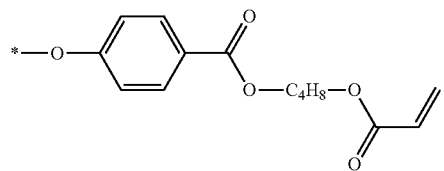
(A34-5)
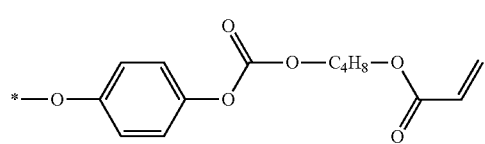
(A34-6)
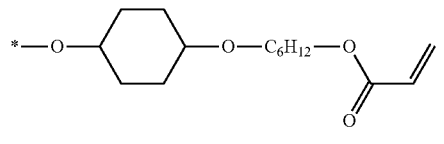
(A34-7)
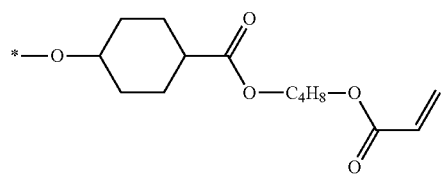
(A34-8)
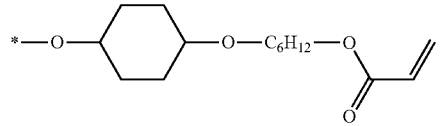
[Chemical Formula 143]
(A41-1)
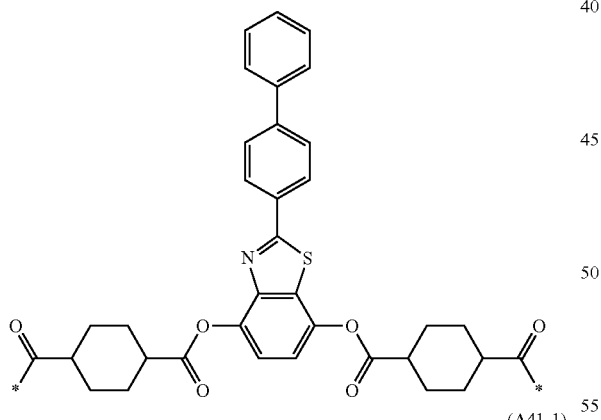
(A41-2)
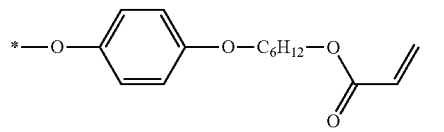
(A41-3)
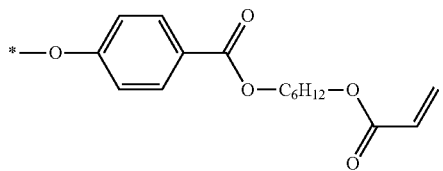
(A41-4)
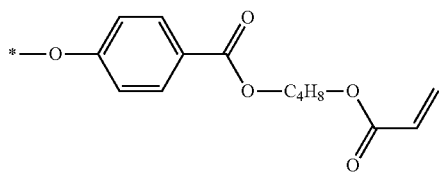
(A41-5)
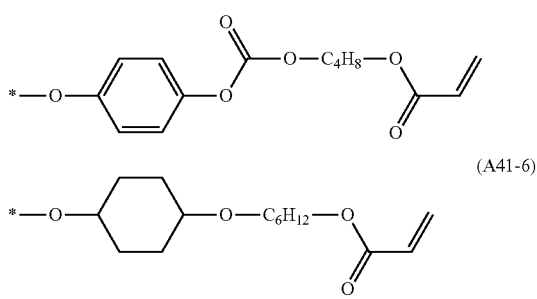
(A41-6)
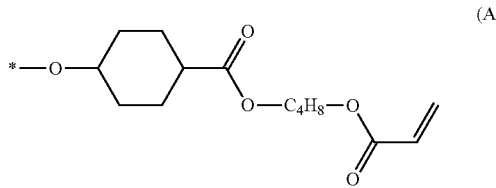
(A41-7)
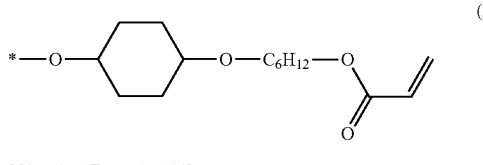
(A41-8)
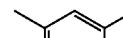
[Chemical Formula 144]
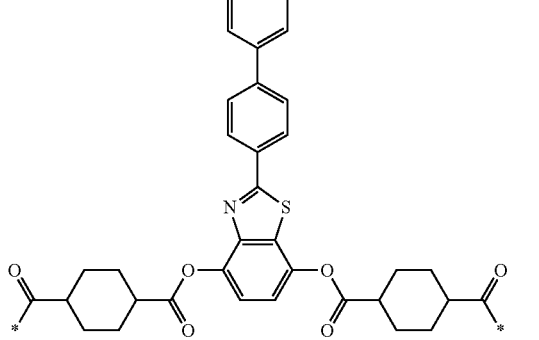
(A42-1)
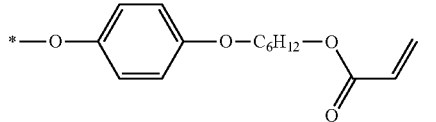

(A42-2) 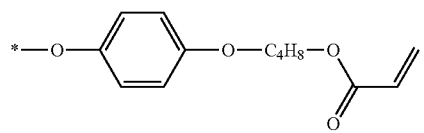
(A42-3) 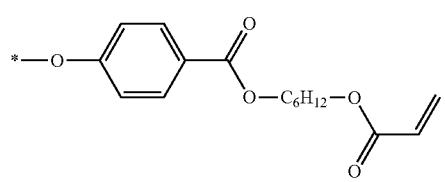
(A42-4) 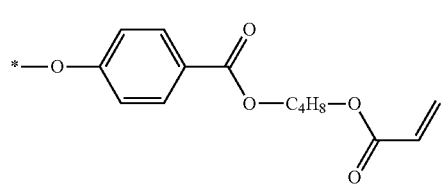
(A42-5) 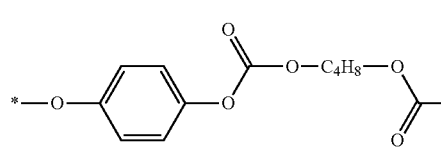
(A42-6) 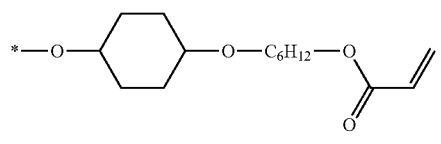
(A42-7) 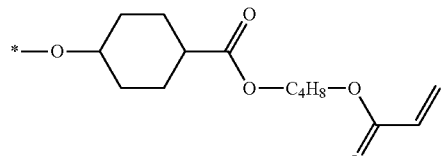
(A42-8) 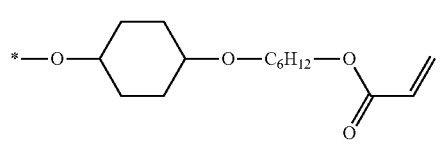
[Chemical Formula 145]
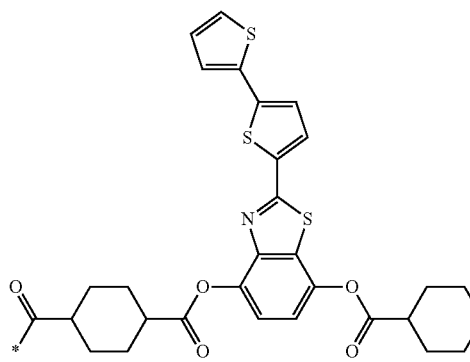
(A45-1) 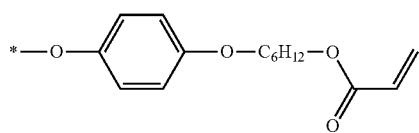
(A45-2) 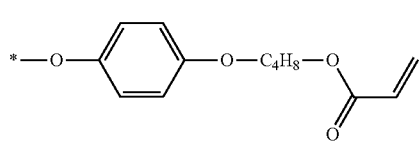
(A45-3) 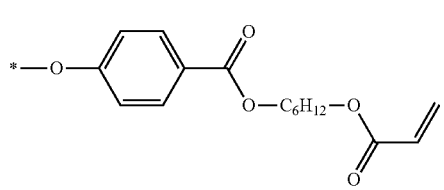
(A45-4) 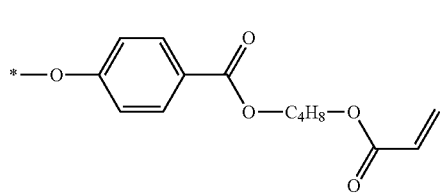
(A45-5) 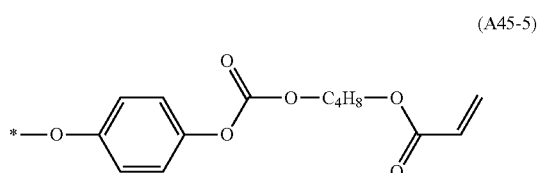
(A45-6) 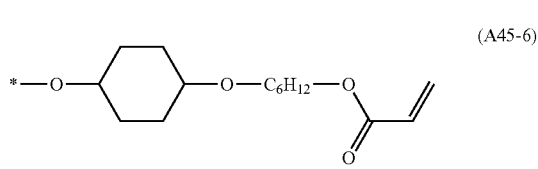
(A45-7) 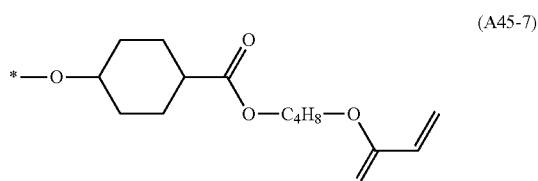
(A45-8) 

[Chemical Formula 146]
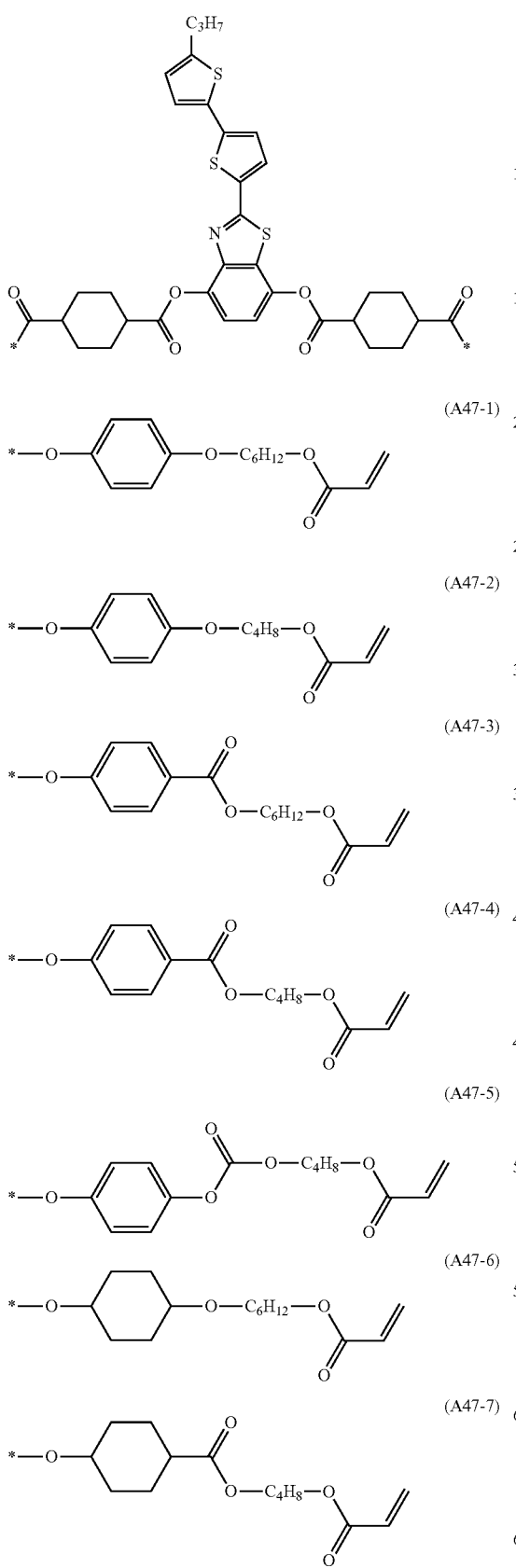
(A47-1)
(A47-2)
(A47-3)
(A47-4)
(A47-5)
(A47-6)
(A47-7)
(A47-8)
[Chemical Formula 147]
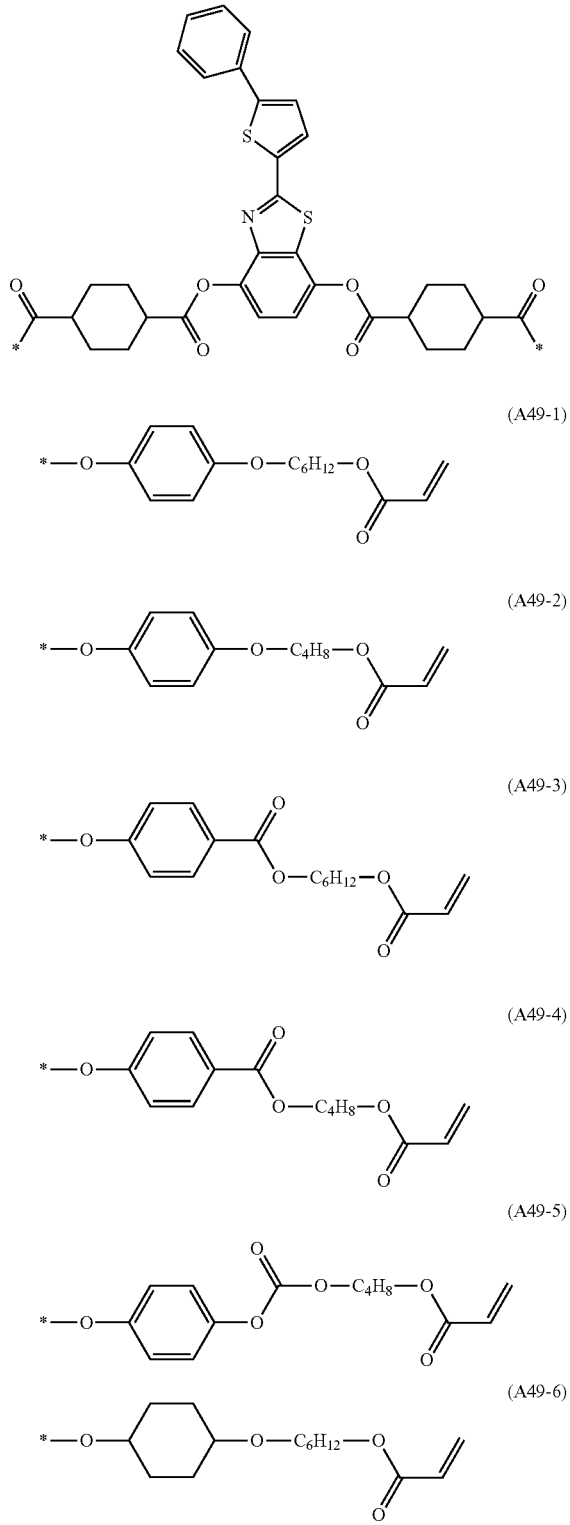
(A49-1)
(A49-2)
(A49-3)
(A49-4)
(A49-5)
(A49-6)

[Chemical Formula 148] (A49-7), (A49-8), (A53-1) through (A53-5)

[Chemical Formula 149] (A53-6), (A53-7), (A53-8), (A58-1) through (A58-5)

(A58-6)
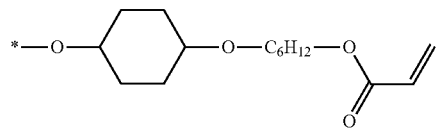
(A58-7)
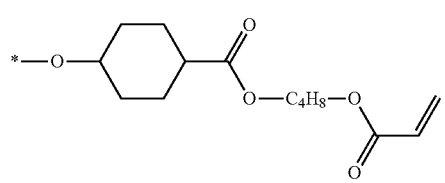
(A58-8)
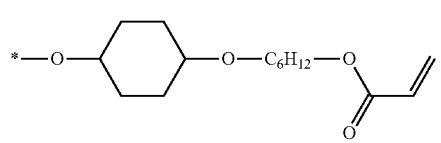
[Chemical Formula 150]
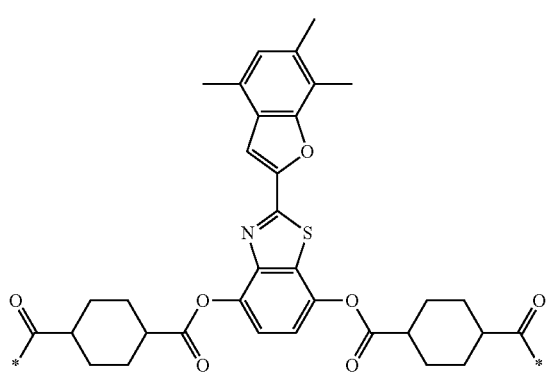
(A63-1)
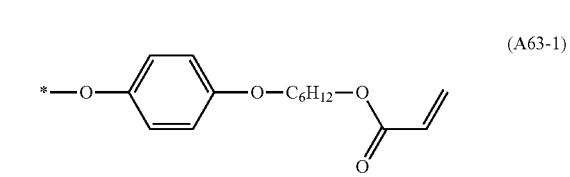
(A63-2)
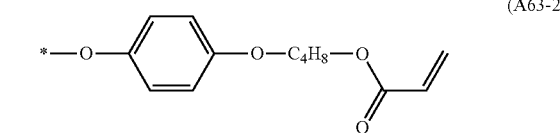
(A63-3)
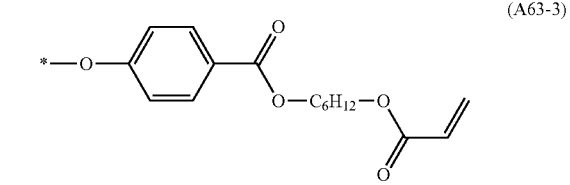
(A63-4)
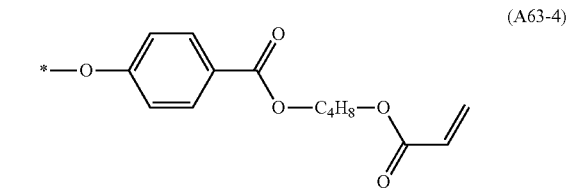
(A63-5)
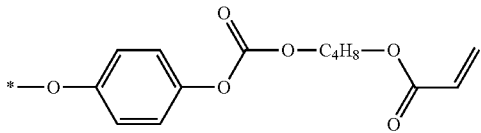
(A63-6)
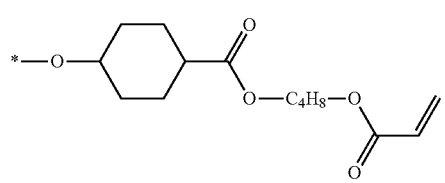
(A63-7)
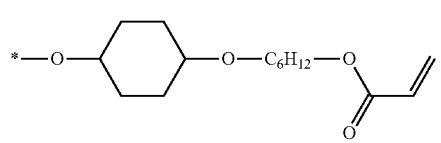
(A63-8)
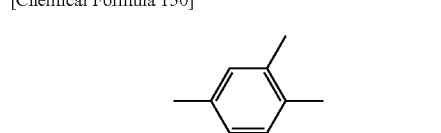
[Chemical Formula 151]
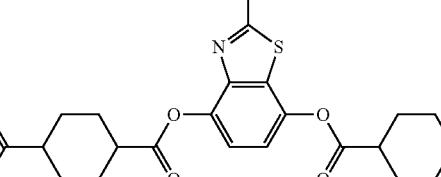
(A64-1)
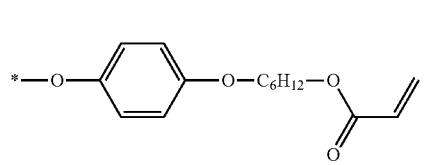
(A64-2)
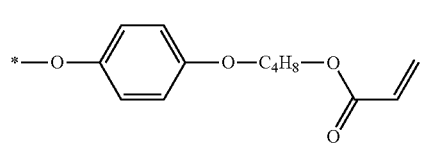
(A64-3)
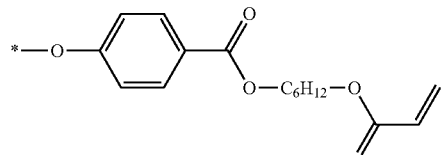

(A64-4) 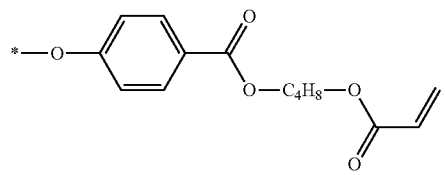
(A64-5) 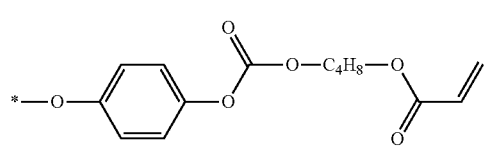
(A64-6) 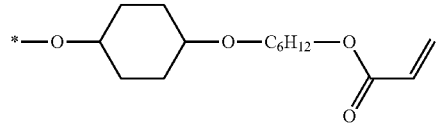
(A64-7) 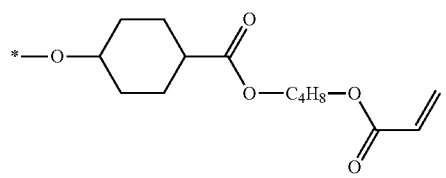
(A64-8) 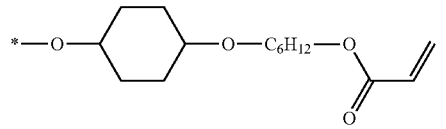
[Chemical Formula 152]
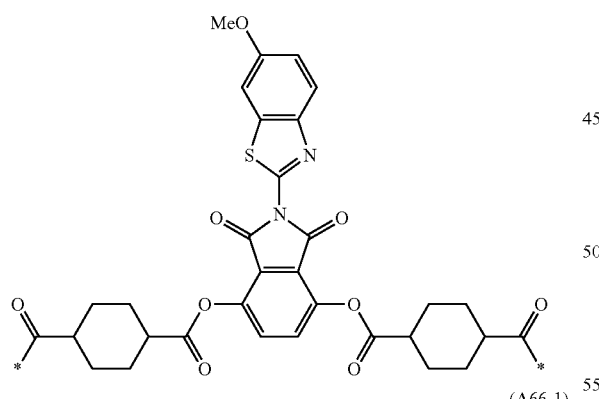
(A66-1) 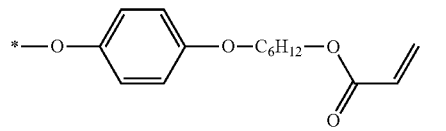
(A66-2) 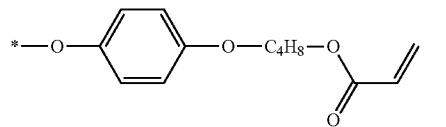
(A66-3) 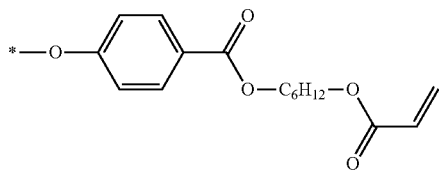
(A66-4) 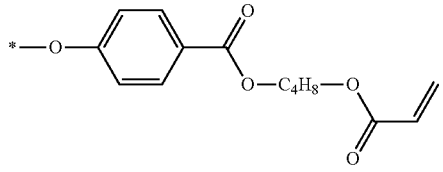
(A66-5) 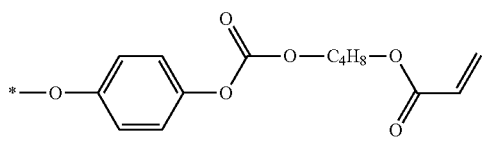
(A66-6) 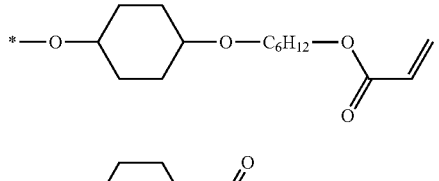
(A66-7) 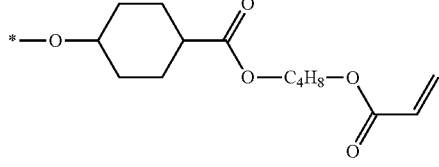
(A66-8) 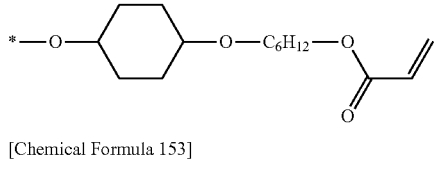
[Chemical Formula 153]
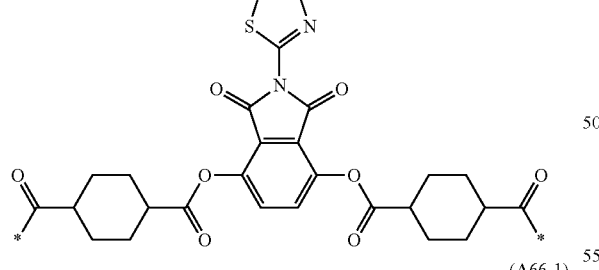
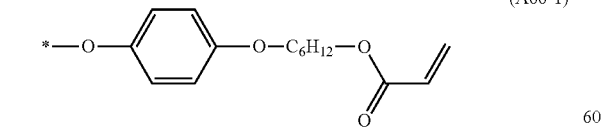
(A67-1) 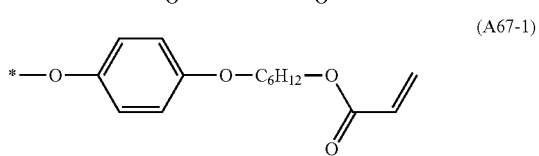

(A67-2) 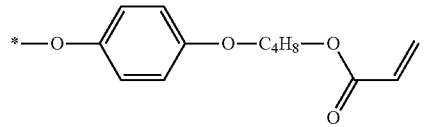
(A67-3) 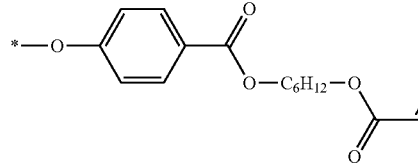
(A67-4) 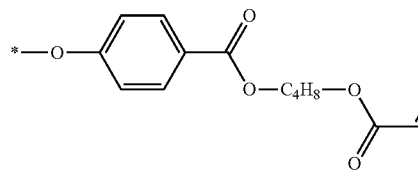
(A67-5) 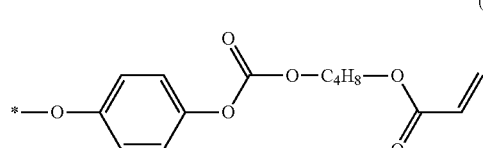
(A67-6) 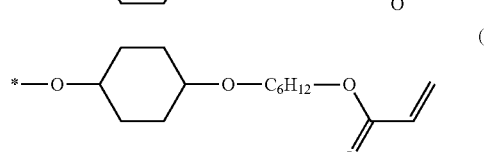
(A67-7) 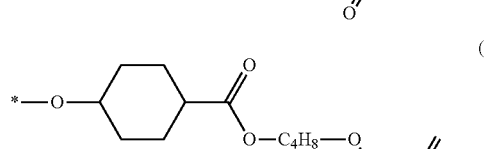
(A67-8) 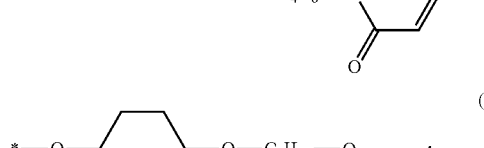
[Chemical Formula 154]
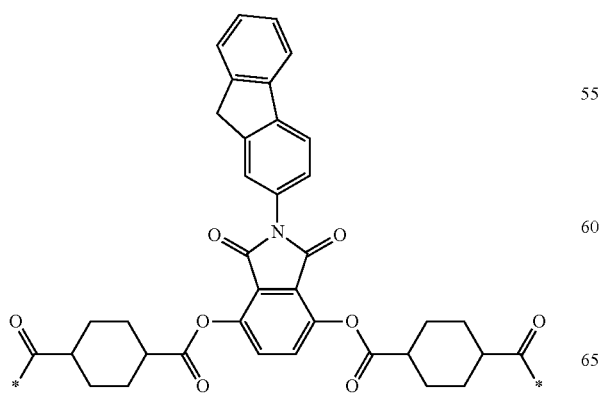
(A68-1) 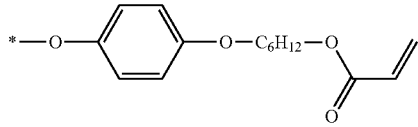
(A68-2) 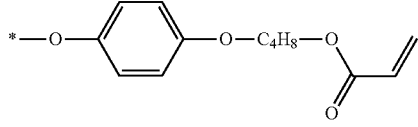
(A68-3) 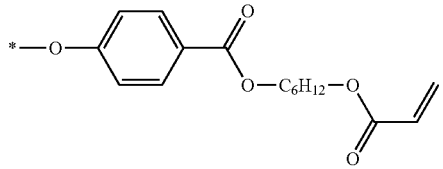
(A68-4) 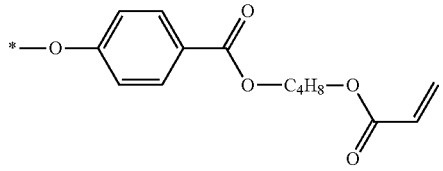
(A68-5) 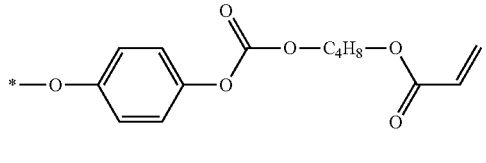
(A68-6) 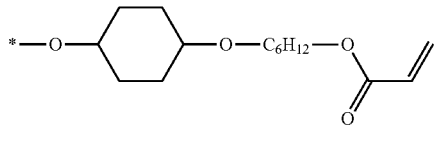
(A68-7) 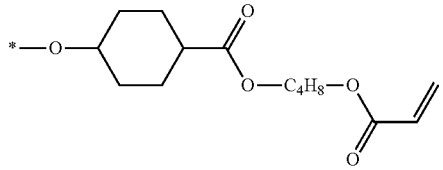
(A66-8) 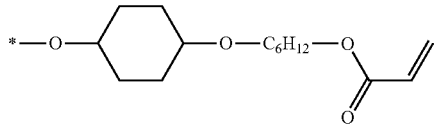

[Chemical Formula 155]
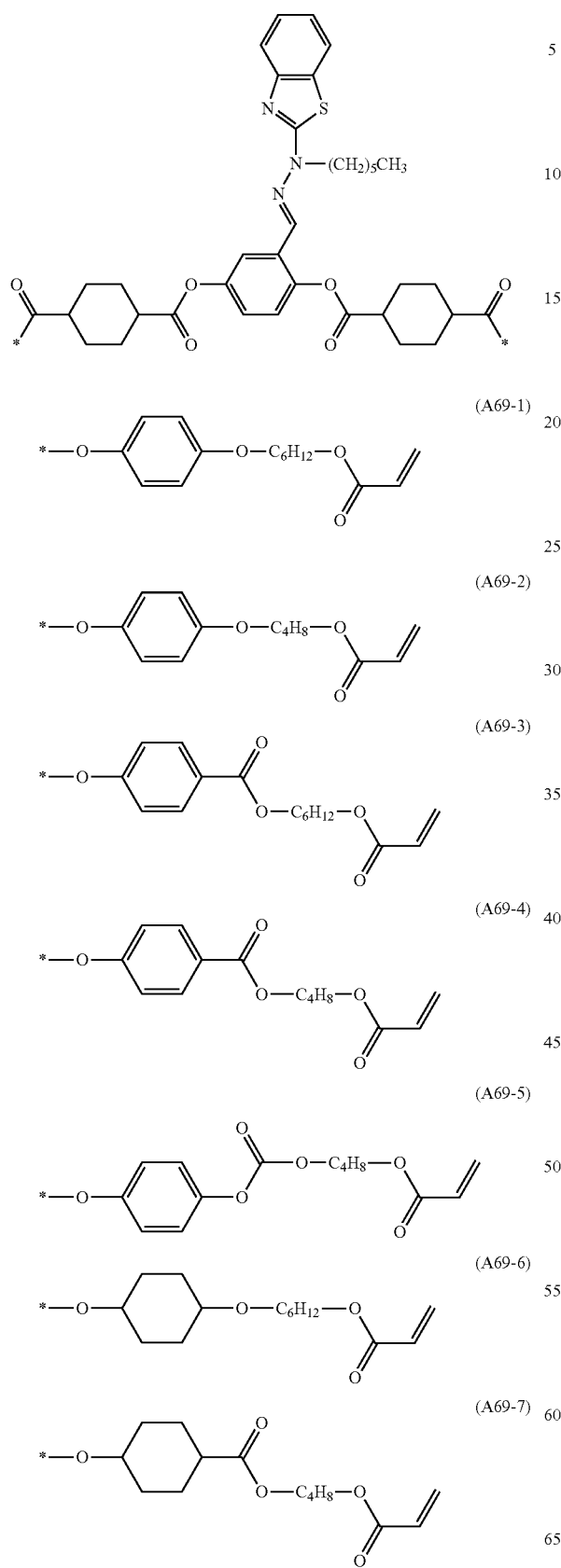
(A69-1)
(A69-2)
(A69-3)
(A69-4)
(A69-5)
(A69-6)
(A69-7)
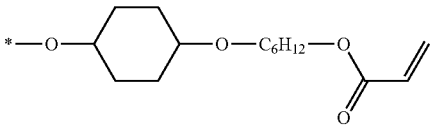
(A69-8)
[Chemical Formula 156]
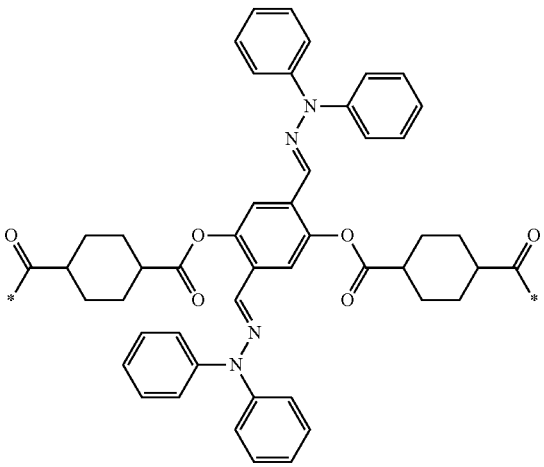
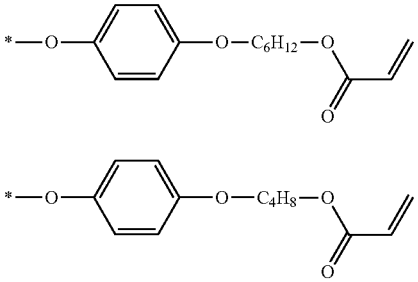
(A70-1)
(A70-2)
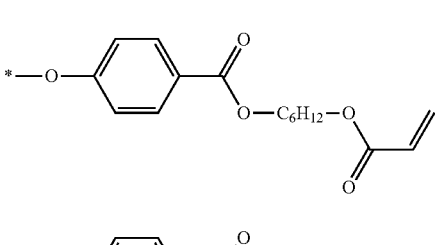
(A70-3)
(A70-4)
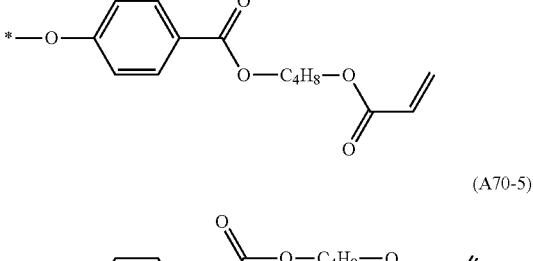
(A70-5)
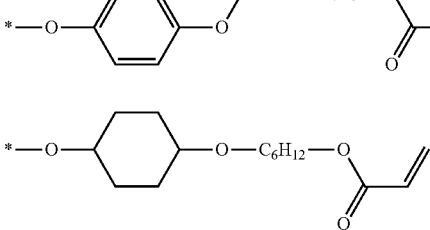
(A70-6)

(A70-7) 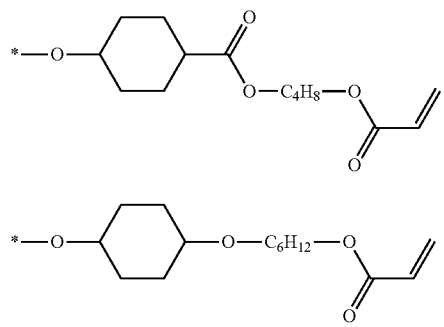
(A70-8)
[Chemical Formula 157]
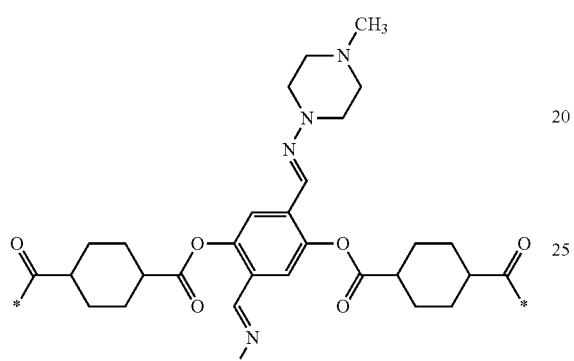
(A71-1) 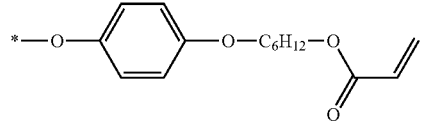
(A71-2) 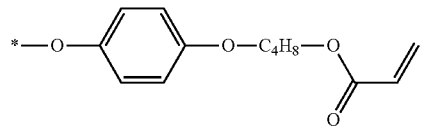
(A71-3) 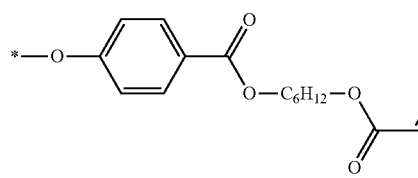
(A71-4) 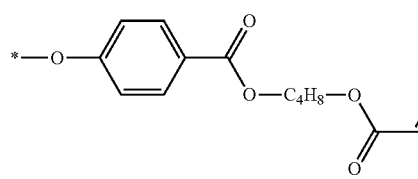
(A71-5) 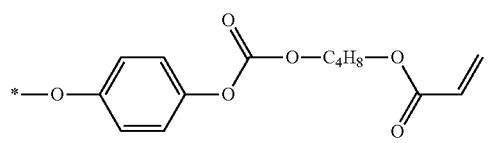
(A71-6) 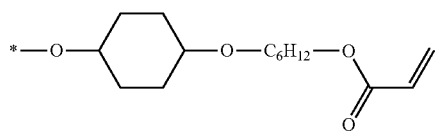
(A71-7) 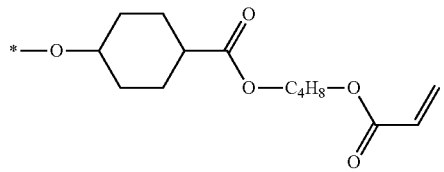
(A71-8) 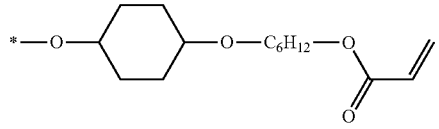
[Chemical Formula 158]
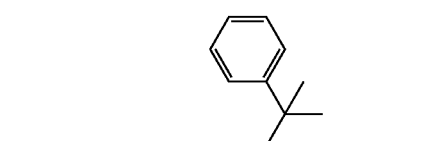
(A80-1) 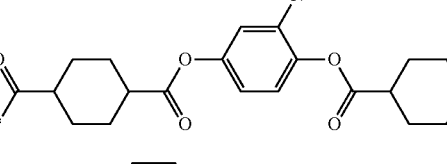
(A80-2) 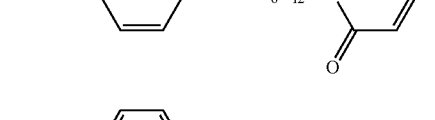
(A80-3) 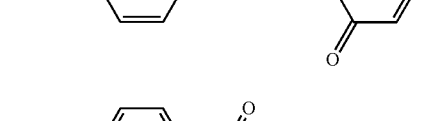
(A80-4) 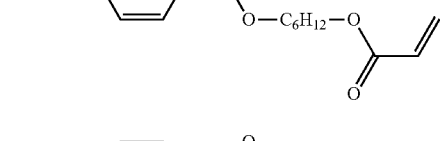
(A80-5) 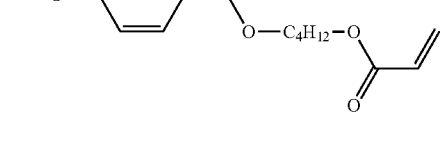

-continued
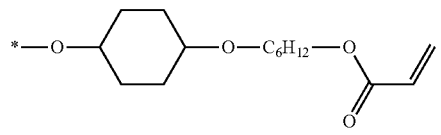 (A80-6)
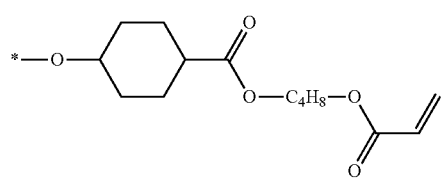 (A80-7)
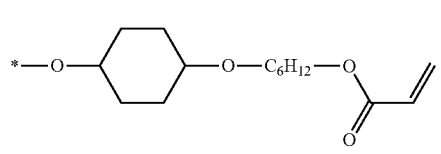 (A80-8)
[Chemical Formula 159]
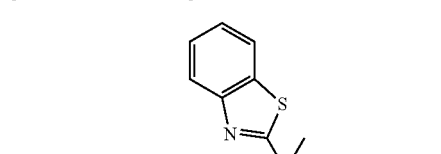
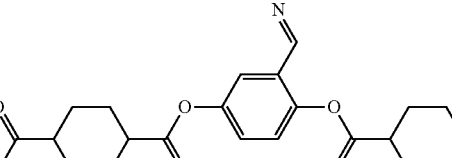 (A81-1)
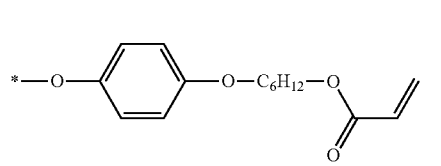 (A812)
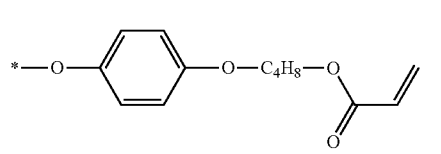 (A81-3)
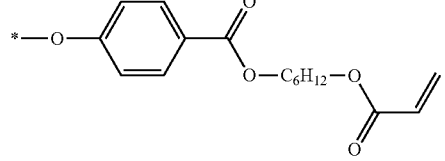 (A81-4)
-continued
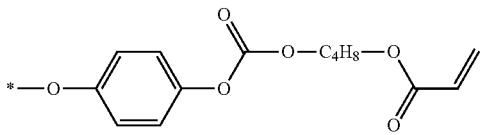 (A81-5)
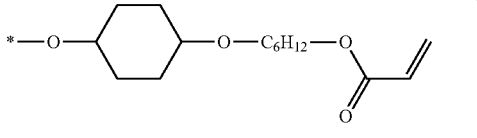 (A81-6)
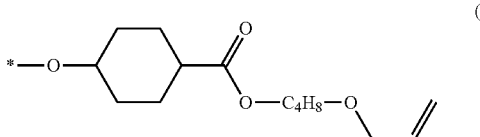 (A81-7)
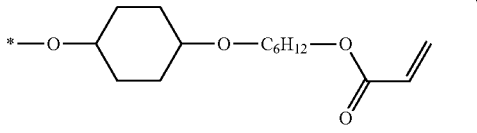 (A81-8)
[Chemical Formula 160]
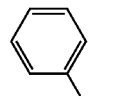
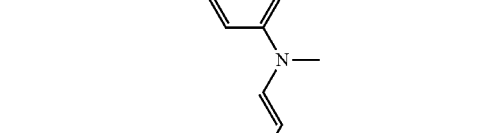
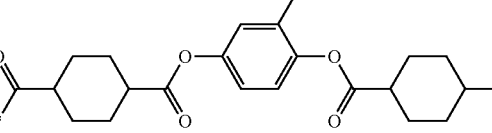 (A82-1)
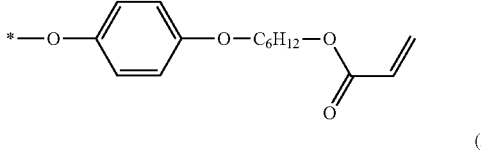 (A82-2)
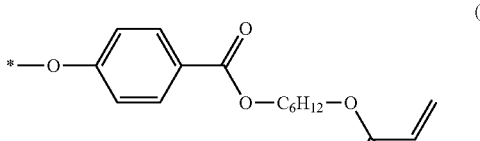 (A82-3)
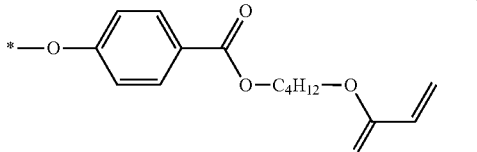 (A82-4)

-continued
(A82-5) 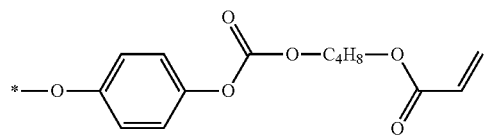
(A82-6) 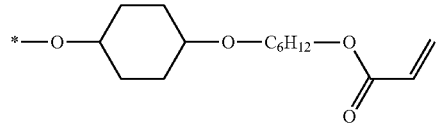
(A82-7) 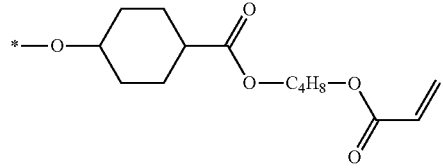
(A82-8) 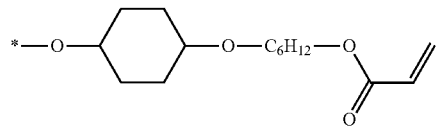
[Chemical Formula 161]
(A83-1) 
(A83-2) 
(A83-3) 
(A83-4) 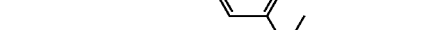
-continued
(A83-5)
(A83-6)
(A83-7)
(A83-8)
[Chemical Formula 162]
(A84-1)
(A84-2)
(A84-3)
(A84-4)

(A84-5)
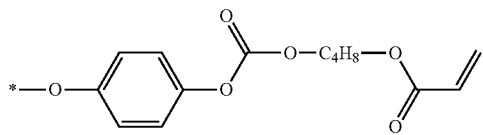

(A84-6)
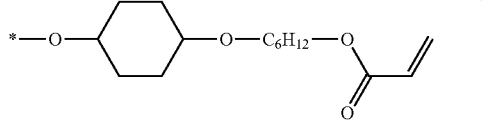

(A84-7)
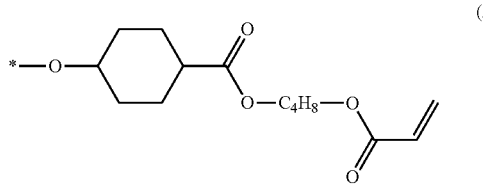

(A84-8)
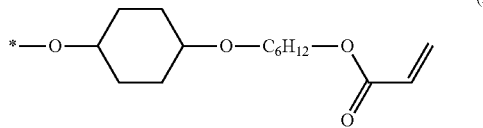

[Chemical Formula 163]

(A85-1)

(A85-2)
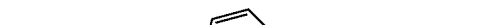

(A85-3)

(A85-4)
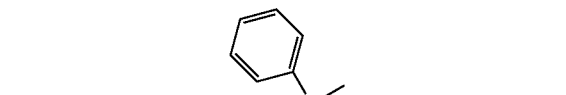

(A85-5)
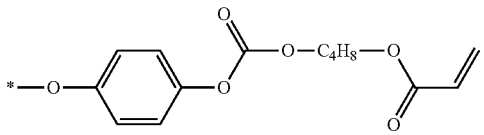

(A85-6)
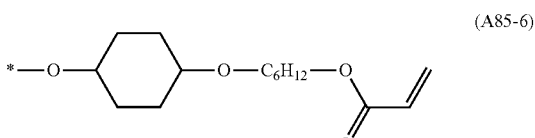

(A85-7)
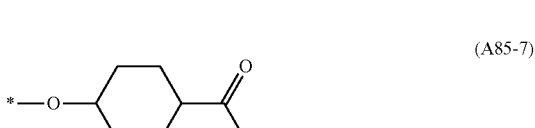

(A85-8)

In the present invention, a maximum absorption wavelength ($\lambda_{max}$) of the polymerizable liquid crystal compound is preferably 300 to 400 nm, more preferably 315 to 385 nm, further more preferably 320 to 380 nm. When the maximum absorption wavelength ($\lambda_{max}$) of the polymerizable liquid crystal compound is not smaller than the aforementioned minimum value, a retardation film comprising a polymer of a liquid crystal composition in oriented state tends to show reverse wavelength dispersibility. When the maximum absorption wavelength ($\lambda_{max}$) of the polymerizable liquid crystal compound is not greater than the aforementioned maximum value, absorption in visible light region is suppressed, and thus coloration of a film can be prevented.

Method for production of the polymerizable liquid crystal Compound is not specifically limited, and can be produced by suitable combination of publicly-known organic synthesis reactions (e.g., a condensation reaction, an esterification reaction, a Williamson reaction, an Ullmann reaction, a Wittig reaction, a Schiff base producing reaction, a benzylation reaction, a Sonogashira reaction, a Suzuki-Miyaura reaction, a Negishi reaction, a Kumada reaction, a Hiyama reaction, a Buchwald-Hartwig reaction, a Friedel-Crafts reaction, a Heck reaction, and an aldol reaction) as described in, for example, Methoden der Organischen Chemie, Organic Reactions, Organic Syntheses, Comprehensive Organic Synthesis, and Encyclopedia of Experimental Chemistry (Shin Jikken Kagaku Koza) according to the structure of the desired polymerizable liquid crystal compound.

Specifically, for example, a polymerizable liquid crystal compound represented by the following formula (A-1), which is one of the above-mentioned polymerizable liquid crystal compound:

[Chemical Formula 164]

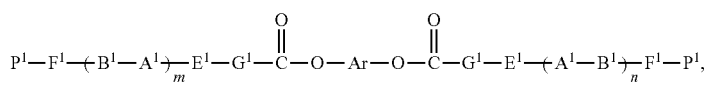

(A-1)

wherein when m=n in the formula, can be produced by an esterification reaction of an alcohol compound (B) represented by formula (B):

[Chemical Formula 165]

(B)

with a carboxylic acid compound (C) represented by formula (C):

[Chemical Formula 166]

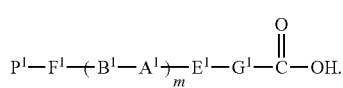

(C)

Then, Ar, $A^1$, $B^1$, $E^1$, $F^1$, $G^1$, $P^1$, m, and n in the formula (A-1), (B), and (C) are the same as defined above.

The alcohol compound (B) only have to be a compound in which 2 hydroxyl groups are bonded to an aromatic group Ar. The aromatic group Ar is the same as defined above, and for example, examples of the Ar include compounds in the formulae (Ar-1) to (Ar-20) in which two * portions are hydroxyl groups.

The carboxylic acid (C) can be used alone, or 2 or more of the carboxylic acids (C) can be used in combination. When 2 or more carboxylic acid compounds (C) are used, a polymerizable liquid crystal compound in which a structure of one half portion is different from that of the other half portion viewed from Ar as the central point can be obtained. Examples of the carboxylic acid compound (C) include compounds represented by the following formula (R-1) to formula (R-104).

n in formula (R-1) to formula (R-104) represents an integer of 1 to 12. Further, the cyclohexane ring is preferably a trans isomer.

[Chemical Formula 167]

(R-1)

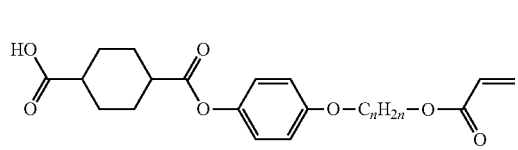

(R-2)

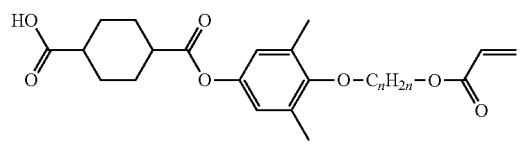

(R-3)

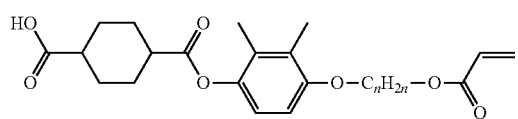

(R-4)

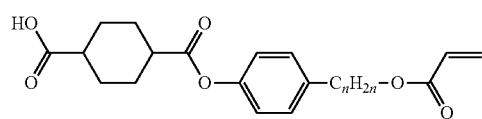

(R-5)

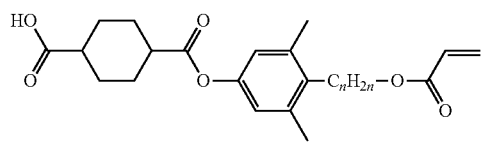

(R-6)

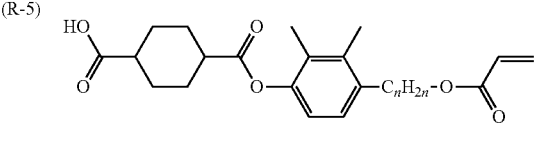

(R-7)

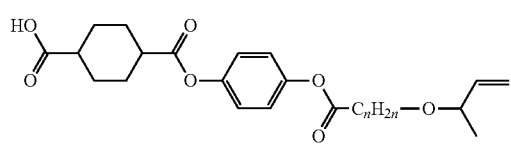

(R-8)

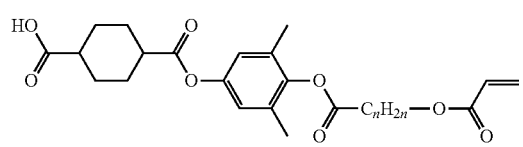

(R-9)

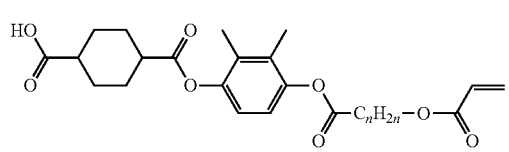

(R-10)

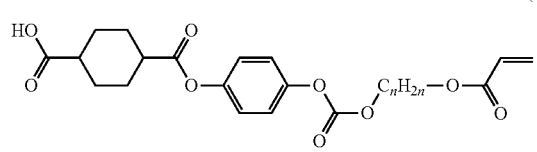

-continued
(R-11)
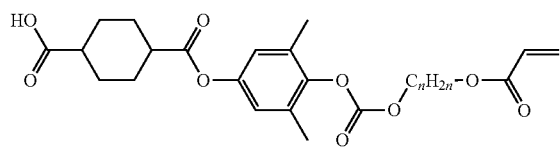
(R-12)
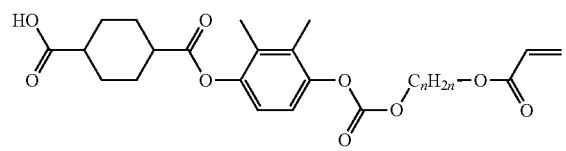
(R-13)
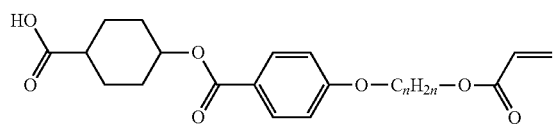
(R-14)
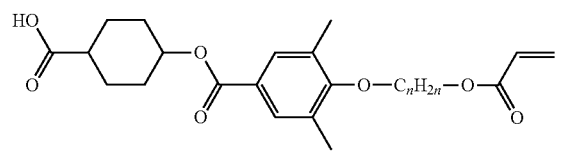
(R-15)
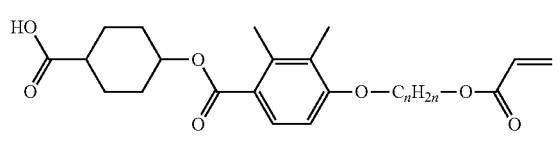
(R-16)
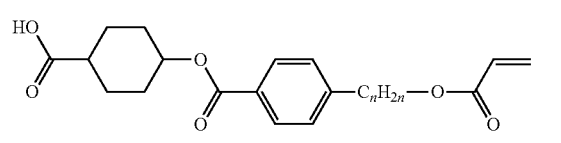
(R-17)
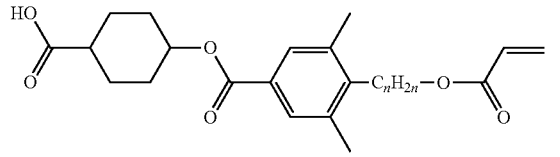
(R-18)
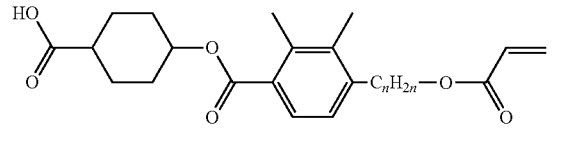
(R-19)
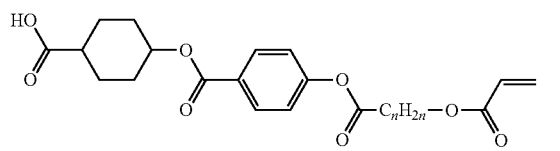
(R-20)
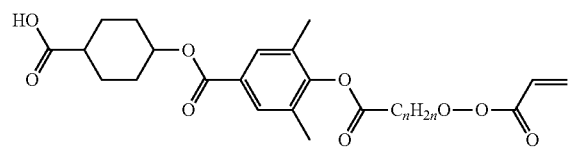
(R-21)
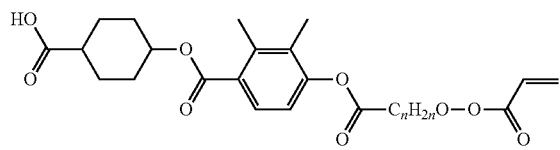
(R-22)
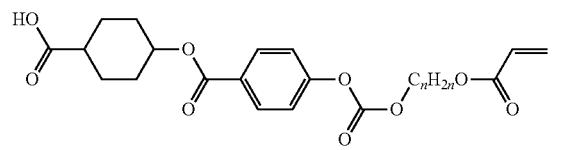
(R-23)
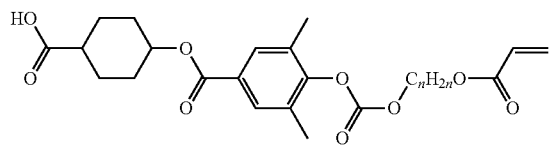
(R-24)
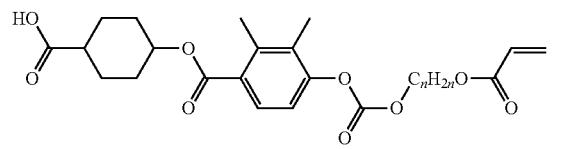
[Chemical Formula 168]
(R-25)
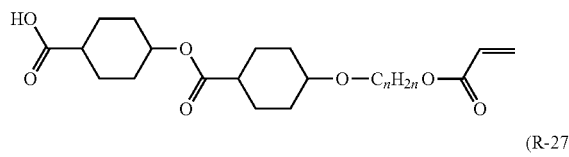
(R-26)
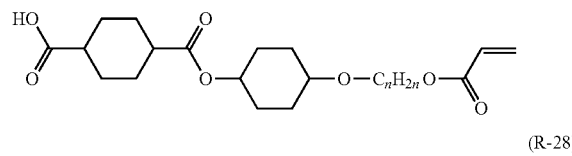
(R-27)
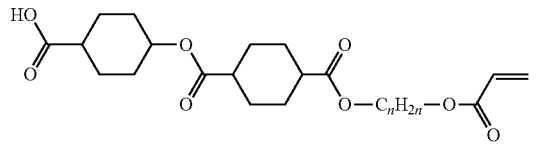
(R-28)
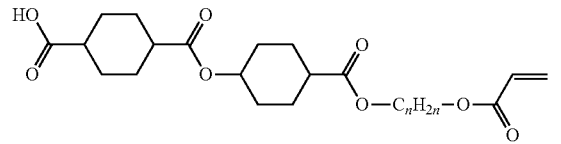

-continued
(R-29) 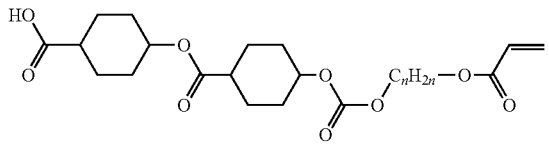
(R-30) 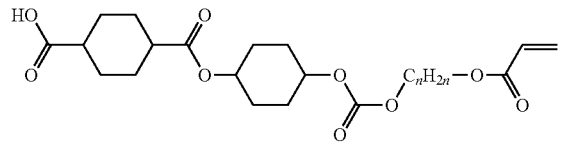
(R-31) 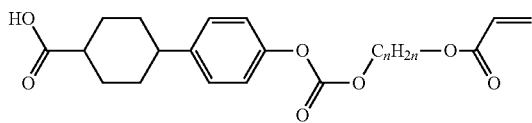
(R-32) 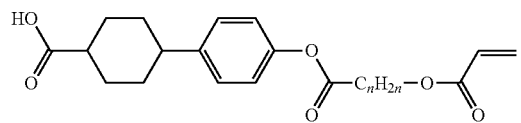
(R-33) 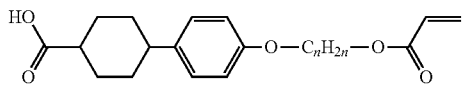
(R-34) 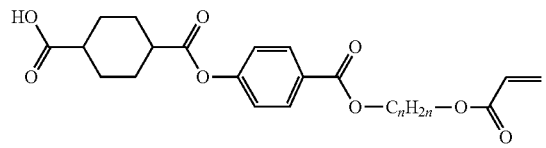
(R-35) 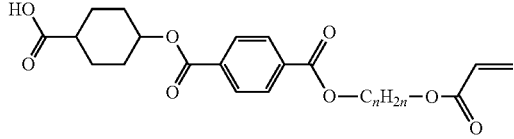
(R-36) 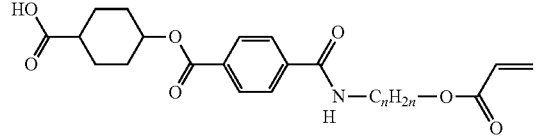
(R-37) 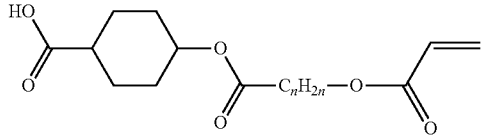
(R-38) 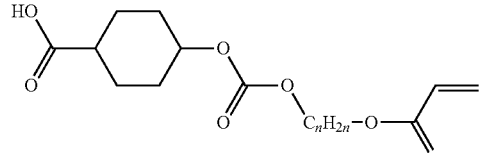
(R-39) 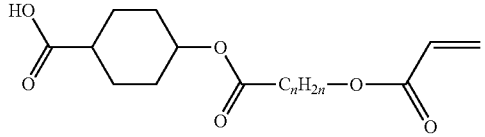
(R-40) 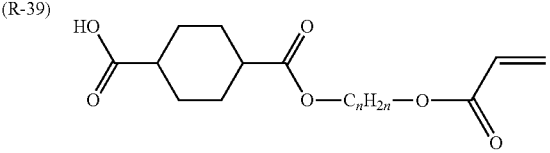
[Chemical Formula 169]
(R-41) 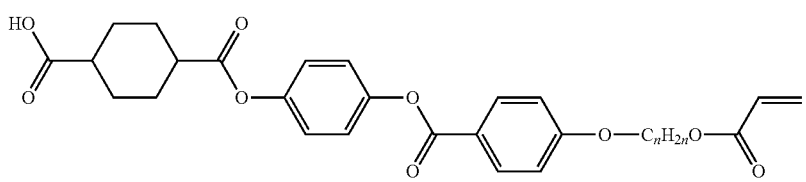
(R-42) 
(R-43) 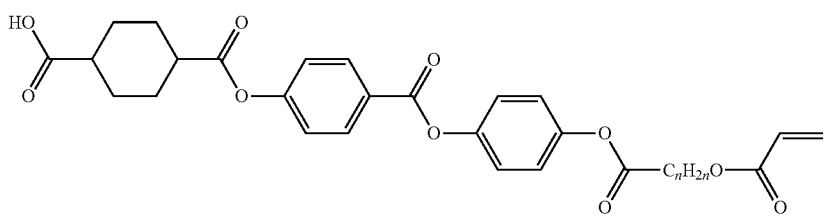

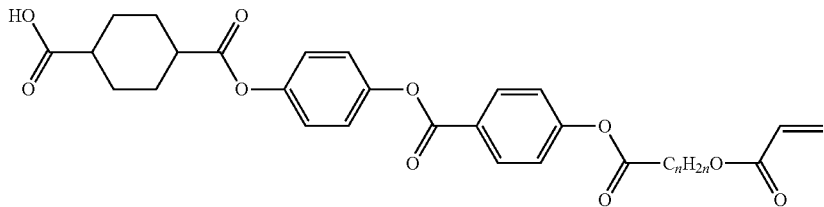
(R-44)
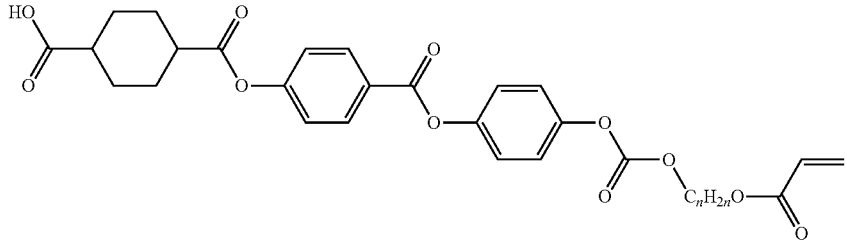
(R-45)
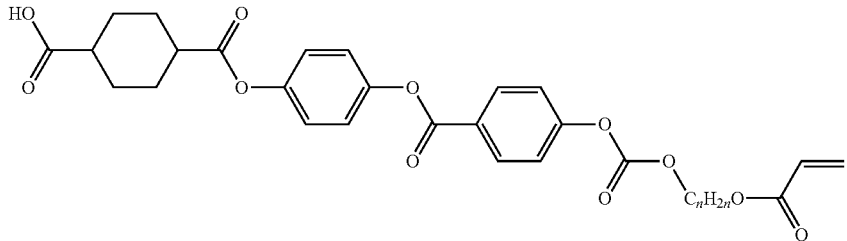
(R-46)
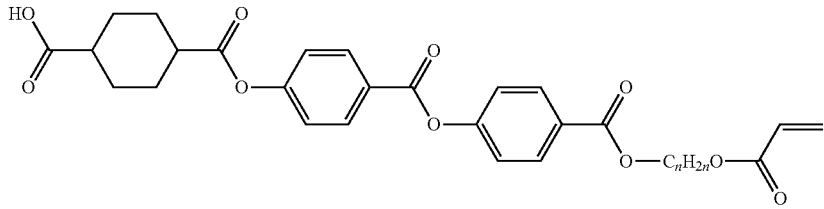
(R-47)
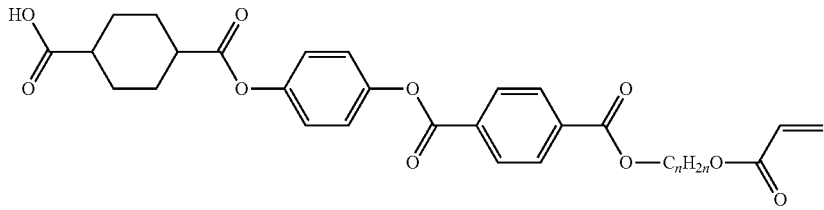
(R-48)
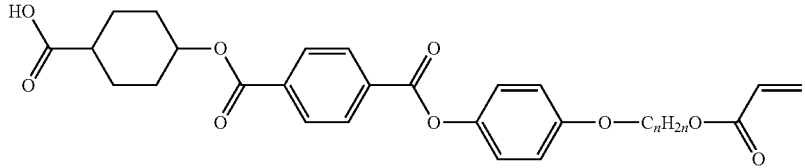
(R-49)
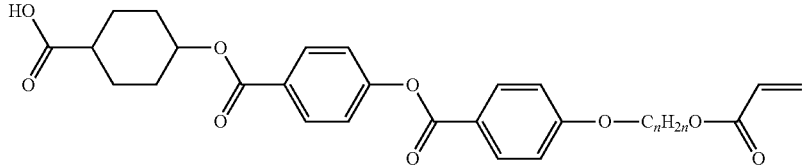
(R-50)

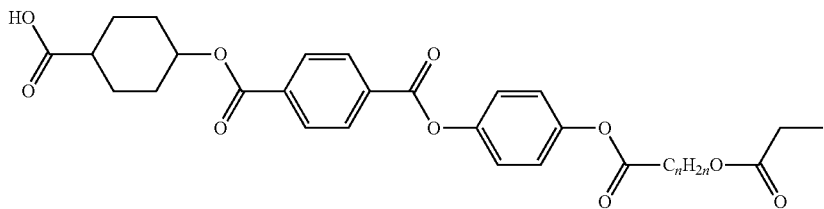
(R-51)
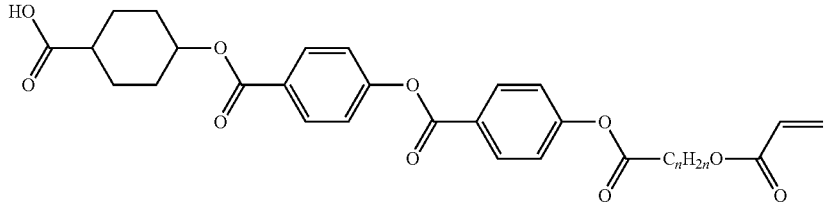
(R-52)
[Chemical Formula 170]
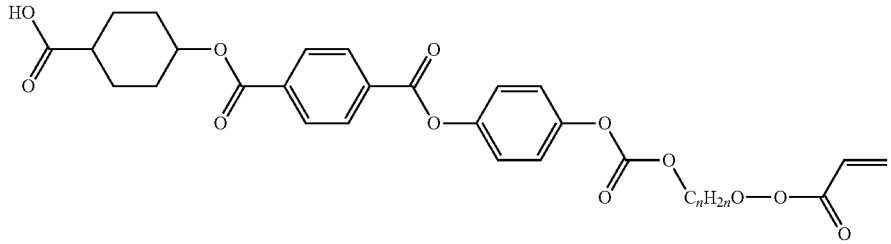
(R-53)
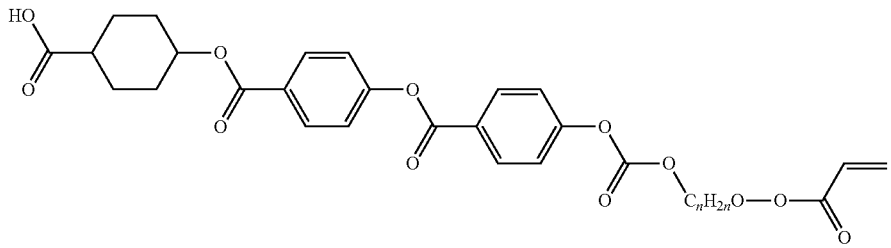
(R-54)
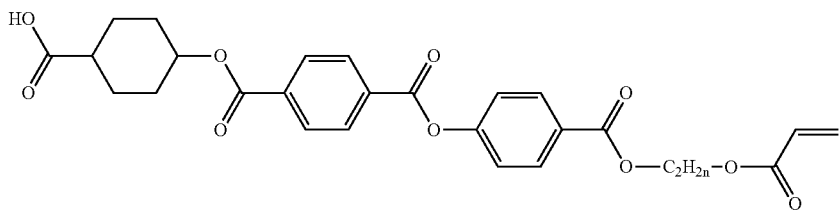
(R-55)
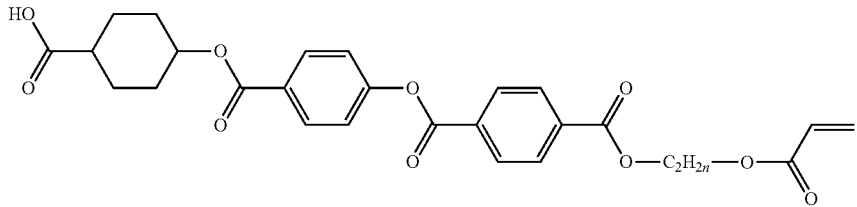
(R-56)
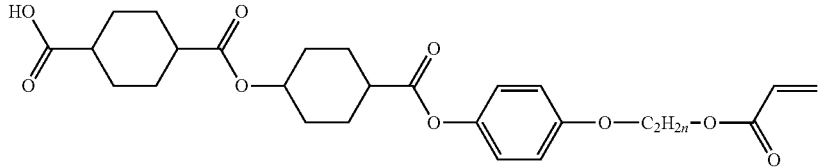
(R-57)

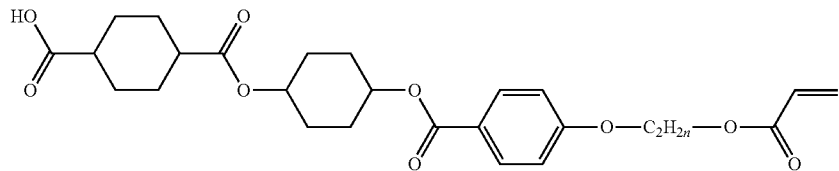
(R-58)
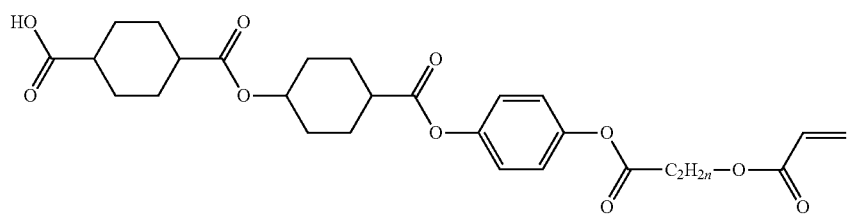
(R-59)
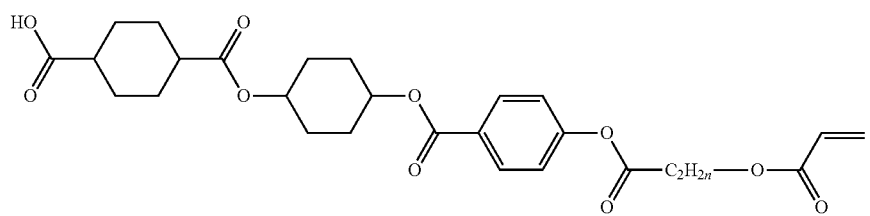
(R-60)
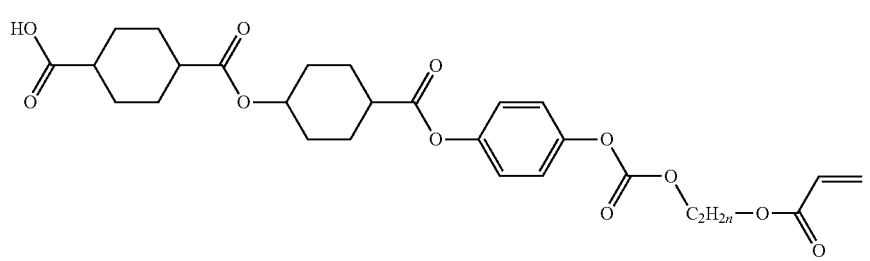
(R-61)
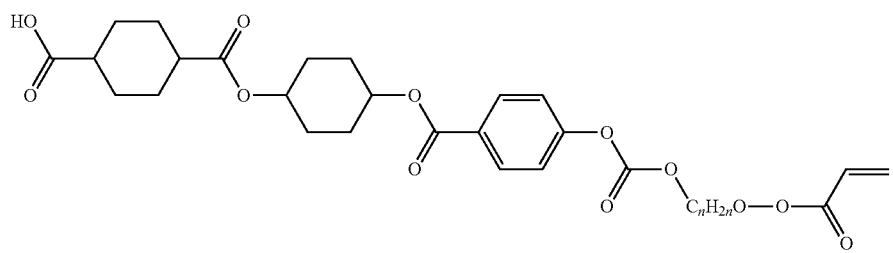
(R-62)
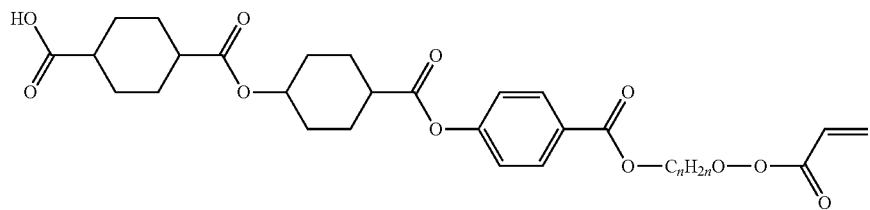
(R-63)
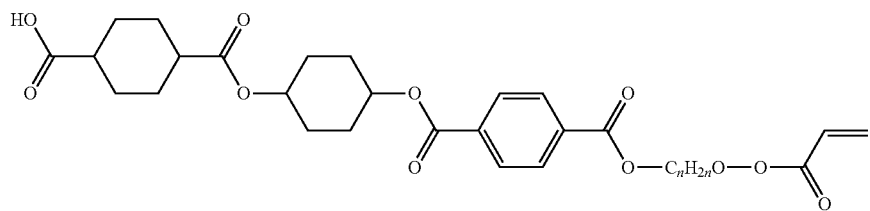
(R-64)

[Chemical Formula 171]
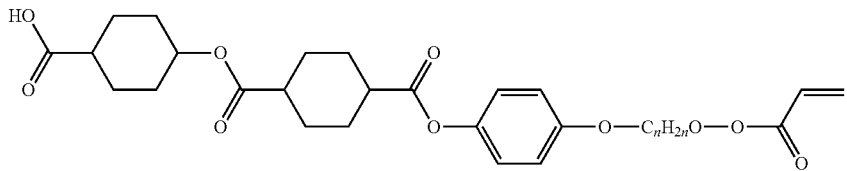 (R-65)
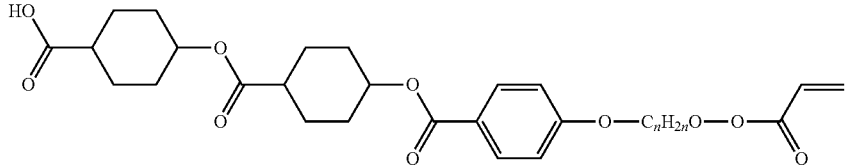 (R-66)
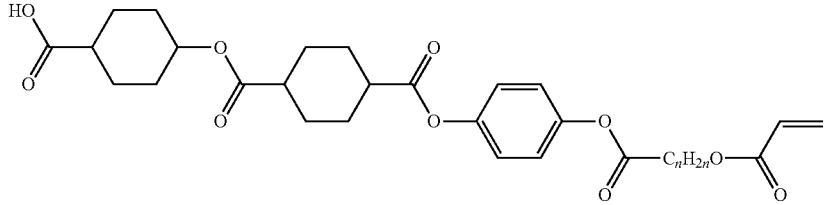 (R-67)
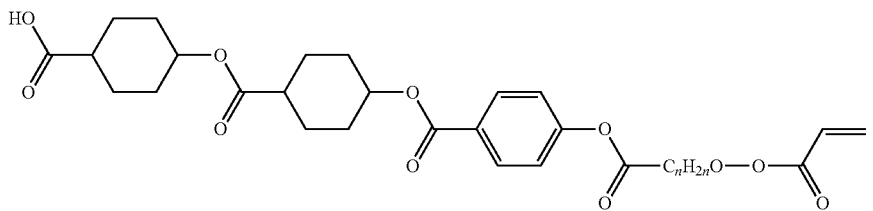 (R-68)
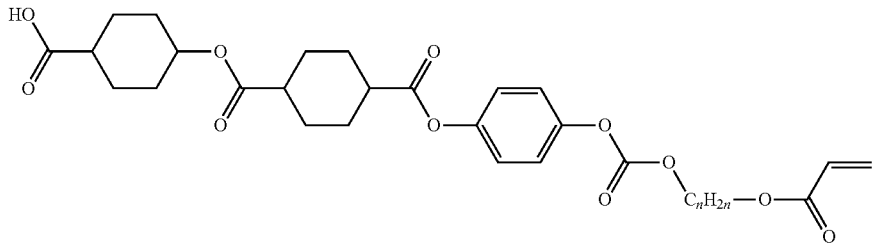 (R-69)
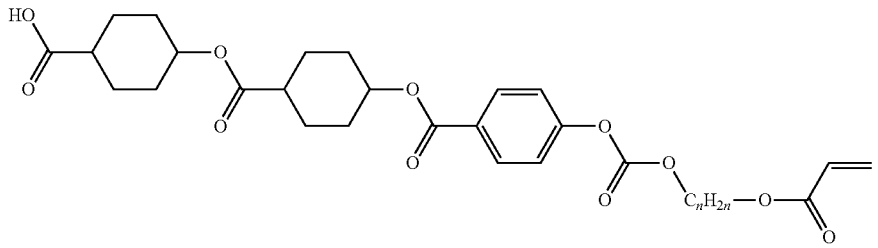 (R-70)
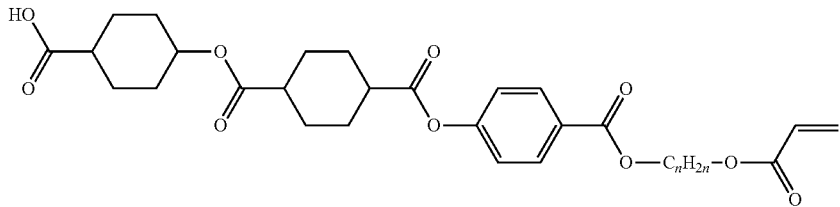 (R-71)

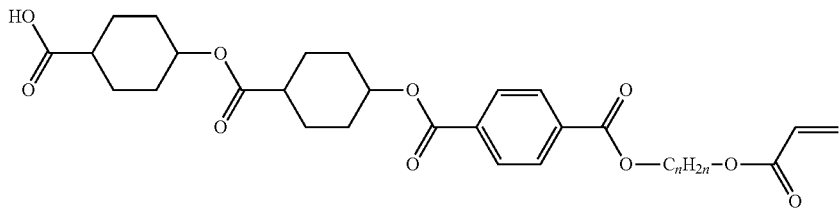
(R-72)
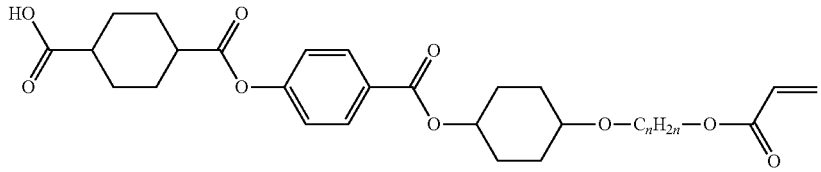
(R-73)
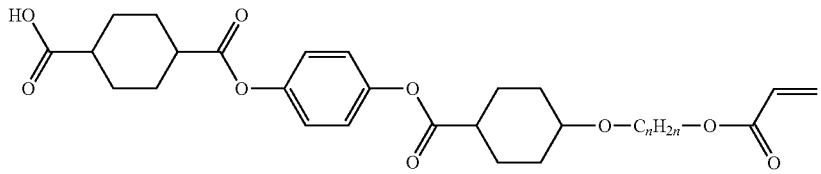
(R-74)
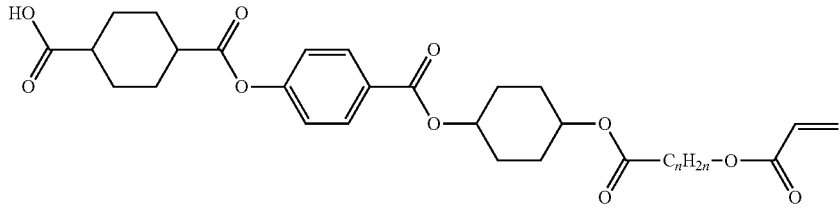
(R-75)
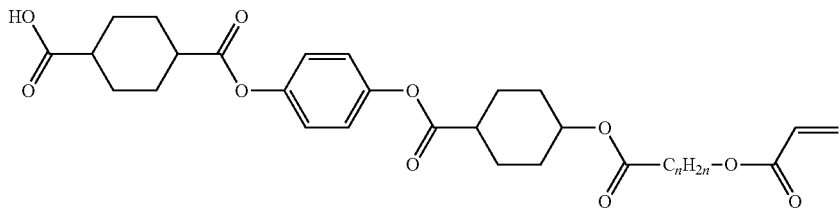
(R-76)
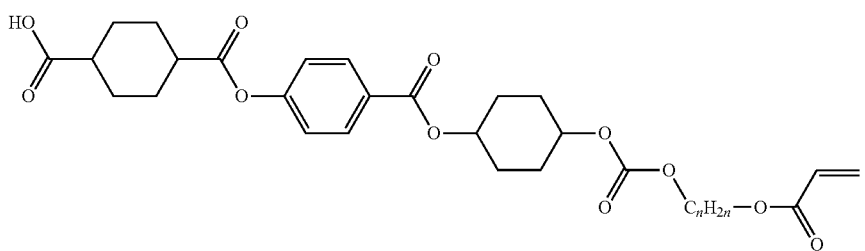
(R-77)
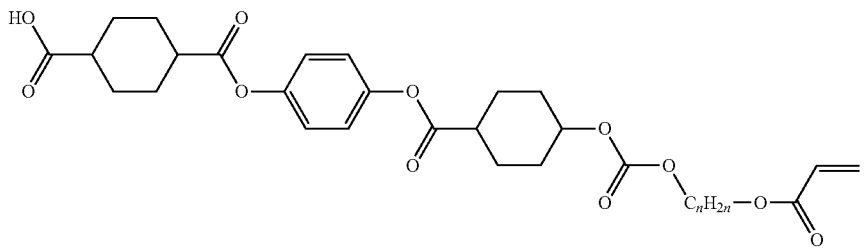
(R-78)

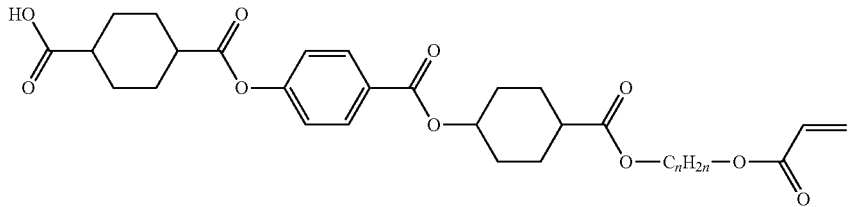
(R-79)
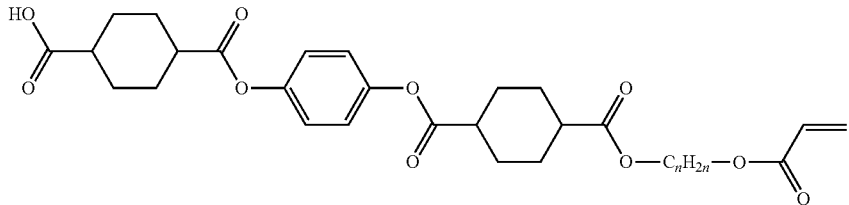
(R-80)
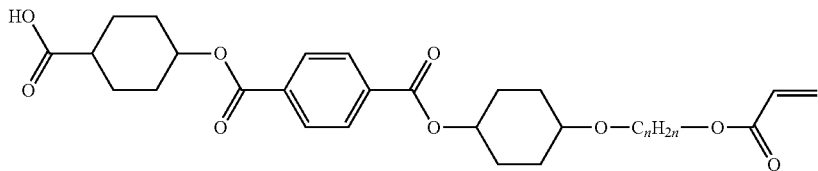
(R-81)
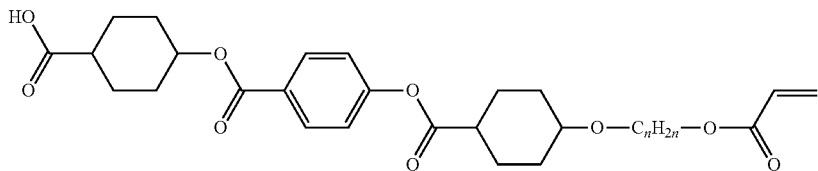
(R-82)
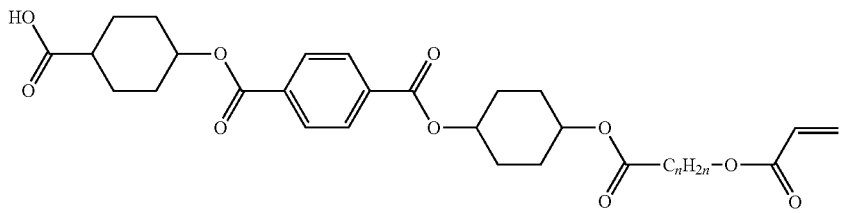
(R-83)
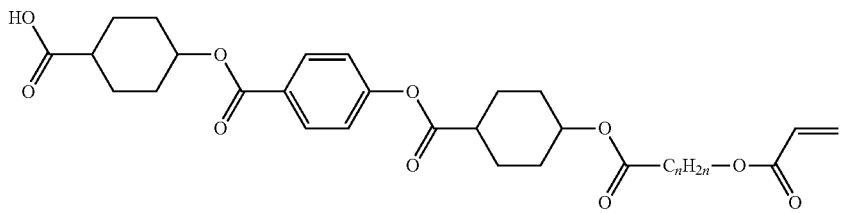
(R-84)
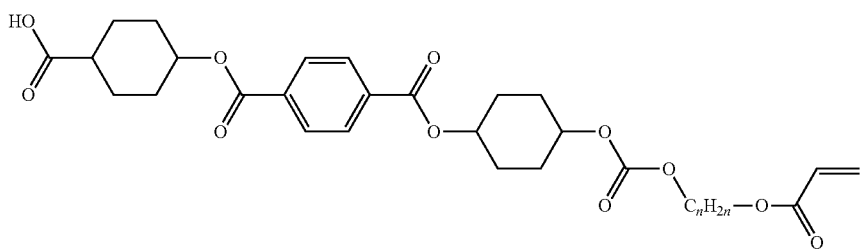
(R-85)

-continued
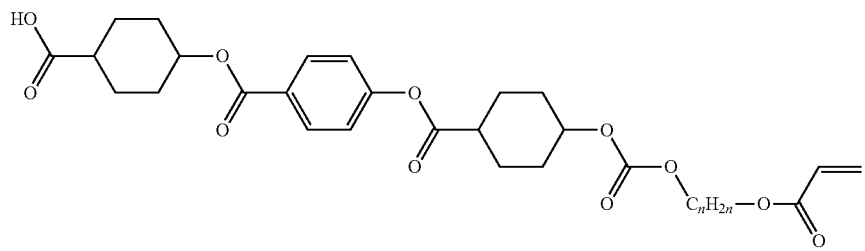 (R-86)
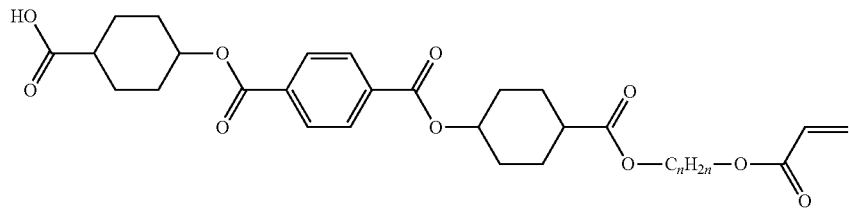 (R-87)
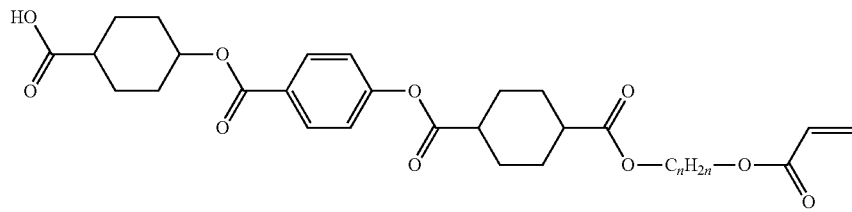 (R-88)
[Chemical Formula 173]
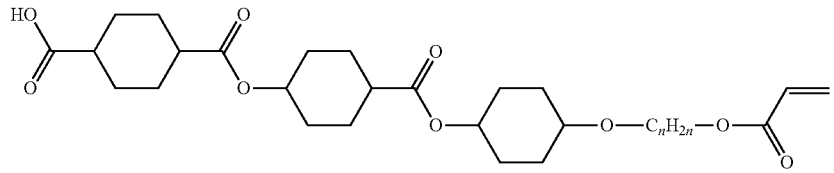 (R-89)
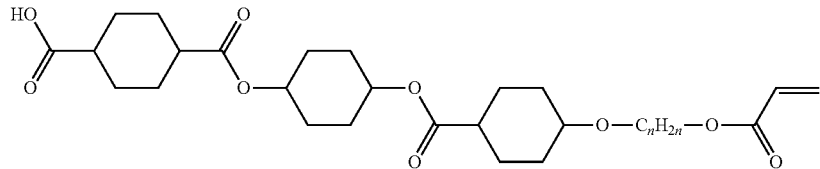 (R-90)
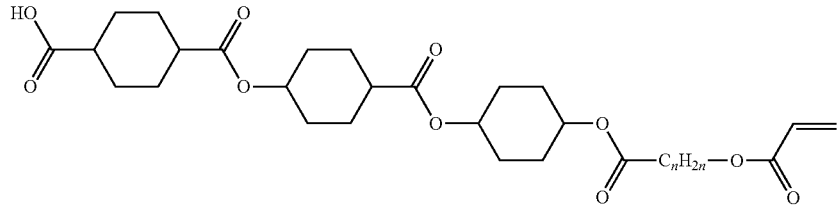 (R-91)
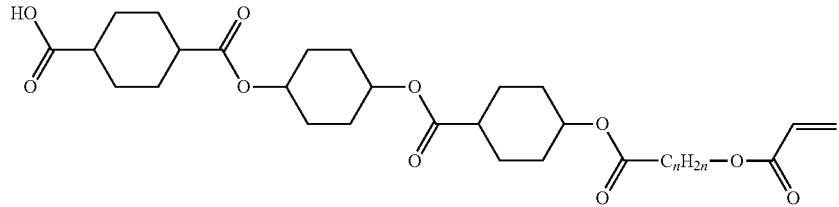 (R-92)

-continued
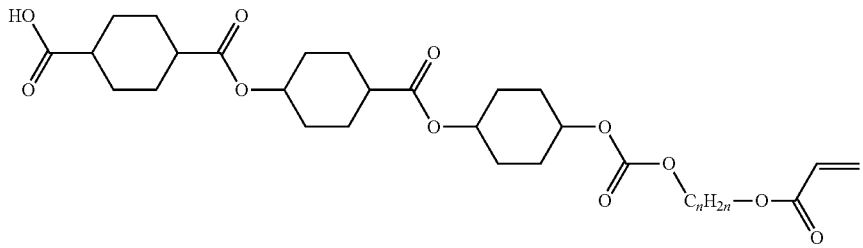
(R-93)
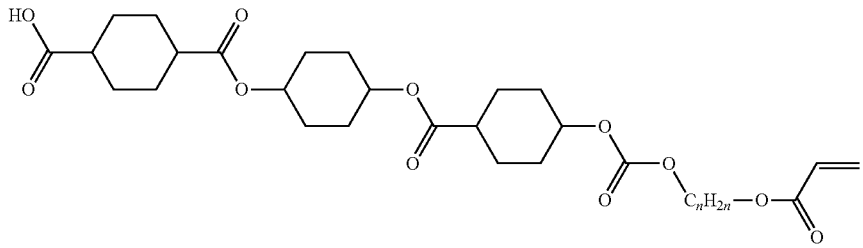
(R-94)
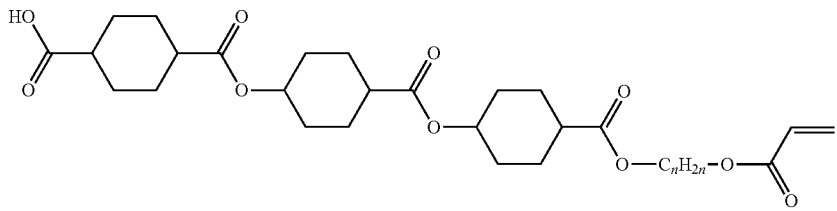
(R-95)
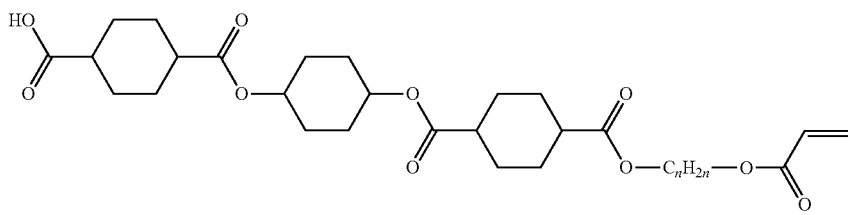
(R-96)
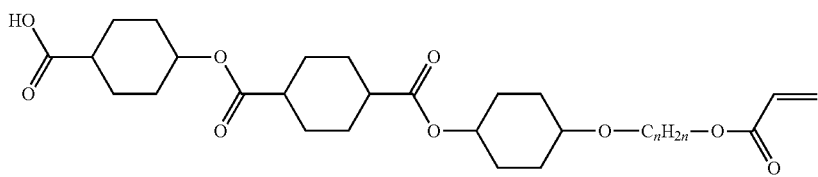
(R-97)
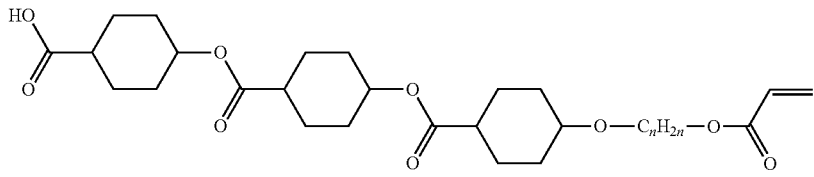
(R-98)
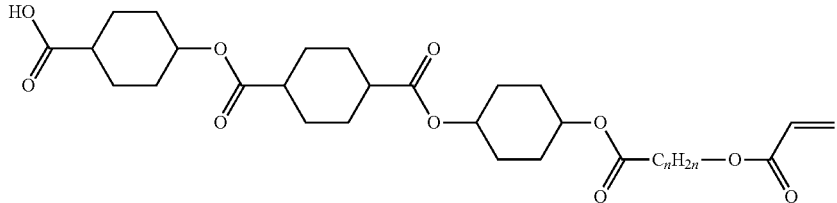
(R-99)

-continued

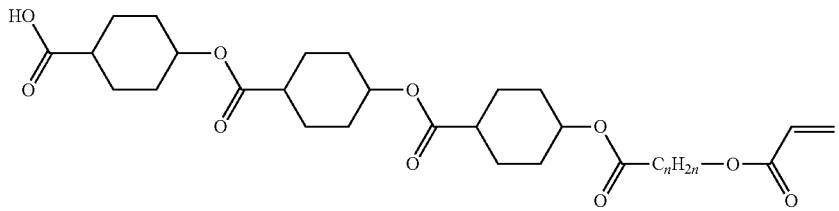
(R-100)

[Chemical Formula 174]

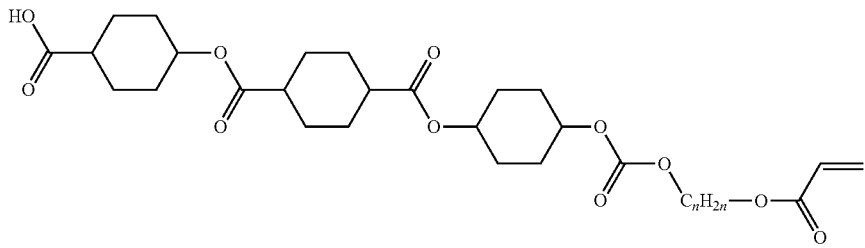
(R-101)

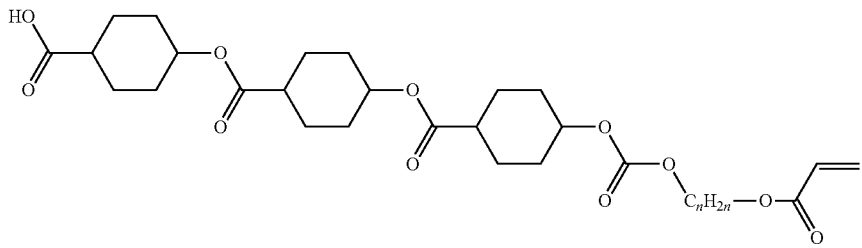
(R-102)

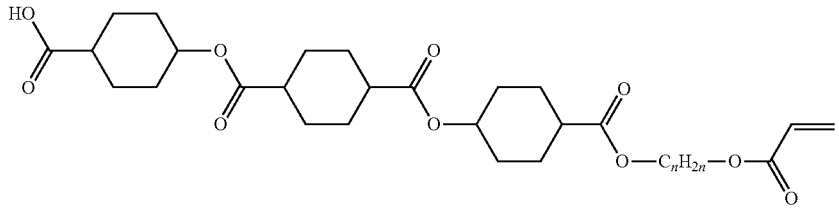
(R-103)

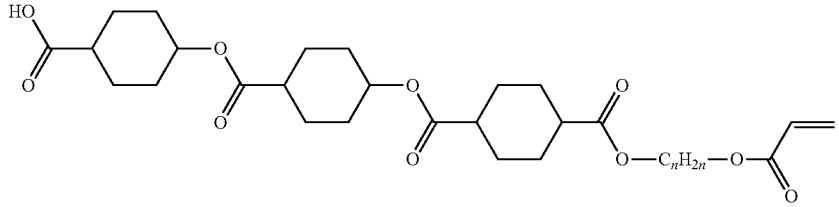
(R-104)

An esterification reaction of an alcohol compound (B) with a carboxylic acid compound (C) is preferably carried out in the presence of a condensing agent. By carrying out the esterification reaction in the presence of a condensing agent, an efficient and rapid esterification reaction can occur.

Examples of the condensing agent include carbodiimide compound compounds such as 1-cyclohexyl-3-(2-morpholinoethyl)carbodiimide metho-p-toluenesulfonate, dicyclohexylcarbodiimide, diisopropylcarbodiimide, 1-ethyl-3-(3-dimethylaminopropyl)carbodiimide, a 1-ethyl-3-(3-dimethylaminopropyl)carbodiimide hydrochloride(water-soluble carbodiimide: commercially available as WSC), bis(2,6-diisopropylphenyl)carbodiimide, and bis(trimethylsilyl)carbodiimide; and a 2-methyl-6-nitrobenzoic acid anhydride, 2,2'-carbonylbis-1H-imidazole, 1,1'-oxalyldiimidazole, diphenylphosphorylazide, 1(4-nitrobenzenesulfonyl)-1H-1,2,4-triazole, 1H-benzotriazole-1-yloxytripyrrolidinophosphoniumhexafluorophosphate, 1H-benzotriazole-1-yloxytris(dimethylamino)phosphonium hexafluorophosphate, N,N,N',N'-tetramethyl-O—(N-succinimidyl)uroniumtetrafluoroborate, N-(1,2,2,2-tetrachloroethoxycarbonyloxy)succinimide, N-carbobenzoxysuccinimide, O-(6-chlorobenzotriazole-1-yl)-N,N,N',N'-tetramethyluronium tetrafluoroborate, O-(6-chlorobenzotriazole-1-yl)-N,N,N',N'-tetramethyluronium hexafluorophosphate, 2-bromo-1-ethylpyridinium tetrafluoroborate, 2-chloro-1,3-dimethylimidazolinium chloride, 2-chloro-1,3-dimethylimidazolinium hexafluorophosphate, 2-chloro-1-methylpyridinium iodide, 2-chloro-1-methylpyridinium p-toluenesulfonate, 2-fluoro-1-methylpyridinium p-toluenesulfonate, and trichloroacetic acid pentachlorophenyl ester.

The condensing agent is preferably a carbodiimide compound, 2,2'-carbonyl-bis-1H-imidazole, 1,1'-oxalyldiimidazole, diphenylphosphorylazide, 1H-benzotriazole-1-yloxytripyrrolidinophosphoniumhexafluoro phosphate, 1H-benzotriazole-1-yloxytris(dimethylamino)phosphonium hexafluorophosphate, N,N,N',N'-tetramethyl-O—(N-succinimidyl)uroniumtetrafluoroborate, N-(1,2,2,2-tetrachloroethoxycarbonyloxy)succinimide, O-(6-chlorobenzotriazole-1-yl)-N,N,N',N'-tetramethyluronium hexafluorophosphate, 2-chloro-1,3-dimethylimidazolinium chloride, 2-chloro-1,3-dimethylimidazolinium hexafluorophosphate, 2-chloro-1-methylpyridinium iodide, and 2-chloro-1-methylpyridinium p-toluenesulfonate.

The condensing agent is more preferably a carbodiimide compound, 2,2'-carbonyl-bis-1H-imidazole, 1H-benzotriazole-1-yloxytripyrrolidinophosphoniumhexafluoro phosphate, 1H-benzotriazole-1-yloxytris(dimethylamino)phosphonium hexafluorophosphate, N,N,N',N'-tetramethyl-O—(N-succinimidyl)uroniumtetrafluoroborate, O-(6-chlorobenzotriazole-1-yl)-N,N,N',N'-tetramethyluronium hexafluorophosphate, 2-chloro-1,3-dimethylimidazolinium chloride, and 2-chloro-1-methylpyridinium iodide, furthermore preferably, from the view point of economy, a carbodiimide compound.

Among the carbodiimide compounds, dicyclohexylcarbodiimide, diisopropylcarbodiimide, 1-ethyl-3-(3-dimethylaminopropyl)carbodiimide, a 1-ethyl-3-(3-dimethylaminopropyl)carbodiimide hydrochloride (water-soluble carbodiimide: commercially available as WSC), and bis(2,6-diisopropylphenyl)carbodiimide are preferred.

An amount of the condensing agent used is generally 2 to 4 mole relative to 1 mole of an alcohol compound (B).

In an esterification reaction, N-hydroxysuccinimide, benzotriazole, p-nitrophenol, 3,5-dibutyl-4-hydroxytoluene, and the like can be further added as additives, and then mixing can be carried out. An amount of the additives used is preferably 0.01 to 1.5 mole relative to 1 mole of a condensing agent. An amount of the additives used is preferably 0.01 to 1.5 mole relative to 1 mole of a condensing agent.

The esterification reaction can be performed in the presence of a catalyst. Examples of the catalyst include N,N-dimethylaminopyridine, N,N-dimethylaniline, and dimethylammonium pentafluorobenzenesulfonate. Among others, the catalyst is preferably N,N-dimethylaminopyridine and N,N-dimethylaniline, more preferably N,N-dimethylaminopyridine. An amount of the catalyst used is preferably 0.01 to 0.5 mole relative to 1 mole of an alcohol compound (B).

Esterification reaction is generally performed in a solvent. Examples of the solvent include a ketone-based solvent such as acetone, methylethylketone, cyclopentanone, cyclohexanone, methyl amyl ketone, or methyl isobutyl ketone; an aliphatic hydrocarbon solvent such as pentane, hexane, or heptane; an aromatic hydrocarbon solvent such as toluene, xylene, benzene, or chlorobenzene; a nitrile-based solvent such as acetonitrile; an ether-based solvent such as tetrahydrofuran or dimethoxyethane; an ester-based solvent such as ethyl lactate; a halogenated hydrocarbon solvent such as chloroform or dichloromethane; an aprotic polar solvent such as dimethylsulfoxide, N-methyl-2-pyrrolidone, N,N-dimethylformamide, N,N-dimethylacetamide or hexamethylphosphoric triamide. The organic solvent can be used alone, or 2 or more of the organic solvents can be used in combination.

From the view point of reaction yield and productivity, the solvent is preferably a nonpolar organic solvent such as pentane, hexane, heptane, toluene, xylene, benzene, chlorobenzene, chloroform, dichloromethane, and the like, more preferably toluene, xylene, benzene, chlorobenzene, chloroform, and dichloromethane.

An amount of the carboxylic acid compound (C) used is preferably 2 to 10 mole relative to 1 mole of the alcohol compound (B), more preferably 2 to 5 mole, further more preferably 2 to 3 mole.

An amount of the solvent used is preferably 0.5 to 50 parts by mass relative to 1 parts by mass of the sum of an alcohol compound (B) and a carboxylic acid compound (C), more preferably 1 to 20 parts by mass, further more preferably 2 to 10 parts by mass.

From the view point of reaction yield and productivity, a temperature of the esterification reaction is preferably −20 to 120° C., more preferably −20 to 60° C., further more preferably −10 to 20° C. From the view point of reaction yield and productivity, time of the esterification reaction is preferably 1 minute to 72 hours, more preferably 1 to 48 hours, further more preferably 1 to 24 hours. A polymerizable liquid crystal compound can be obtained from the resultant suspension by a method such as filtration, decantation, or the like.

<Liquid Crystal Composition>

A liquid crystal composition of the present invention contains aluminum in addition to the polymerizable liquid crystal compound. In the liquid crystal composition of the present invention, the aluminum acts as a catalyst to produce a polymer from the polymerizable liquid crystal compound contained in the liquid crystal composition. Accordingly, during a liquid crystal composition of the present invention is dissolved in a solvent, in the solution in which a polymerizable liquid crystal compound and its polymer are dissolved, it is considered that the polymer can increase solvation of the polymerizable liquid crystal compound to stabilize supersaturation. Thus, the liquid crystal composition of the present invention can prevent precipitation of the polymerizable liquid crystal compound even in long-term storage, that is, the liquid crystal composition has excellent storage stability.

In general, in order to increase solubility in a solvent, in a compound having many cyclic structures, a technique of introducing a long-chain alkyl group is used. However, in a polymerizable liquid crystal compound, when a long-chain alkyl group is introduced as a substituent, molecular alignment of the liquid crystal compound is disorganized by the presence of the introduced substituent, which causes an alignment defect in an optical film. In the liquid crystal composition of the present invention, a polymer of the polymerizable liquid crystal compound is produced, without introducing a substituent such as a long-chain alkyl group, from the polymerizable liquid crystal compound using aluminum as a catalyst, and thus existence of a monomer of the polymerizable liquid crystal compound and its polymer can prevent precipitation of the polymerizable liquid crystal compound. Thus, the liquid crystal composition of the present invention hardly produces an alignment defect, and can provide high storage stability.

Forms of aluminum contained in the liquid crystal composition of the present invention is not specifically limited, and can be a single-element aluminum, an aluminum alloy, or a trivalent aluminum compound. Examples of the aluminum alloy include aluminum-copper-based alloys, aluminum-silicon-based alloys, aluminum-nickel-based alloys, aluminum-iron-based alloys, and aluminum-magnesium-based alloys, and examples of the trivalent aluminum compound include aluminum chloride, aluminum oxide, aluminum phosphide, aluminum nitrate, aluminum hydroxide, aluminum phosphate, aluminum silicate, and aluminum sulfate. The liquid crystal composition of the present invention can contain one of these aluminum compounds alone, can contain 2 or more of the compounds, or can contain a single-element aluminum, an aluminum alloy, and an aluminum compound.

The aluminum contained in the liquid crystal composition of the present invention can be an aluminum added during preparation of the liquid crystal composition to provide a predetermined concentration, can be an aluminum derived from an aluminum used in a process of preparation of the polymerizable liquid crystal compound or the liquid crystal composition, and also can be an aluminum derived from an aluminum contained in a raw material used and carried into the composition with the raw material.

In the liquid crystal composition of the present invention, an aluminum content is 1 ppm or more and 170 ppm or less relative to the polymerizable liquid crystal compound contained in the liquid crystal composition. When the aluminum content is less than 1 ppm, the aluminum cannot act as a catalyst sufficiently, which can incur a risk of difficulty in producing a polymer of the polymerizable liquid crystal compound. On the other hand, when the aluminum content is more than 170 ppm, the polymerization reaction exceeds to much to develop a tendency of gelation of the liquid crystal composition, which can result in difficulty of coating the resultant polymer on a supporting substrate, and the like. In the liquid crystal composition of the present invention, the minimum value of the aluminum content is preferably 1 ppm or more, more preferably 2 ppm or more, further more preferably 5 ppm or more. On the other hand, the maximum value of the aluminum content is preferably 170 ppm or less, more preferably 160 ppm or less, further more preferably 110 ppm or less. When the aluminum content is within the above range, a liquid crystal composition having excellent long-term storage stability can be obtained. The aluminum content is measured as a content of aluminum element by ICP (Inductively Coupled Plas) emission analysis as described in EXAMPLE section.

For efficient progression of the polymerization reaction, the liquid crystal composition of the present invention preferably contains an organic solvent. The organic solvent which can be contained in the liquid crystal composition of the present invention is only have to be an organic solvent which can dissolve a polymerizable liquid crystal compound, and the like, and the solvent also have to be inactive on the polymerization reaction.

Examples of the organic solvent include an alcohol such as methanol, ethanol, ethyleneglycol, isopropyl alcohol, propylene glycol, methyl cellosolve, butyl cellosolve, or propylene glycol monomethyl ether; an ester-based solvent such as ethyl acetate, butyl acetate, ethylene glycol methylether acetate, γ-butyrolactone, propylene glycol methylether acetate, or ethyl lactate; a ketone-based solvent such as acetone, methylethylketone, cyclopentanone, cyclohexanone, methyl amyl ketone, or methyl isobutyl ketone; a non-chlorine aliphatic hydrocarbon solvent such as pentane, hexane, or heptane; non-chlorine aromatic hydrocarbon solvent such as toluene, xylene, or phenol; a nitrile-based solvent such as acetonitrile; an ether-based solvent such as tetrahydrofuran or dimethoxyethane; a chlorine-based solvent such as chloroform or chlorobenzene; an amide-based solvent such as N-methylpyrrolidone (NMP) or N,N-dimethylformamide (DMF). The organic solvent is preferably an ester-based solvent, ketone-based solvent, a non-chlorine aromatic hydrocarbon solvent, an ether-based solvent, and an amide-based solvent, more preferably a ketone-based solvent and an amide-based solvent, further more preferably an amide-based solvent. The organic solvent can be used alone, or 2 or more of the organic solvents can be used in combination.

A content of the organic solvent in the liquid crystal composition of the present invention is preferably 100 to 10000 parts by mass relative to 100 parts by mass of the polymerizable liquid crystal compound, more preferably 200 to 5000 parts by mass, further more preferably 500 to 2500 parts by mass. When the content of the organic solvent is within the above range, the thickness of the obtained optical film (a retardation film) is not excessively thin, and an optical film having a required birefringence value for optical compensation of a liquid crystal panel tends to be easily obtained.

Further, the liquid crystal composition of the present invention has excellent solubility in various an organic solvent. Thus, the liquid crystal composition of the present invention has excellent storage stability during dissolution in a solvent, and also is advantageous to reduce an amount of an organic solvent used for application, storage, and the like. For example, when N-methylpyrrolidone is used as a solvent, the solvent, which is contained in the composition, only in an amount of, for example, 2500 parts by mass or less relative to 100 parts by mass of the polymerizable liquid crystal compound, for example, 1500 parts by mass or less, especially 1000 parts by mass or less can prevent precipitation of the polymerizable liquid crystal compound for a long period of time (e.g., 24 hours or more, preferably 72 hours or more).

The liquid crystal compound of the present invention can be obtained by, for example, mixing a polymerizable liquid crystal compound, aluminum, and an organic solvent. Because the polymerizable liquid crystal compound can be easily dissolved in an organic solvent, and because the polymerization reaction of the polymerizable liquid crystal compound can efficiently proceed with aluminum as a catalyst, heating at the time of mixing or after mixing of the polymerizable liquid crystal compound, aluminum, and the organic solvent is preferred. For such heating, heating temperature or heating time can be suitably determined to provide a polymer in a desired amount or with a desired molecular weight. In one embodiment of the present invention, heating temperature is, for example, 40 to 200° C., preferably 45 to 150° C., more preferably 50 to 100° C. On the other hand, heating time is, for example, 1 minute to 24 hours, preferably 1 to 12 hours, more preferably 1 to 8 hours.

Specifically, the above-mentioned heating can be performed, for example, by placing a liquid crystal composition, a solvent, a stirring bar in a vial, and mixing them with a carousel.

In the liquid crystal composition of the present invention, a polymer produced from the polymerizable liquid crystal compound in the presence of aluminum has a weight-average molecular weight (Mw) of preferably 5000 to 100000, more preferably 8000 to 80000, further more preferably 10000 to 60000 measured by gel permeation chromatography (GPC). When the weight-average molecular weight of the polymer produced from the polymerizable liquid crystal compound is within the above range, gelation of the liquid crystal composition hardly occurs, and thus difficulty in coating on a supporting substrate and the like is reduced.

In an area percentage value measured by gel permeation chromatography (GPC), the liquid crystal composition of the present invention contains a polymer in an amount, as an area percentage value of the polymer, of preferably 0.1% or more and 30% or less relative to the total peak area of the polymerizable liquid crystal compound and the produced polymer contained in the liquid crystal composition, more preferably 0.2% or more and 25% or less, further more preferably 0.3% or more and 20% or less, particularly preferably 0.4% or more and 16% or less. When the area percentage value of the produced polymer is not smaller than the aforementioned minimum value, precipitate of the polymerizable liquid crystal compound is hard to be produced during storage, and then when the liquid crystal composition of the present invention is dissolved in various solvents, precipitation of the polymerizable liquid crystal compound can be prevented for a long period of time (e.g., 24 hours or more, preferably 72 hours or more). On the other hand, when the value is not greater than the aforementioned maximum value, gelation of the liquid crystal composition hardly occurs, and thus difficulty in coating on a supporting substrate and the like is reduced. The area percentage value is calculated by the following formula using GPC (using polystyrene standards).

$$\text{Area Percentage of Polymer} = \frac{\text{Area of Polymer}}{\text{Area of Polymerizable Liquid Crystal Compound }(A) + \text{Area of Polymer}} \times 100$$

A maximum absorption wavelength ($\lambda_{max}$) of the liquid crystal composition of the present invention is preferably 300 to 400 nm, more preferably 315 to 385 nm, further more preferably 320 to 380 nm. When the maximum absorption wavelength ($\lambda_{max}$) of the liquid crystal composition is not smaller than the aforementioned minimum value, a retardation film comprising a polymer of the liquid crystal composition in oriented state tends to show reverse wavelength dispersibility. When the maximum absorption wavelength ($\lambda_{max}$) of the liquid crystal composition is not greater than the aforementioned maximum value, absorption in visible light region is suppressed, and thus coloration of the film can be prevented.

In one embodiment of the present invention, a retardation film (hereinafter, also referred to as "a retardation film of the present invention") comprising a polymer of the above-mentioned liquid crystal composition in oriented state is provided. The retardation film of the present invention preferably satisfies wavelength dispersion, Re (450 nm)/Re (550 nm), of the following formula (1).

$$0.80 \leq Re(450)/Re(550) < 1.00 \quad (1)$$

in formula (1), Re ($\lambda$) represents a front retardation value with respect to a light having a wavelength of $\lambda$ nm.

The wavelength dispersion, Re(450 nm)/Re(550 nm), of the retardation film of the present invention is more preferably 0.8 or more and less than 0.97, further more preferably 0.8 or more and less than 0.96. When the wavelength dispersion, Re(450 nm)/Re(550 nm), of the retardation film of the present invention is not smaller than the aforementioned minimum value, it is preferred because circular polarization conversion can be performed in a short wavelength range of around 450 nm. When the wavelength dispersion, Re(450 nm)/Re(550 nm), of the retardation film of the present invention is smaller than the aforementioned maximum value, it is preferred because the obtained retardation film shows reverse wavelength dispersibility.

The retardation film of the present invention has excellent transparency and can be used in various optical displays.

The thickness of the retardation film is preferably 0.1 to 10 μm, and is more preferably 0.5 to 3 μm to reduce its photoelasticity.

When the retardation film of the present invention is used for a λ/4 plate, the film thickness of the retardation film can be controlled to provide a retardation value (Re (550 nm)) of the obtained retardation film at a wavelength of 550 nm of preferably 113 to 163 nm, more preferably 130 to 150 nm, particularly preferably about 135 nm to about 150 nm.

When the retardation film of the present invention is used for an optical film for VA (Vertical Alignment) mode, the film thickness of the retardation film can be controlled to provide Re (550 nm) of preferably 40 to 100 nm, more preferably about 60 to about 80 nm.

A combination of the retardation film of the present invention and a polarizing film provides a polarizing plate (hereinafter, also referred to as "a polarizing plate of the present invention"), especially an elliptically polarizing plate and a circularly polarizing plate. In the elliptically polarizing plate and the circularly polarizing plate, the retardation film of the present invention is stuck on the polarizing film. Further, the present invention can also provide a wide-band circularly polarizing plate in which the retardation film of the present invention as a wide-band λ/4 plate is further stuck on the elliptically polarizing plate or the circularly polarizing plate.

In one embodiment of the present invention, the polarizing plate of the present invention can be used in an optical display including the polarizing plate of the present invention, such as a reflective liquid crystal display and an organic electroluminescence (EL) display. The above-mentioned FPD is not Specifically limited, and examples of the FPD include a liquid crystal display (LCD) and an organic electroluminescent display device.

In the present invention, an optical display comprises a polarizing plate of the present invention, and examples of the optical display include a liquid crystal display comprising a bonded material in which the polarizing plate and the liquid crystal panel are stuck together, and an organic electroluminescent display device comprising an organic electroluminescent panel in which the polarizing plate of the present invention and a light emitting layer are stuck together.

In the present invention, the retardation film refers to a film used for converting linearly polarized light into circularly polarized light or elliptically polarized light, and on the contrary, converting circularly polarized light or elliptically polarized light into linearly polarized light. The retardation film of the present invention comprises a polymer of the liquid crystal composition of the present invention. That is, the retardation film of the present invention comprises a polymer consisting of a structural unit derived from the polymerizable liquid crystal compound.

For example, the retardation film of the present invention can be produced by the following method.

First, to the liquid crystal composition of the present invention was added an additive, as required, such as a polymerization initiator, a polymerization inhibitor, a photosensitizer, or a leveling agent to prepare a mixed solution.

[Polymerization Initiator]

The liquid crystal composition of the present invention can contain a polymerization initiator because the polymerization initiator has a hardening effect on the obtained retardation film. The polymerization initiator is not specifically limited so long as having an ability to initiate polymerization of the polymerizable liquid crystal compound, and the polymerization initiator can be suitably selected from publicly-known polymerization initiators. In the present invention, examples of the polymerization initiator include a photo polymerization initiator, and a thermal polymerization initiator, and the polymerization initiator is preferably a photo polymerization initiator.

Examples of the photo polymerization initiator include, benzoins, benzophenones, benzyl ketals, α-hydroxyketones, α-aminoketones, iodonium salt, and a sulfonium salt, and more specifically include IRGACURE (Irgacure) 907, IRGACURE 184, IRGACURE 651, IRGACURE 819, IRGACURE 250, IRGACURE 369 (all manufactured by Ciba Japan K.K.), SEIKUOL BZ, SEIKUOL SEIKUOL BEE (all manufactured by Sun Chemtech Co., Ltd), KAYACURE (kayacure) BP 100 (manufactured by Nippon Kayaku Co., Ltd.), KAYACURE UVI-6992 (manufactured by The Dow Chemical Company), ADEKA OPTOMER SP-152, or ADEKA OPTOMER SP-170 (all manufactured by ADEKA CORPORATION).

In the liquid crystal composition of the present invention, a content of the polymerization initiator is, for example, 0.1 to 30 parts by mass relative to 100 parts by mass of the polymerizable liquid crystal compound, preferably 0.5 to 20 parts by mass, more preferably 0.5 to 10 parts by mass. When the content of the polymerization initiator is within the above range, the polymerizable liquid crystal compound can be polymerized without disorganizing an alignment property of the liquid crystal compound.

[Polymerization Inhibitor]

A polymerization inhibitor can be used in preparing the retardation film of the present invention. Examples of the polymerization inhibitor include hydroquinone or hydroquinones having a substituent such as an alkylether; catechols having a substituent such as an alkylether, such as butylcatechol; pyrogallols; a radical scavenger such as 2,2,6,6-tetramethyl-1-piperidinyloxy radical; thiophenols; β-naphthylamines; or β-naphthols.

By using the polymerization inhibitor, polymerization of the polymerizable liquid crystal compound can be controlled, and stability of the obtained retardation film can be improved. An amount of the polymerization inhibitor used is, for example, 0.1 to 30 parts by mass relative to 100 parts by mass of the polymerizable liquid crystal compound, preferably 0.5 to 10 parts by mass. When the amount is within the above range, the polymerizable liquid crystal compound can be polymerized without disorganizing an alignment property of the liquid crystal compound.

[Photosensitizer]

Further, a photosensitizer can be used in preparing the retardation film of the present invention. Examples of the photosensitizer include xanthones such as xanthone or thioxanthone; anthracene or anthracenes having a substituent such as an alkylether or the like; phenothiazine; or rubrene.

By using the photosensitizer, polymerization of the polymerizable liquid crystal compound can be highly sensitized.

An amount of the photosensitizer used is, for example, 0.1 to 30 parts by mass relative to 100 parts by mass of the polymerizable liquid crystal compound, preferably 0.5 to 10 parts by mass. When the amount is within the above range, the polymerizable liquid crystal compound can be polymerized without disorganizing an alignment property of the liquid crystal compound.

[Leveling Agent]

Further, a leveling agent can be used in preparing the retardation film of the present invention. Examples of the leveling agent include an additives for a radiation curable paint (manufactured by BYK Japan KK: BYK-352, BYK-353, or BYK-361N), a paint additive (manufactured by Dow Corning Toray Co., Ltd.: SH28PA, DC11PA, or ST80PA), a paint additive (manufactured by Shin-Etsu Chemical Co., Ltd.: KP321 KP323, X22-161A, or KF6001), or a fluorine-based additive (manufactured by DIC Corporation: F-445, F-470, or F-479).

By using the leveling agent, the obtained retardation film can be smoother. Further, in the production process of the retardation film, fluidity of a mixed solution containing the liquid crystal composition can be controlled, and crosslinking density of the retardation film obtained by polymerizing the polymerizable liquid crystal compound can be regulated. Further, a specific value of an amount of the leveling agent used is, for example, 0.1 to 30 parts by mass relative to 100 parts by mass of the polymerizable liquid crystal compound, preferably 0.5 to 10 parts by mass. When the amount is within the above range, the polymerizable liquid crystal compound can be polymerized without disorganizing an alignment property of the liquid crystal compound.

Viscosity of the mixed solution containing the liquid crystal composition of the present invention is controlled at, for example, 10 Pa·s or less, preferably about 0.1 to about 7 Pa·s for easy coating. Then, viscosity of the mixed solution can be controlled by a content of the organic solvent.

A concentration of a solid content in the mixed solution is, for example, 5 to 50% by mass, preferably 5 to 30% by mass, more preferably 5% to 15% by mass. Then, "a solid content" used herein refers to an ingredient of the mixed solution (the liquid crystal composition) excluding a solvent. When the concentration of the solid content is 5% or more, the thickness of the obtained retardation film is not excessively thin, and a birefringence value required for an optical compensation of a liquid crystal panel tends to be achieved. On the other hand, the solid content of 50% or less is preferred because viscosity of the mixed solution is low, and thus irregularity of the film thickness of the retardation film tends to be reduced.

Next, coating the mixed solution containing the liquid crystal composition of the present invention to the supporting substrate, and drying the resultant to give an unpolymerized film on the supporting substrate. When the unpolymerized film exhibits a liquid crystal phase such as a nematic phase, the obtained retardation film has a birefringent property based on monodomain alignment. Since the unpolymerized film aligns at a low temperature such as about 0 to about 120° C., preferably 25 to 80° C., a supporting substrate having sometimes insufficient heat resistance for the alignment film can be used. Moreover, it is easy to handle because crystallization does not occur when the resultant is further cooled to about 30 to about 10° C. after aligning.

Then, the film thickness can be controlled to give a desired phase difference by suitably adjusting an amount of the mixed solution coated or concentration of the mixed solution. When the mixed solution contains a fixed amount of the polymerizable liquid crystal compound, a phase difference value (retardation value, Re(λ)) of the obtained retardation film is determined according to formula (I). Thus, the film thickness d can be controlled to obtain a desired Re(λ).

$$Re(\lambda) = d \times \Delta n(\lambda) \qquad (I)$$

wherein Re(λ) represents a phase difference value at a wavelength of λ nm, d represents a film thickness, and Δn(λ) represents a birefringence value at a wavelength of λ nm.

Examples of a coating method to the supporting substrate include an extrusion coating method, a direct gravure coating method, a reverse gravure coating method, a CAP coating method, or a die coating method. The coating method also include a method for coating using a coater such as a dip coater, a bar coater, or a spin coater.

Examples of the supporting substrate include glass, plastic sheet, a plastic film, or a light transparent film. Then, examples of the light transparent film include a polyolefin film such as polyethylene, polypropylene, norbornene-based polymer, or the like, a polyvinyl alcohol film, a polyethylene terephthalate film, a polymethacrylic acid ester film, polyacrylic ester film, a cellulose ester film, a polyethylene naphthalate film, a polycarbonate film, a polysulfone film, a polyether sulfone film, a polyetherketone film, a polyphenylene sulfide film, or a polyphenylene oxide film.

By using the supporting substrate, the retardation film of the present invention can be easily handled without breakage in a step, which requires strength of the retardation film, such as a sticking step, a transport step, a storage step, or the like.

Further, it is preferred that forming the alignment film on the supporting substrate, and applying the mixed solution containing the liquid crystal composition of the present invention to the alignment film. The alignment film preferably is solvent resistant, that is, insoluble to the mixed solution during application of the mixed solution containing the liquid crystal composition of the present invention, etc., heat resistant during heat treatment for removal of a solvent or for aligning a liquid crystal, and free of peeling by friction or the like during rubbing, and preferably comprises a polymer or a composition containing a polymer.

Examples of the polymer include a polymer including polyamide or gelatins having an intramolecular amide bond, polyimide having an intramolecular imide bond and its hydrolysate, that is, polyamic acid, polyvinyl alcohol, alkyl-modified polyvinyl alcohol, polyacrylamide, polyoxazole, polyethyleneimine, polystyrene, polyvinylpyrrolidone, polyacrylic acid, polyacrylic esters, or the like. The polymer can be used alone, or 2 or more of the polymers can be mixed or copolymerized. These polymers can be easily obtained by polycondensation with dehydration or deamination, chain polymerization such as radical polymerization, anionic polymerization, or cationic polymerization, or coordination polymerization, a ring-opening polymerization, and the like.

Further, these polymers can be dissolved in a solvent to carry out coating. The solvent is not specifically limited, but specifically, examples of the solvent include water; an alcohol such as methanol, ethanol, ethyleneglycol, isopropyl alcohol, propylene glycol, methyl cellosolve, butyl cellosolve, or propylene glycol monomethyl ether; an ester-based solvent such as ethyl acetate, butyl acetate, ethylene glycol methylether acetate, γ-butyrolactone, propylene glycol methylether acetate, or ethyl lactate; a ketone-based solvent such as acetone, methylethylketone, cyclopentanone, cyclohexanone, methyl amyl ketone, or methyl isobutyl ketone; a non-chlorine aliphatic hydrocarbon solvent such as pentane, hexane, or heptane; a non-chlorine aromatic hydrocarbon solvent such as toluene or xylene; a nitrile-based solvent such as acetonitrile or the like; an ether-based solvent such as tetrahydrofuran or dimethoxyethane; chlorine-based solvent such as chloroform or chlorobenzene. The organic solvent can be used alone, or 2 or more organic solvents can be used in combination.

In order to form the alignment film, a commercially available alignment film material can be used as it is. Examples of the commercially available alignment film material include SUNEVER (registered trademark, manufactured by Nissan Chemical Industries, Ltd.), or OPTMER (registered trademark, manufactured by JSR Corporation).

When the above-mentioned alignment film is used, control of refraction by stretching is not required, and thus in-plane variation of birefringence is reduced. Accordingly, use of the above-mentioned alignment film can be effective in providing a large retardation film, which enables capsizing of a flat panel display (FPD), on the supporting substrate.

Examples of a method for forming an alignment film on the above-mentioned supporting substrate include a method including applying a solution of a commercially available alignment film material or a solution of a compound which can be a material for an alignment film on the above-mentioned supporting substrate, and then annealing the resultant to form an alignment film on the above-mentioned supporting substrate.

The thickness of the alignment film thus obtained is, for example, 10 nm to 10000 nm, preferably 10 nm to 1000 nm. When the thickness is within the above range, the polymerizable liquid crystal compound and the like can be aligned on the alignment film at a desired angle.

Further, these alignment films can be subjected to rubbing or irradiated with polarized UV. By forming the alignment film, the polymerizable liquid crystal compound and the like can be aligned to a desired direction.

Examples of the method used for rubbing the alignment film include bringing a rubbing roller, which is wrapped with a rubbing cloth and rotating, into contact with the alignment film which is placed on a stage and conveyed.

As described above, in a step for preparing the unpolymerized film, the unpolymerized film (liquid crystal layer) can be laminated on an alignment film which is laminated on any supporting substrate. In this step, production cost can be lowered as compared to the cost by a method of producing a liquid crystal cell and injecting a liquid crystal composition into the liquid crystal cell. Further, the film can be produced using a roll film.

The solvent can be removed during the polymerization process, however, preferably most solvent should be removed before polymerization for advantageous formation of the film.

Examples of the method for removing the solvent include methods of natural drying, draught drying, and reduced pressure drying. Heating temperature is, specifically, preferably 10 to 120° C., further preferably 25 to 80° C. Heating time is preferably 10 seconds to 60 minutes, more preferably 30 seconds to 30 minutes. When the heating temperature and the heating time are within the above ranges, a supporting substrate having sometimes insufficient heat resistance can be used as the supporting substrate.

Further, the thus obtained unpolymerized film is polymerized and cured. By the polymerization and curing, a film in which the alignment property of the polymerizable liquid crystal compound is fixed, that is, a film containing a polymer of the liquid crystal composition of the present invention (hereinafter, also referred to as "a polymerized film") is provided. Then, a polymerized film having small alteration of refraction index in a planar direction of the film, and having large alteration of refraction index in the normal direction of the film can be produced.

A method for polymerizing the unpolymerized film is determined according to types of the polymerizable liquid crystal compound. The unpolymerized film can be polymerized by photo polymerization when the polymerizable group contained in the polymerizable liquid crystal compound is a photo-polymerizable group, or can be polymerized by thermal polymerization when the polymerizable group is a thermal-polymerizable group. In the present invention, especially preferably, the unpolymerized film is polymerized by photo polymerization. In the photo polymerization, polymerization of the unpolymerized film can be performed at low temperature, and thus supporting substrates having various heat resistances can be selected. Further, easy industrial production can be achieved. Photo polymerization is also preferable from the view point of advantageous formation of the film. The photo polymerization of the unpolymerized film is performed by visible light irradiation, ultraviolet light irradiation, or laser light irradiation. Light irradiation, in which ultraviolet light irradiation is particularly preferable from the view point of ease of handling, can be performed while heating at a temperature at which the polymerizable liquid crystal compound is in liquid crystal phase. Further, patterning of the polymerized film can be performed by masking and the like.

Further, the retardation film of the present invention is thinner than an oriented film in which phase difference is achieved by stretching of the polymer.

In a method for producing the retardation film of the present invention, a step of peeling the supporting substrate can further be included. According to the above constitution, an obtained laminated material is a film consisting of the alignment film and the retardation film. Further, in addition to the above-mentioned step of peeling the supporting substrate, a step of peeling the alignment film can further be included. According to the above constitution, a retardation film can be provided.

EXAMPLES

Hereinafter, the present invention will be described in more detail with reference to Examples. In the Examples, "%" and "part(s)" refer to "% by mass" and "part(s) by mass", unless otherwise described.

Conditions for gel permeation chromatography (GPC) analysis are provided below.

<Conditions for GPC Analysis>
Analysis System: HLC-8220 (Tosoh Corporation)
Column: TSKgel SuperMultiporeHZ-N 3 columns
Column Temperature: 40° C.
Inlet Oven: 40° C.
Mobile Phase: Tetrahydrofuran
Analysis Time: 20 minutes
Flow Rate of Sample Pump: 0.35 mL/min
Flow Rate of Reference Pump: 0.35 mL/min
Injection Volume: 10 μL
Detection: UV absorbance (Wavelength: 254 nm)

An aluminum content was measured by ICP emission spectrometry according to the following method.

(i) A sample is weighed into a quartz vessel for decomposition.

(ii) To the weighed sample are added sulfuric acid and nitric acid to decompose with heat on a hot plate.

(iii) When color of the sample is changed from brown to black, the sample is removed from the hot plate to allow to cool.

(iv) Next, pure water and hydrochloric acid are added to dissolve with heat on a hot plate.

(v) The obtained solution is diluted to a constant volume with pure water, and the aluminum content is measured as a content of Al element using an ICP emission spectrometer (SPS 5520, Hitachi High-Technologies Corporation).

1. Examples 1 to 5

(1) Synthesis of Polymerizable Liquid Crystal Compound (1-1) Synthesis Example (1)

According to the following method, a polymerizable liquid crystalline mixture (A-1a) containing a polymerizable liquid crystal compound represented by the following formula (A-1) (hereinafter, also referred to as "a compound (A-1)") and aluminum was synthesized.

[Chemical Formula 175]

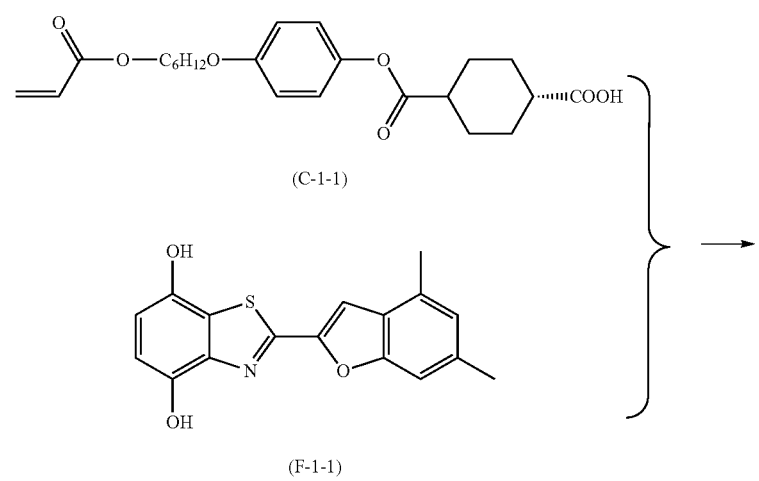

(C-1-1)

(F-1-1)

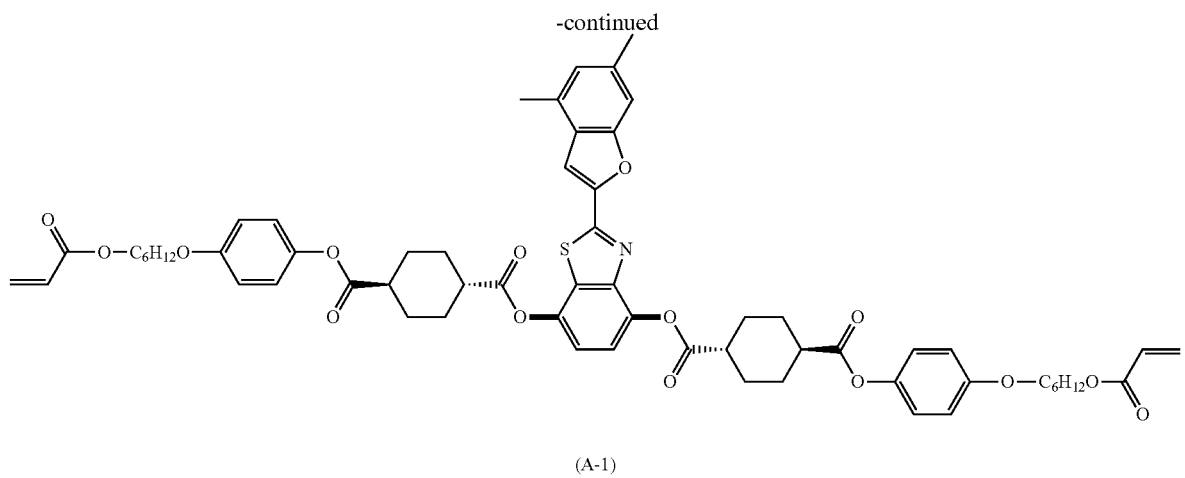

(A-1)

(i) Synthesis of a Compound Represented by Formula (C-1-1)

A compound represented by formula (C-1-1) was synthesized with reference to a patent document (JP-A-2015-157776).

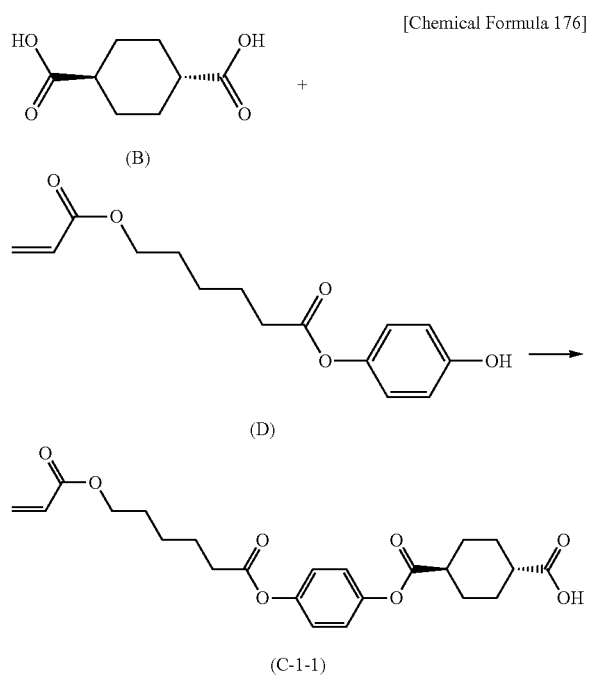

In a 100 mL 4-neck flask equipped with a Dimroth condenser and a thermometer filled with nitrogen atmosphere, 36 g of trans-cyclohexanedicarboxylic acid represented by formula (3) shown above (a commercially available product, and a content of aluminum element measured by the ICP emission spectrometry was 3 ppm) and 72 g of N-methyl-2-pyrrolidone (manufactured by KANTO CHEMICAL CO., INC.) were mixed to give a solution. To the obtained solution were added 9.9 g of a monoalcohol compound represented by formula (D) shown above, 0.7 g of dibutylhydroxytoluene (hereinafter, abbreviated as "BHT") (manufactured by Wako Pure Chemical Industries, Ltd.) and 0.055 g of 4-dimethylaminopyridine (hereinafter, abbreviated as "DMAP") (manufactured by Wako Pure Chemical Industries, Ltd.) were added, and the temperature was controlled at 45° C. To the obtained mixture was added dropwise 6.9 g of diisopropylcarbodiimide (hereinafter, abbreviated as "IPC") (manufactured by Wako Pure Chemical Industries, Ltd.) over 1 hour, and then esterification reaction was performed with stirring for 15 hours to provide a reaction mixture A.

On the other hand, 2.1 g of sodium hydroxide (manufactured by KANTO CHEMICAL CO., INC.) and 145 g of water were mixed, and the obtained mixture was added dropwise to the reaction mixture A, and then the resultant was mixed for 2 hours to provide a suspension. A solid material was obtained by filtration of the obtained suspension, and the obtained solid material was washed 6 times with a mixed solvent of methanol and water (mass ratio of 1:1), and further dried under reduced pressure at 30° C. to give 12.6 g of a compound (C-1-1a) represented by formula (C-1-1) shown above. A yield of the compound (C-1-1a) was 77% based on the compound (D). An aluminum content in the compound (C-1-1a) measured by the ICP emission spectrometry is shown in Table 1.

(ii) Synthesis of a Polymerizable Liquid Crystalline Mixture (A-1a)

In a 100 mL 4-neck flask equipped with a Dimroth condenser and a thermometer filled with nitrogen atmosphere, 11.02 g of a compound (C-1-1a) synthesized by the synthesis method shown above, 4.00 g of a compound (F-1-1) synthesized with reference to a patent document (JP-A-2011-207765), 0.02 g of dimethylaminopyridine (hereinafter, abbreviated as "DMAP") (manufactured by Wako Pure Chemical Industries, Ltd.), 0.20 g of dibutylhydroxytoluene (hereinafter, abbreviated as "BHT") (manufactured by Wako Pure Chemical Industries, Ltd.), and 58 g of chloroform (manufactured by KANTO. CHEMICAL CO., INC.) were mixed, and then 4.05 g of diisopropylcarbodiimide (hereinafter, abbreviated as "IPC") (manufactured by Wako Pure Chemical Industries, Ltd.) was added with a dropping funnel to react overnight at 0° C. After the completion of the reaction, insoluble components were removed by filtration. The obtained chloroform solution was added dropwise to three times the weight of acetonitrile (manufactured by Wako Pure Chemical Industries, Ltd.) relative to the weight of contained chloroform. Then, precipitated solid material was recovered, and washed 3 times with 20 g of acetonitrile, and then dried under reduced pressure at 30° C. to give a polymerizable liquid crystalline mixture (A-1a) containing the compound (A-1) and aluminum. An amount of the obtained polymerizable liquid crystalline mixture (A-1a), a yield of the polymerizable liquid crystalline mixture (A-1a), an aluminum content in the polymerizable liquid crystalline mixture (A-1a), and a maximum absorption wavelength ($\lambda_{max}$) of the compound (A-1) are shown in Table 1. The yield of the polymerizable liquid crystalline mixture (A-1a) was calculated based on the compound (F-1-1).

(1-2) Synthesis Example (2)

(i) Synthesis of a Compound Represented by Formula (C-1-1)

A compound (C-1-1b) represented by formula. (C-1-1) shown above was obtained by the same method as that used in (i) of Synthesis Example 1 except that a different lot of trans-cyclohexanedicarboxylic acid [a commercially available product, and a content of aluminum element was 450 ppm (ICP emission spectrometry)] was used. A yield of the compound (C-1-1b) was 77% based on the compound (D). An aluminum content in the compound (C-1-1b) measured by the ICP emission spectrometry is shown in Table 1.

(ii) Synthesis of Polymerizable Liquid Crystalline Mixture (A-1b)

A polymerizable liquid crystalline mixture (A-1b) containing a compound (A-1) and aluminum was obtained by the same method as that used in Synthesis Example 1 except that a compound (C-1-1b) was used instead of the compound (C-1-1a). An amount of the obtained polymerizable liquid crystalline mixture (A-1b), a yield of the polymerizable liquid crystalline mixture (A-1b), an aluminum content in the polymerizable liquid crystalline mixture (A-1b), and a maximum absorption wavelength ($\lambda_{max}$) of the compound (A-1) are shown in Table 1. The yield of the polymerizable liquid crystalline mixture (A-1b) was calculated based on the compound (F-1-1).

(2) Preparation of Liquid Crystal Composition

According to the formulations shown in Table 2, a vial tube was loaded with the polymerizable liquid crystalline mixtures obtained in Synthesis Example 1 and Synthesis Example 2, a polymerization initiator, a leveling agent, a polymerization inhibitor, and a solvent, and the resultant was stirred using a carousel for 5 hours at 80° C. to give liquid crystal compositions (1) to (5). The formulations shown in Table 2 are represented by percent by mass (% by mass) of each ingredient before heating. Further, aluminum contents relative to the compound (A-1) in the liquid crystal compositions, which were prepared by mixing the ingredients according to the ratios in the formulations shown in Table 2, are shown in Table 3.

Further, every one of aluminum contents of the following polymerization initiator (IRGACURE 369), leveling agent (BYK-361N), polymerization inhibitor (BHT), and solvent (NMP) is 0 (zero) ppm.

TABLE 2

| Liquid crystal composition | Polymerizable liquid crystalline mixture (mass %) | | Polymerization initiator (mass %) | Leveling agent (mass %) | Polymerization inhibitor (mass %) | Solvent (mass %) |
| --- | --- | --- | --- | --- | --- | --- |
| | (A-1a) | (A-1b) | | | | |
| (1) | 12.14 | 0.10 | 0.73 | 0.01 | 0.02 | 87.00 |
| (2) | 11.86 | 0.38 | 0.73 | 0.01 | 0.02 | 87.00 |
| (3) | 10.91 | 1.33 | 0.73 | 0.01 | 0.02 | 87.00 |
| (4) | 5.46 | 6.78 | 0.73 | 0.01 | 0.02 | 87.00 |
| (5) | 2.05 | 10.19 | 0.73 | 0.01 | 0.02 | 87.00 |

Polymerization Initiator: 2-benzyl-2-dimethylamino-1-(4-morpholinophenyl)butane-1-one (IRGACURE 369; manufactured by BASE JAPAN LTD.)

Leveling Agent: polyacrylate compound (BYK-361N; manufactured by BYK Japan KK)

Polymerization Inhibitor: BHT (manufactured by Wako Pure Chemical Industries, Ltd.)

Solvent: N-methylpyrrolidone (NMP; manufactured by KANTO CHEMICAL CO., INC.)

Each of the obtained liquid crystal compositions (1) to (5) contains a polymer of the polymerizable liquid crystal compound (A-1). A weight-average molecular weight and an area percentage value of the polymer were measured by GPC. The results are shown in Table 3.

TABLE 1

| | Compound (C-1-1) | | Polymerizable liquid crystalline mixture | | | | Compound (A-1) Maximum absorption wavelength (nm) |
| --- | --- | --- | --- | --- | --- | --- | --- |
| Synthesis Example | Compound (C-1-1) | Aluminum content (ppm) | Polymerizable liquid crystalline mixture | Amount (obtained) (g) | Yield (%) | Aluminum content (ppm) | |
| (1) | (C-1-1a) | 0.7 | (A-1a) | 11.43 | 80 | 0.5 | 352 |
| (2) | (C-1-1b) | 270 | (A-1b) | 11.21 | 78 | 180 | 352 |

TABLE 3

| Liquid crystal composition | Aluminum content (ppm) relative to compound (A-1) | Molecular weight of polymer (Mw) | Area percentage of polymer (%) | Liquid crystal composition Maximum absorption wavelength (nm) |
|---|---|---|---|---|
| (1) | 2 | 10060 | 0.43 | 352 |
| (2) | 6 | 14047 | 0.60 | 352 |
| (3) | 20 | 16002 | 1.21 | 352 |
| (4) | 100 | 30010 | 9.23 | 352 |
| (5) | 150 | 56032 | 15.4 | 352 |

(3) Evaluation of Storage Stability

Each of the liquid crystal compositions (1) to (5) was stored at 25° C. for carrying out observations about the presence of precipitate of crystals over time, and storage stability was evaluated according to the following evaluation criteria. The results are shown in Table 4.

Evaluation Criteria for Storage Stability
1: Precipitate immediately after the beginning of storage
2: No precipitate after storage for 24 hours
3: No precipitate after storage for 48 hours
4: No precipitate after storage for 72 hours (4) Production of Optical Film (Retardation Film)
<Preparation of Composition for Forming Photo-Alignment Film>

The following components were mixed, and the obtained mixture was stirred for 1 hour at 80° C. to give a composition for forming a photo-alignment film (1).

Photoalignment material (5 parts):

[Chemical Formula 177]

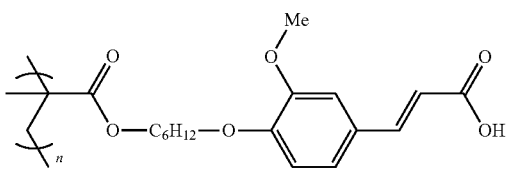

Solvent (95 parts): Cyclopentanone
<Example for Manufacturing Optical Film>

An optical film was manufactured as follows. A cycloolefin polymer film (COP) (ZF-14, manufactured by Zeon Corporation) was treated once using a corona treater (AGF-B10, manufactured by KASUGA ELECTRIC WORKS LTD) Under conditions of output of 0.3 kW and treatment speed of 3 m/min. The above-described composition for forming a photo-alignment film (1) was applied to the corona treated surface with a bar coater, dried at 80° C. for 1 minute, and then subjected to polarized UV exposure at a light integral of 100 mJ/cm² using a polarized UV irradiation device (SPOT CURE SP-7; manufactured by USHIO INC.). The film thickness of the obtained alignment film was 100 nm as measured using a laser microscope (LEXT, manufactured by Olympus Corporation).

Next, each of the liquid crystal compositions (1) to (5) prepared by the same procedure as that of the above-described Evaluation of Storage Stability was applied to the alignment film with a bar coater, dried at 120° C. for 1 minute, and then the resultant was irradiated with ultraviolet rays (under a nitrogen atmosphere, wavelength: 365 nm, light integral at a wavelength of 365 no: 1.000 mJ/cm²) using a high pressure mercury lamp (Unicure VB-15201BY-A, manufactured by USHIO INC.) to give an optical film. Further, a value of Re(450)/Re(550) of the obtained optical film was 0.82, and thus the obtained optical film satisfied the optical property represented by formula (1): 0.8≤Re(450)/Re(550)<1.00.

(5) Evaluation of Alignment Defect

A square piece (10 cm×10 cm) was cut from each of the Obtained optical films, and the number of an alignment defect was counted using a polarization microscope (LEXT, manufactured by Olympus Corporation) on the display by visual inspection. The results are shown in Table 4.

Criteria for Evaluation of Alignment Defect
1: Alignment Defects are developed over the entire surface (>100 defects)
2: 11 to 100 defects
3: 1 to 10 defects
4: No defect

TABLE 4

| | | Liquid crystal composition | | | | Optical film (retardation film) | |
|---|---|---|---|---|---|---|---|
| | | Liquid crystal composition | Molecular weight of polymer (Mw) | Area percentage of polymer (%) | Storage stability | Re(450)/Re(550) | Alignment defect |
| Example | 1 | (1) | 10060 | 0.43 | 4 | 0.82 | 4 |
| | 2 | (2) | 14047 | 0.60 | 4 | 0.82 | 4 |
| | 3 | (3) | 16002 | 1.21 | 4 | 0.82 | 4 |
| | 4 | (4) | 30010 | 9.23 | 4 | 0.82 | 4 |
| | 5 | (5) | 56032 | 15.4 | 4 | 0.82 | 4 |

2. Example 6 to 10

(1) Synthesis of Polymerizable Liquid Crystal Compound (1-1) Synthesis Example (3)

According to the following method, a polymerizable liquid crystalline mixture (A-2a) containing a polymerizable liquid crystal compound represented by the following formula (A-2) (hereinafter, also referred to as "a compound (A-2)") and aluminum was synthesized.

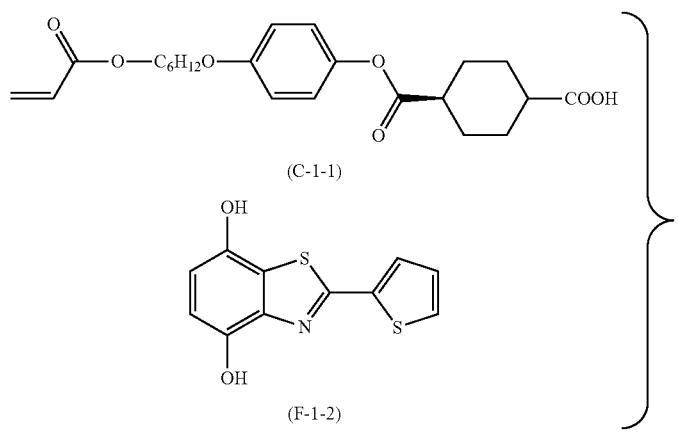

(C-1-1)

(F-1-2)

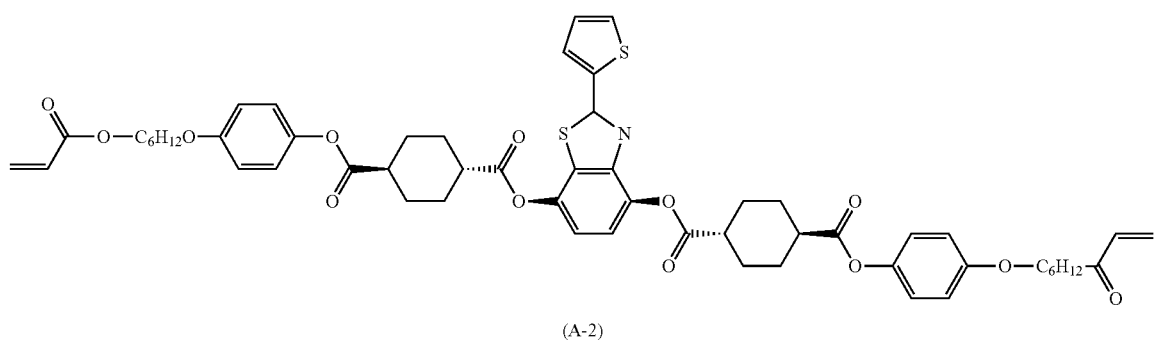

(A-2)

A polymerizable liquid crystalline mixture (A-2a) containing the compound (A-2) and aluminum was obtained under the same conditions as those of Synthesis Example (1) except that a compound (F-1-2) was used instead of the compound (F-1-1) used in Synthesis Example 1. Further, the compound (F-1-2) was synthesized with reference to a patent document (JP-A-2010-31223). An aluminum content in the compound (C-1-1a), an amount of the obtained polymerizable liquid crystalline mixture (A-2a), a yield of the polymerizable liquid crystalline mixture (A-2a), an aluminum content in the polymerizable liquid crystalline mixture (A-2a), and a maximum absorption wavelength ($\lambda_{max}$) of the compound (A-2) are shown in Table 5. The yield of the polymerizable liquid crystalline mixture (A-2a) was calculated based on the compound (F-1-2).

(1-2) Synthesis Example (4)

A polymerizable liquid crystalline mixture (A-2b) containing a compound (A-2) and aluminum was obtained under the same conditions as those of Synthesis Example (2) except that a compound (F-1-2) was used instead of the compound (F-1-1). An aluminum content in the compound (C-1-1b), an amount of the obtained polymerizable liquid crystalline mixture (A-2b), a yield of the polymerizable liquid crystalline mixture (A-2b) an aluminum content in the polymerizable liquid crystalline mixture (A-2b), and a maximum absorption wavelength ($\lambda_{max}$) of the compound (A-2) are shown in Table 5. The yield of the polymerizable liquid crystalline mixture (A-2b) was calculated based on the compound (F'-1-2).

TABLE 5

| | Compound (C-1-1) | | Polymerizable liquid crystalline mixture | | | | Compound (A-1) |
|---|---|---|---|---|---|---|---|
| Synthesis Example | Compound (C-1-1) | Aluminum content (ppm) | Polymerizable liquid crystalline mixture | Amount (obtained) (g) | Yield (%) | Aluminum content (ppm) | Maximum absorption wavelength (nm) |
| (3) | (C-1-1a) | 0.7 | (A-2a) | 13.82 | 82 | 0.5 | 326 |
| (4) | (C-1-1b) | 270 | (A-1b) | 13.65 | 78 | 189 | 326 |

(2) Preparation of Liquid Crystal Composition

Liquid crystal compositions (6) to (10) were prepared by the same method as that of Example 1, using the polymerizable liquid crystalline mixtures obtained in Synthesis Example 3 and Synthesis Example 4, and according to the formulations shown in Table 6. The formulations shown in Table 6 are represented by percent by mass (% by mass) of each ingredient before heating. Further, aluminum contents relative to the compound (A-2) in the liquid crystal compositions, which were prepared by mixing the ingredients according to the ratios in the formulations shown in Table 6, are shown in Table 7.

TABLE 6

| Liquid crystal composition | Polymerizable liquid crystalline mixture (mass %) | | Polymerization initiator (mass %) | Leveling agent (mass %) | Polymerization inhibitor (mass %) | Solvent (mass %) |
|---|---|---|---|---|---|---|
| | (A-2a) | (A-2b) | | | | |
| (6) | 12.14 | 0.10 | 0.73 | 0.01 | 0.02 | 87.00 |
| (7) | 11.89 | 0.35 | 0.73 | 0.01 | 0.02 | 87.00 |
| (8) | 10.98 | 1.26 | 0.73 | 0.01 | 0.02 | 87.00 |
| (9) | 5.79 | 6.45 | 0.73 | 0.01 | 0.02 | 87.00 |
| (10) | 2.54 | 9.70 | 0.73 | 0.01 | 0.02 | 87.00 |

Each of the obtained liquid crystal compositions (6) to (10) contains a polymer of the polymerizable liquid crystal compound (A-2). A weight-average molecular weight and an area percentage value of the polymer were measured by GPC. The results are shown in Table 7.

TABLE 7

| Liquid crystal composition | Aluminum content (ppm) relative to compound (A-2) | Molecular weight of polymer (Mw) | Area percentage of polymer (%) | Liquid crystal composition Maximum absorption wavelength (nm) |
|---|---|---|---|---|
| (6) | 2 | 10165 | 0.42 | 326 |
| (7) | 6 | 13450 | 0.59 | 326 |
| (8) | 20 | 16452 | 1.46 | 326 |
| (9) | 100 | 33021 | 8.93 | 326 |
| (10) | 150 | 54300 | 14.4 | 326 |

(3) Evaluation of Storage Stability, Production of Optical Film (Retardation Film), and Evaluation of Alignment Defect With respect to the obtained liquid crystal compositions (6) to (10), storage stability was evaluated by the same method as that of Example 1. Further, optical films were produced by the same method as that of Example 1, and evaluations of an alignment defect were carried out on the obtained optical films. The results are shown in Table 8.

TABLE 8

| | | Liquid crystal composition | | | | Optical film (retardation film) | |
|---|---|---|---|---|---|---|---|
| | | Liquid crystal composition | Molecular weight of polymer (Mw) | Area percentage of polymer (%) | Storage stability | Re(450)/Re(550) | Alignment defect |
| Example | 6 | (6) | 10165 | 0.42 | 4 | 0.95 | 4 |
| | 7 | (1) | 13450 | 0.59 | 4 | 0.95 | 4 |
| | 8 | (8) | 16452 | 1.46 | 4 | 0.95 | 4 |
| | 9 | (9) | 33021 | 8.93 | 4 | 0.95 | 4 |
| | 10 | (10) | 54300 | 14.4 | 4 | 0.95 | 4 |

3. Example 11 to 15

(1) Synthesis of Polymerizable Liquid Crystal Compound (1-1) Synthesis Example (5)

According to the following method, a polymerizable liquid crystalline mixture (A-3a) containing a polymerizable liquid crystal compound represented by the following formula (A-3) (hereinafter, also referred to as "a compound (A-3)") and aluminum was synthesized.

minum content in the polymerizable liquid crystalline mixture (A-3a), and a maximum absorption wavelength ($\lambda_{max}$) of the compound (A-3) are shown in Table 9. The yield of the polymerizable liquid crystalline mixture (A-3a) was calculated based on the compound (F-1-3).

(1-2) Synthesis Example (6)

A polymerizable liquid crystalline mixture (A-3b) containing a compound (A-3) and aluminum was obtained under the same conditions as those of Synthesis Example (2)

[Chemical Formula 179]

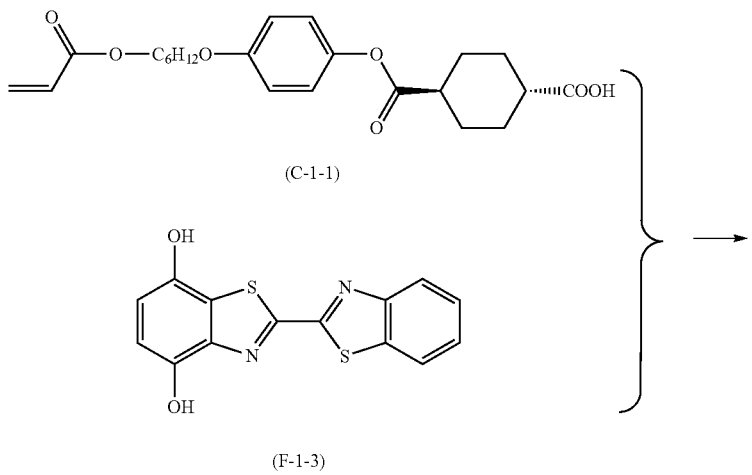

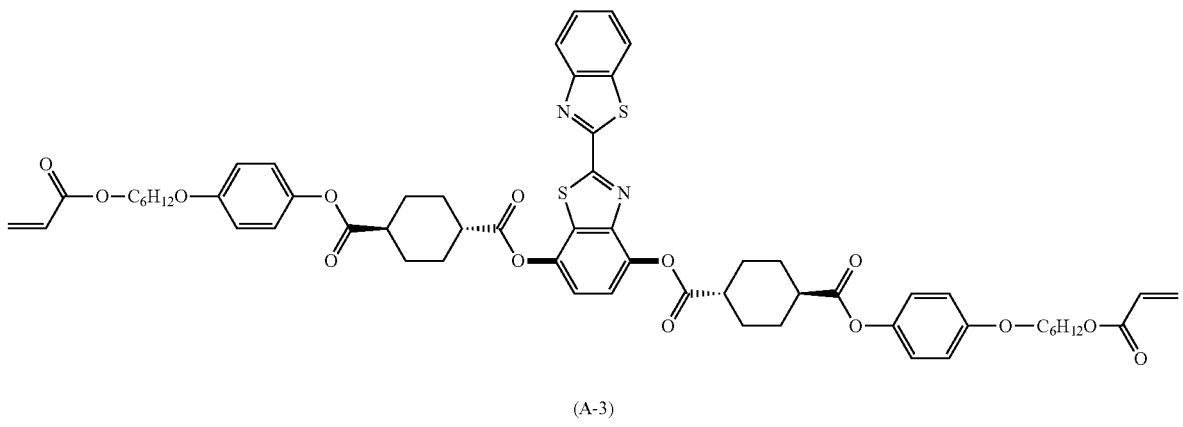

A polymerizable liquid crystalline mixture (A-3a) containing the compound (A-3) and aluminum was obtained under the same conditions as those of Synthesis Example (1) except that a compound (F-1-3) was used instead of the compound (F-1-1) used in Synthesis Example 1. Further, the compound (F-1-3) was synthesized with reference to a patent document (JP-A-2011-207765) An aluminum content in the compound (C-1-1a), an amount of the obtained polymerizable liquid crystalline mixture (A-3a), a yield of the polymerizable liquid crystalline mixture (A-3a), an aluexcept that a compound (F-1-3) was used instead of the compound (F-1-1). An aluminum content in the compound (C-1-1b), an amount of the obtained polymerizable liquid crystalline mixture (A-3b), a yield of the polymerizable liquid crystalline mixture (A-3b), an aluminum content in the polymerizable liquid crystalline mixture (A-3b), and a maximum absorption wavelength ($\lambda_{max}$) of the compound (A-3) are shown in Table 9. The yield of the polymerizable liquid crystalline mixture (A-3b) was calculated based on the compound (F-1-3).

TABLE 9

| | Compound (C-1-1) | | Polymerizable liquid crystalline mixture | Amount (obtained) (g) | Yield (%) | Compound (A-1) | |
|---|---|---|---|---|---|---|---|
| Synthesis Example | Compound (C-1-1) | Aluminum content (ppm) | | | | Aluminum content (ppm) | Maximum absorption wavelength (nm) |
| (5) | (C-1-1a) | 0.7 | (A-3a) | 11.73 | 80 | 0.5 | 342 |
| (6) | (C-1-1b) | 270 | (A-3b) | 12.17 | 83 | 176 | 342 |

(2) Preparation of Liquid Crystal Composition

Liquid crystal compositions (11) to (18) were prepared by the same method as that of Example 1, using the polymerizable liquid crystalline mixtures obtained in Synthesis Example 5 and Synthesis Example 6, and according to formulations shown in Table 10. The formulations shown in Table 10 are represented by percent by mass (% by mass) of each ingredient before heating. Further, aluminum contents relative to the compound (A-3) in the liquid crystal compositions, which were prepared by mixing the ingredients according to the ratios in the formulations shown in Table 10, are shown in Table 11.

TABLE 10

| Liquid crystal composition | Polymerizable liquid crystalline mixture (mass %) | | Polymerization initiator (mass %) | Leveling agent (mass %) | Polymerization inhibitor (mass %) | Solvent (mass %) |
|---|---|---|---|---|---|---|
| | (A-3a) | (A-3b) | | | | |
| (11) | 12.14 | 0.10 | 0.73 | 0.01 | 0.02 | 87.00 |
| (12) | 11.86 | 0.38 | 0.73 | 0.01 | 0.02 | 87.00 |
| (13) | 10.87 | 1.36 | 0.73 | 0.01 | 0.02 | 87.00 |
| (14) | 5.30 | 6.94 | 0.73 | 0.01 | 0.02 | 87.00 |
| (16) | 1.81 | 10.43 | 0.73 | 0.01 | 0.02 | 87.00 |

Each of the obtained liquid crystal compositions (11) to (15) contains a polymer of the polymerizable liquid crystal compound (A-3). A weight-average molecular weight and an area percentage value of the polymer were measured by GPC. The results are shown in Table 11.

TABLE 11

| Liquid crystal composition | Aluminum content (ppm) relative to compound (A-3) | Molecular weight of polymer (Mw) | Area percentage of polymer (%) | Liquid crystal composition Maximum absorption wavelength (nm) |
|---|---|---|---|---|
| (11) | 2 | 11003 | 0.44 | 342 |
| (12) | 6 | 13860 | 0.61 | 342 |
| (13) | 20 | 16390 | 1.49 | 342 |
| (14) | 100 | 29980 | 9.03 | 342 |
| (15) | 150 | 57602 | 15.1 | 342 |

(3) Evaluation of Storage Stability, Production of Optical Film (Retardation Film), and Evaluation of Alignment Defect With respect to the obtained liquid crystal compositions (11) to (15), storage stability was evaluated by the same method as that of Example 1. Further, optical films were produced by the same method as that of Example 1, and evaluations of an alignment defect were carried out on the obtained optical films. The results are shown in Table 12.

TABLE 12

| | | Liquid crystal composition | | | Optical film (retardation film) | |
|---|---|---|---|---|---|---|
| | Liquid crystal composition | Molecular weight of polymer (Mw) | Area percentage of polymer (%) | Storage stability | Re(450)/ Re(550) | Alignment defect |
| Example 11 | (11) | 11003 | 0.44 | 4 | 0.87 | 4 |
| 12 | (12) | 13860 | 0.61 | 4 | 0.87 | 4 |
| 13 | (13) | 16390 | 1.49 | 4 | 0.87 | 4 |
| 14 | (14) | 29980 | 9.03 | 4 | 0.87 | 4 |
| 15 | (15) | 57602 | 15.1 | 4 | 0.87 | 4 |

4. Comparative Example 1 to 6

(1) Preparation of Liquid Crystal Composition

Liquid crystal compositions (16) to (21) were prepared by the same method as that of Example 1, using the polymerizable liquid crystalline mixtures (A-1a) to (A-3b) obtained in Synthesis Example (1) to (6), and according to formulations shown in Table 13. The formulations shown in Table 13 are represented by percent by mass (% by mass) of each ingredient before heating. Further, aluminum contents relative to a polymerizable liquid crystal compound contained in a liquid crystal composition are shown in Table 14.

TABLE 13

| Liquid crystal composition | Polymerizable liquid crystalline mixture | Polymerizable liquid crystalline mixture (mass %) | Polymerization initiator (mass %) | Leveling agent (mass %) | Polymerization inhibitor (mass %) | Solvent (mass %) |
|---|---|---|---|---|---|---|
| (16) | (A-1a) | 12.24 | 0.73 | 0.01 | 0.02 | 87.00 |
| (17) | (A-1b) | 12.24 | 0.73 | 0.01 | 0.02 | 87.00 |
| (18) | (A-2a) | 12.24 | 0.73 | 0.01 | 0.02 | 87.00 |
| (19) | (A-2b) | 12.24 | 0.73 | 0.01 | 0.02 | 87.00 |
| (20) | (A-3a) | 12.24 | 0.73 | 0.01 | 0.02 | 87.00 |
| (21) | (A-3b) | 12.24 | 0.73 | 0.01 | 0.02 | 87.00 |

(2) Evaluation of Storage Stability

With respect to the obtained liquid crystal composition (16), (18), and (20), storage stability was evaluated by the same method as that of Example 1. The results are shown in Table 14. With respect to liquid crystal compositions (17), (19), and (21), however, since gelation occurred during heating and mixing the ingredients constituting each of the liquid crystal composition, storage stability could not be evaluated.

As shown in Tables 4, 8, and 12, precipitation of crystals was prevented for a long period of time after the beginning of storage of liquid crystal compositions in Examples 1 to 15, which contain polymerizable liquid crystal compounds having 3 or more (further, 5 or more) ring structures in the main chain and contain 1 ppm or more and 170 ppm or less of aluminum relative to the polymerizable liquid crystal compound, and the liquid crystal compositions in Examples 1 to 15 have excellent storage stability. Further, optical films produced from liquid crystal compositions in Example 1 to 15 were alignment-defect-free optical films. On the other hand, although the liquid crystal compositions containing the same polymerizable liquid crystal compound as that used in Examples of the present invention were used, when aluminum contents in the liquid crystal compositions relative to the polymerizable liquid crystal compound were less than 1 ppm (Comparative Examples 1, 3, and 5), a polymer of the polymerizable liquid crystal compound was not obtained, and precipitation occurred immediately after the beginning of storage, and thus inferior storage stability was demonstrated.

TABLE 14

| | | Liquid crystal composition | | | | |
|---|---|---|---|---|---|---|
| | | Liquid crystal composition | Aluminum content (ppm) relative to polymerizable liquid crystal compound | Molecular weight of polymer (Mw) | Area percentage of polymer (%) | Storage stability |
| Comparative Example | 1 | (16) | 0.5 | Not detected | | 1 |
| | 2 | (17) | 180 | Gelated during heating | | Inoperable |
| | 3 | (18) | 0.5 | Not detected | | 1 |
| | 4 | (19) | 189 | Gelated during heating | | Inoperable |
| | 5 | (20) | 0.5 | Not detected | | 1 |
| | 6 | (21) | 176 | Gelated during heating | | Inoperable |

5. Example 16 to Example 17, and Comparative Example 7

Results of storage stability test using liquid crystal compositions prepared from polymerizable liquid crystalline mixtures and aluminum chloride added to the mixture are shown below.

(1) Preparation of Liquid Crystal Composition

Liquid crystal compositions (22), (23), and (24) were prepared by the same method as that of Example 1 using the polymerizable liquid crystalline mixture (A-1a) obtained in Synthesis Example (1), and according to formulations shown in Table 15 except that the polymerizable liquid crystalline mixture (A-1a), aluminum chloride (manufactured by KANTO CHEMICAL CO., INC.), a polymerization initiator (IRGACURE 369), a leveling agent (BYK-361N), a polymerization inhibitor (BHT), and a solvent (NMP) were added. The formulations shown in Table 15 are represented by percent by mass (% by mass) of each ingredient before heating relative to total amount (100% by mass) of the liquid crystal composition polymerizable liquid crystalline mixture (A-1a), aluminum chloride, a polymerization initiator, a leveling agent, a polymerization inhibitor, and a solvent]. Further, aluminum contents (IPC analysis method) relative to the compound (A-1) in the liquid crystal compositions, which were prepared by mixing the ingredients according to the ratios in the formulations shown in Table 15, are shown in Table 1.6. Further, every one of aluminum contents of the polymerization initiator (IRGACURE 369), leveling agent (BYK-361N) polymerization inhibitor (BHT), and solvent (NMP) used in the compositions is 0 (zero) ppm.

Each of the obtained liquid crystal compositions (22), (23), and (24) contained polymers of the polymerizable liquid crystal compound (A-1). Weight-average molecular weights and area percentage values of the polymers were measured by GPC. The results are shown in Table 16. Results of maximum absorption wavelengths obtained by measurement of each of the liquid crystal compositions are also shown in Table 16. However, with respect to the liquid crystal composition (24), molecular weight of polymer (Mw), area percentage of polymer, and a maximum absorption wavelength could not be measured due to gelation during heating.

TABLE 16

| Liquid crystal composition | Aluminum content relative to compound (A-1) (ppm) | Molecular weight of polymer (Mw) | Area percentage of polymer (%) | Liquid crystal composition maximum absorption wavelength (nm) |
|---|---|---|---|---|
| (22) | 10 | 15521 | 0.68 | 352 |
| (23) | 100 | 25487 | 1.22 | 352 |
| (24) | 200 | Gelated during heating | | |

(3) Evaluation of Storage Stability, Production of Optical Film (Retardation Film), and Evaluation of Alignment Defect With respect to the obtained liquid crystal compositions (22) and (23), storage stability was evaluated by the same method as that of Example 1. Further, optical films were produced by the same method as that of Example 1, and evaluations of an alignment defect were carried out on the obtained optical films. The results are shown in Table 17. With respect to the obtained liquid crystal composition (24), however, evaluation of storage stability and production of an optical film could not be performed due to gelation of the composition.

TABLE 15

| Liquid crystal composition | Polymerizable liquid crystalline mixture (A-1a) (mass %) | Aluminum chloride (mass %) | polymerization initiator (mass %) | Leveling agent (mass %) | polymerization inhibitor (mass %) |
|---|---|---|---|---|---|
| (22) | 12.23 | 0.001 | 0.73 | 0.01 | 0.02 |
| (23) | 12.23 | 0.006 | 0.73 | 0.01 | 0.02 |
| (24) | 12.23 | 0.012 | 0.73 | 0.01 | 0.02 |

TABLE 17

| | Liquid crystal composition | | | | Optical film (Phase difference film) | |
|---|---|---|---|---|---|---|
| | Liquid crystal composition | Molecular weight of polymer (Mw) | Area percentage of polymer (%) | Storage stability | Re(450)/ Re(550) | Alignment defect |
| Example 16 | (22) | 15521 | 0.87 | 4 | 0.87 | 4 |
| 17 | (23) | 25487 | 1.22 | 4 | 0.87 | 4 |
| Comparative Example 7 | (24) | Gelated during heating | | Inoperable | Impossible to produce film | |

What is claimed is:

1. A liquid crystal composition comprising:
a polymerizable liquid crystal compound having 3 or more ring structures in the main chain;
at least one organic solvent selected from the group consisting of amides, ketones, ethers, and esters; and aluminum,
wherein a content of the aluminum is 1 ppm or more and 170 ppm or less relative to the polymerizable liquid crystal compound, and
wherein the polymerizable liquid crystal compound is a polymerizable liquid crystal compound represented by the following formula (A):

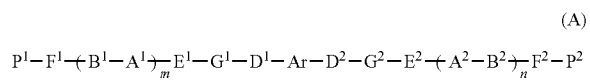
(A)

in formula (A), m and n, each independently, represent an integer of 0 to 3,
$B^1$, $B^2$, $D^1$, $D^2$, $E^1$, and $E^2$, each independently, represent —$CR^1R^2$—, —$CH_2$—$CH_2$—, —O—, —S—, —CO—O—, —O—CO—, —O—CO—O—, —C(=S)—O—, —O—C(=S)—, —O—C(=S)—O—, —CO—$NR^1$—, —$NR^2$—CO—, —O—$CH_2$—, —$CH_2$—O—, —S—$CH_2$—, —$CH_2$—S—, or a single bond, and $R^1$ and $R^2$, each independently, represent a hydrogen atom, a fluorine atom, or an alkyl group having 1 to 4 carbon atoms,
$A^1$, $A^2$, $G^1$, and $G^2$, each independently, represent a divalent alicyclic hydrocarbon group having 3 to 16 carbon atoms or a divalent aromatic hydrocarbon group having 6 to 20 carbon atoms, wherein a hydrogen atom contained in the alicyclic hydrocarbon group and the aromatic hydrocarbon group can be replaced by a halogen atom, —$R^3$, —$OR^3$, a cyano group, or a nitro group, —$CH_2$— contained in the alicyclic hydrocarbon group can be replaced by —O—, —S—, —NH—, or —$NR^4$—, —CH(—)— contained in the alicyclic hydrocarbon group can be replaced by —N(—)—, $R^3$ and $R^4$, each independently, represent an alkyl group having 1 to 4 carbon atoms, wherein a hydrogen atom contained in the alkyl group can be replaced by a fluorine atom,
$F^1$ and $F^2$, each independently, represent an alkane diyl group having 1 to 12 carbon atoms, wherein a hydrogen atom contained in the alkane diyl group can be replaced by —$OR^3$ or a halogen atom, and —$CH_2$— contained in the alkane diyl group can be replaced by —O— or —CO—,
$P^1$ and $P^2$, each independently, represent a hydrogen atom or a polymerizable group, with the proviso that at least one of $P^1$ and $P^2$ represents a polymerizable group, and
Ar is an optionally substituted divalent aromatic group, wherein at least one nitrogen atom, oxygen atom, or sulfur atom is contained in the aromatic group.

2. The liquid crystal composition according to claim 1, wherein both $G^1$ and $G^2$ are trans-cyclohexane-1,4-diyl groups.

3. The liquid crystal composition according to claim 1, wherein the optionally substituted divalent aromatic group represented by Ar in the formula (A) has 10 or more and 30 or less 7c-electrons.

4. The liquid crystal composition according to claim 1, wherein a maximum absorption wavelength ($\lambda_{max}$) of the polymerizable liquid crystal compound is 300 to 400 nm.

5. The liquid crystal composition according to claim 1, wherein Ar in the formula (A) is an aromatic group having a heterocycle.

6. The liquid crystal composition according to claim 5, wherein the aromatic group having a heterocycle is an aromatic group having a benzothiazole group.

7. A retardation film made from a liquid crystal composition according to claim 1.

8. The retardation film according to claim 7, satisfying the following formula (1):

$$0.80 \leq Re(450)/Re(550) < 1.00 \quad (1)$$

wherein Re(450) represents a front retardation value with respect to a light having a wavelength (λ) of 450 nm and Re(550) represents a front retardation value with respect to a light having a wavelength (λ) of 550 nm.

9. A polarizing plate comprising the retardation film according to claim 7.

10. A polarizing plate comprising the retardation film according to claim 8.

11. An optical display comprising the polarizing plate according to claim 9.

12. An optical display comprising the polarizing plate according to claim 10.

* * * * *